(12) United States Patent
Gupta et al.

(10) Patent No.: US 11,560,357 B2
(45) Date of Patent: Jan. 24, 2023

(54) METHODS OF PRODUCING PYRAZOLE COMPOUNDS

(71) Applicant: TORRENT PHARMACEUTICALS LIMITED, Ahmedabad (IN)

(72) Inventors: Ramesh Chandra Gupta, Gandhinagar (IN); Mohan Singaravel, Gandhinagar (IN); Laxmikant Chhipa, Gandhinagar (IN); Ashok Kasundra, Gandhinagar (IN)

(73) Assignee: Torrent Pharmaceuticals Limited, Ahmedabad (IN)

( * ) Notice: Subject to any disclaimer, the term of this patent is extended or adjusted under 35 U.S.C. 154(b) by 0 days.

(21) Appl. No.: 17/277,036

(22) PCT Filed: Sep. 21, 2019

(86) PCT No.: PCT/IB2019/058005
§ 371 (c)(1),
(2) Date: Mar. 17, 2021

(87) PCT Pub. No.: WO2020/058945
PCT Pub. Date: Mar. 26, 2020

(65) Prior Publication Data
US 2022/0033358 A1    Feb. 3, 2022

(30) Foreign Application Priority Data

Sep. 22, 2018   (IN) .............................. 201821035741

(51) Int. Cl.
*C07D 231/12*    (2006.01)
(52) U.S. Cl.
CPC .................................. *C07D 231/12* (2013.01)
(58) Field of Classification Search
CPC .................................................... C07D 231/12
See application file for complete search history.

(56) References Cited

U.S. PATENT DOCUMENTS

| | | | |
|---|---|---|---|
| 8,143,424 B2 | 3/2012 | Chhipa et al. |
| 8,378,118 B2 | 2/2013 | Chhipa et al. |
| 8,486,996 B2 | 7/2013 | Eberle et al. |
| 2012/0202816 A1 | 8/2012 | Chhipa et al. |

FOREIGN PATENT DOCUMENTS

| | | |
|---|---|---|
| CN | 101891618 B | 11/2010 |
| CN | 102351702 B | 2/2012 |

OTHER PUBLICATIONS

Cioffi, F., et al., "TRC150094, A Novel Fundtional Analog of Iodothyronines, Reduces Adiposity by Increasing Energy Expenditure and Fatty Acid Oxidation in Rats Receiving a High-Fat Diet", The FASEB Journal, 24(9) 2451-3461 (2010).
Hasratyan, A.H., et al., "Aqueous N-Methylmorpholine N-Oxide as a New Medium for Alkylation of Pyrazoles", Chemistry of Heterocyclic Compounds, 54(7), 751-754.
International Search Report dated Dec. 20, 2019 issued in PCT/IB2019/058005.

*Primary Examiner* — Shawquia Jackson
(74) *Attorney, Agent, or Firm* — Melissa M. Hayworth; E. Joseph Gess

(57) ABSTRACT

The present invention is directed to methods of producing substituted pyrazole based compounds through novel intermediates and unique processes for preparing such intermediates which enables synthesis of final product through commercially viable route of synthesis. The present invention is also directed to novel methods of producing substituted pyrazole based thyroid like compounds, and solid forms of 3-{4-[(7-hydroxy-6-methyl-indan-4-yl)methyl]-3,5-dimethyl-1H-pyrazol-1-yl}-propanoic acid, its pharmaceutical compositions, and methods of preparation thereof.

8 Claims, 10 Drawing Sheets

METHODS OF PRODUCING PYRAZOLE COMPOUNDS

FIELD OF THE INVENTION

The present invention relates to methods of producing substituted pyrazole based compounds through novel intermediates and unique processes for preparing such intermediates which enables synthesis of final product through commercially viable route of synthesis. The present invention also relates to novel methods of producing substituted pyrazole based thyroid like compounds, and solid forms of 3-{4-[(7-hydroxy-6-methyl-indan-4-yl)methyl]-3,5-dimethyl-1H-pyrazol-1-yl}-propanoic acid, its pharmaceutical compositions, and methods of preparation thereof.

BACKGROUND OF THE INVENTION

Substituted pyrazole based thyroid like compounds are disclosed in U.S. Pat. Nos. 8,143,424 and 8,378,118. The synthetic route described in these patents include protecting hydroxy group of intermediate with methyl iodide, thereafter subsequent synthetic conversions are carried out. The methyl protecting group is eventually deprotected with boron tribromide to yield final product. Methyl iodide and boron tribromide are highly hazardous in nature. Hence, there is a need in the art to provide alternate methods of producing substituted pyrazole based thyroid like compounds which avoid use of these reagents and also suitable for commercial manufacturing.

Furthermore, the synthetic method for production of intermediates described in the aforementioned U.S. patents involve use of hazardous reagents such as zinc-mercury and aluminium chloride. The method also involves reaction at elevated temperature, high vacuum distillation, and column chromatography for purification which makes the drug product synthesis not viable at commercial scale because it consumes more solvent, time, and energy. Accordingly, the present inventors have developed novel routes of synthesis which is devoid of above drawbacks and the final product is produced through commercially viable route of synthesis.

Solid forms of 3-{4-[(7-hydroxy-6-methyl-indan-4-yl)methyl]-3,5-dimethyl-1H-pyrazol-1-yl}propanoic acid are also described herein. The properties of a solid relevant to its efficacy as a drug can be dependent on the form of the solid. For example, in a drug substance, variation in the solid form can lead to differences in properties such as dissolution rate, oral absorption, bio availability, toxicology results, and also clinical efficacy. The solid forms of 3-{4-[(7-hydroxy-6-methyl-indan-4-yl)methyl]-3,5-dimethyl-1H-pyrazol-1-yl}-propanoic acid described herein are crystalline forms, salts, solvates, and hydrates of 3-{4-[(7-hydroxy-6-methyl-indan-4-yl)methyl]-3,5-dimethyl-1H-pyrazol-1-yl}propanoic acid.

SUMMARY OF THE INVENTION

The present invention is directed to a method for producing substituted pyrazole compound of Formula (I):

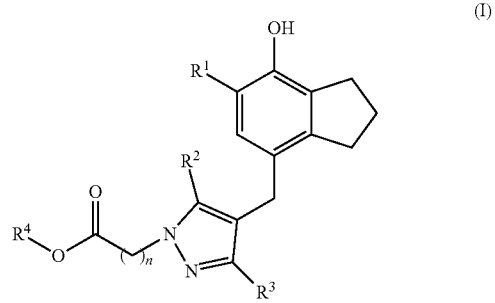

wherein:
$R^1$, $R^2$ and $R^3$ are each independently selected from H, $C_{1-6}$ alkyl, $C_{1-6}$ alkoxy, or halogen;
$R^4$ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, cyclic imide, or $C_{1-20}$ alkyl tricyclic;
n is 1 to 5;
or its pharmaceutically acceptable salts, solvates, co-crystals, and hydrates thereof;
comprising
protecting a compound of Formula (II),

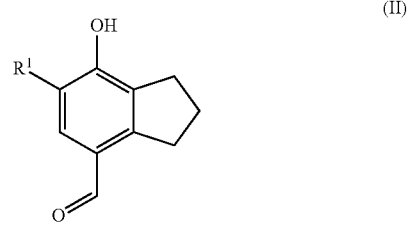

wherein, IV is as described above; with a suitable protecting group to obtain a compound of Formula (III),

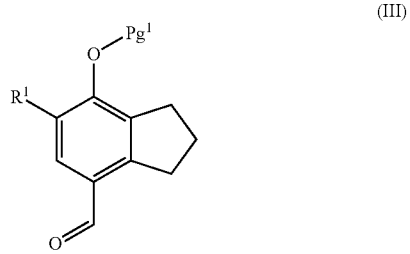

wherein $R^1$ is as defined above and $Pg^1$ is hydroxy protecting group with the proviso that $Pg^1$ is not methyl; reducing the compound of Formula (III) with suitable reducing agent to obtain a compound of Formula (IV),

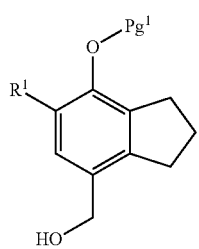
(IV)

wherein R¹ and Pg¹ are defined above; reacting the compound of Formula (IV) with suitable hydroxy activating agent to obtain a compound of Formula (V),

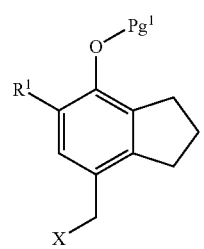
(V)

wherein R¹ and Pg¹ are as defined above, and X is a leaving group; converting the compound of Formula (V) to a compound of Formula (VI),

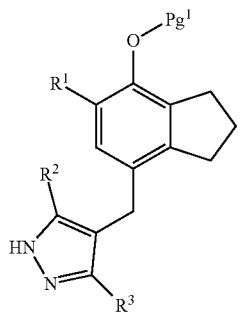
(VI)

wherein R², R³ and Pg¹ are as defined above; reacting the compound of Formula (VI) with a compound of Formula (VII) or (VIIb),

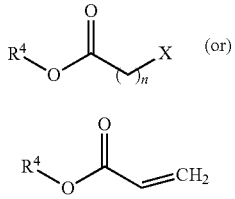
(VII) (or)
(VIIb)

wherein R⁴ and n are as defined above, and X is a leaving group; to obtain a compound of Formula (VIII),

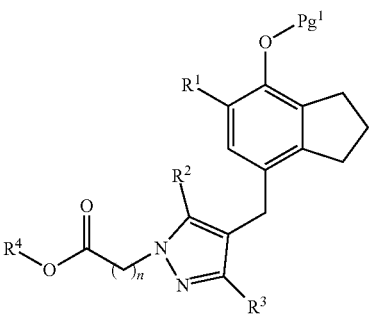
(VIII)

wherein R¹, R², R³, R⁴, n, and Pg¹ are as defined above; and deprotecting the compound of Formula (VIII) to obtain substituted pyrazole compound of Formula (I).

In a preferred embodiment, the substituents R¹, R², and R³ are methyl; R⁴ is H or $C_{1-6}$ alkyl; n is 2; X is Cl, Br, or I; and Pg¹ is benzyl.

The present invention is also directed to a method for producing substituted pyrazole compound of Formula (I):

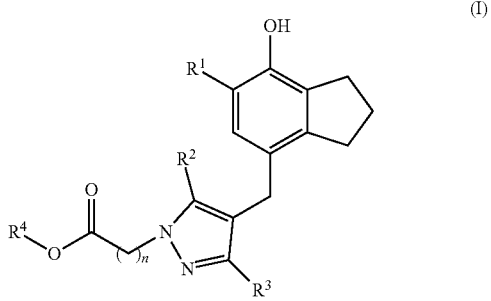
(I)

wherein:
R¹, R² and R³ are each independently selected from H, $C_{1-6}$ alkyl, $C_{1-6}$ alkoxy, or halogen;
R⁴ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, cyclic imide, or $C_{1-20}$ alkyl tricyclic;
n is 1 to 5;
or its pharmaceutically acceptable salts, solvates, co-crystals, and hydrates thereof;
comprising
converting a compound of Formula (V),

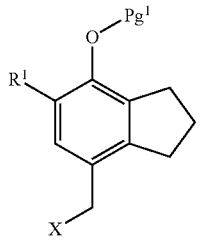
(V)

wherein R¹ is as defined above and Pg¹ is hydroxy protecting group with the proviso that Pg¹ is not methyl, and X is a leaving group; to a compound of Formula (VIa),

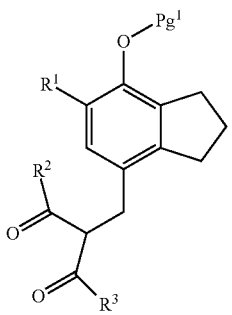

(VIa)

wherein $R^1$, $R^2$, $R^3$ and $Pg^1$ are as defined above; reacting the compound of Formula (VIa) with hydrazine to obtain a compound of Formula (VI),

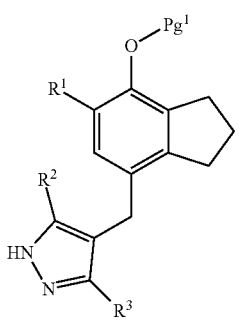

(VI)

wherein $R^1$, $R^2$, $R^3$ and $Pg^1$ are as defined above; and converting the compound of Formula (VI) to substituted pyrazole compound of Formula (I).

In a preferred embodiment, the substituents $R^1$, $R^2$, and $R^3$ are methyl; $R^4$ is H or $C_{1-6}$ alkyl; n is 2; X is Cl; and $Pg^1$ is benzyl.

The present invention is also directed to a method for producing substituted pyrazole compound of Formula (I):

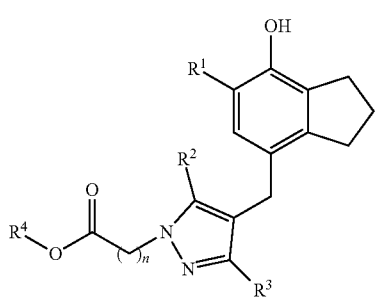

(I)

wherein:
$R^1$, $R^2$ and $R^3$ are each independently selected from H, $C_{1-6}$ alkyl, $C_{1-6}$ alkoxy, or halogen;
$R^4$ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, cyclic imide, or $C_{1-20}$ alkyl tricyclic;
n is 1 to 5;

or its pharmaceutically acceptable salts, solvates, co-crystals, and hydrates thereof;

comprising protecting a compound of Formula (IX),

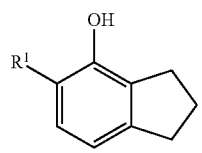

(IX)

wherein $R^1$ is as defined above; with a suitable protecting group to obtain a compound of Formula (X),

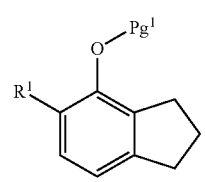

(X)

wherein $R^1$ is as defined above and $Pg^1$ is hydroxy protecting group with the proviso that $Pg^1$ is not methyl; converting the compound of Formula (X) to a compound of Formula (V),

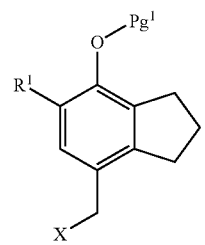

(V)

wherein $R^1$ and $Pg^1$ are as defined above, and X is a leaving group; and converting the compound of Formula (V) to substituted pyrazole compound of Formula (I).

[OR]

protecting a compound of Formula (II),

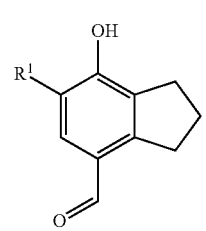

(II)

wherein $R^1$ is as described above; with a suitable protecting group to obtain a compound of Formula (III),

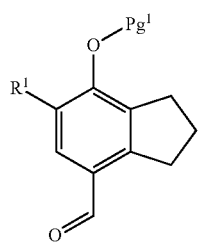

(III)

wherein R¹ is as defined above and Pg¹ is hydroxy protecting group with the proviso that Pg¹ is not methyl; reacting the compound of Formula (III) with a reducing agent to obtain a compound of Formula (IV),

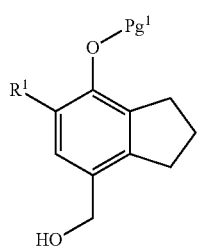

(IV)

wherein R¹ and Pg¹ are defined above;

reacting the compound of Formula (IV) with suitable hydroxy activating agent to obtain a compound of Formula (V),

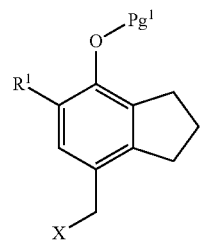

(V)

wherein R¹ and Pg¹ are as defined above, and X is a leaving group; and converting the compound of Formula (V) to substituted pyrazole compound of Formula (I).

In a preferred embodiment, the substituents R¹, R², and R³ are methyl; R⁴ is H or $C_{1-6}$ alkyl; n is 2; X is Cl; and Pg¹ is benzyl.

The present invention is further directed to a method for producing substituted pyrazole compound of Formula (I):

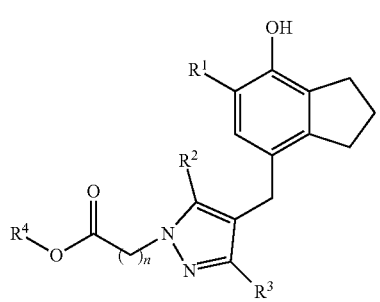

(I)

wherein:
R¹, R² and R³ are each independently selected from H, $C_{1-6}$ alkyl, $C_{1-6}$ alkoxy, or halogen;
R⁴ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, cyclic imide, or $C_{1-20}$ alkyl tricyclic;
n is 1 to 5;
or its pharmaceutically acceptable salts, solvates, co-crystals, and hydrates thereof;
comprising
hydrolysing a compound of Formula (VIIIa), when R⁴ is $C_{1-10}$ saturated or unsaturated alkyl, $C_{1-10}$ substituted or unsubstituted alkylaryl, $C_{3-10}$ cycloalkyl, aryl, heteroaryl, $C_{1-10}$ alkyl silyl, $C_{1-10}$ alkyl silyl ethers, substituted or unsubstituted haloalkyl, cyclic imide, or $C_{1-20}$ alkyl tricyclic;

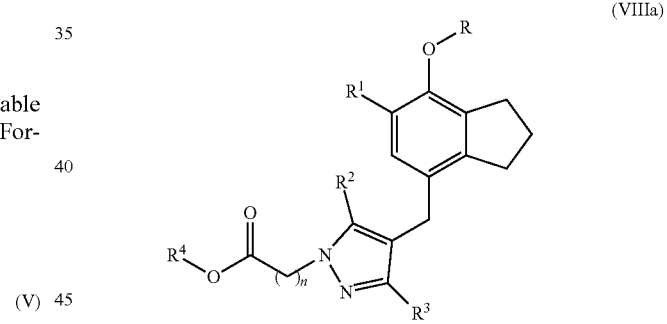

(VIIIa)

wherein R is selected from H or Pg¹;
wherein R, R¹, R², R³, n, are as defined above and Pg¹ is hydroxy protecting group with the proviso that Pg¹ is not methyl; to obtain a compound of Formula (XI),

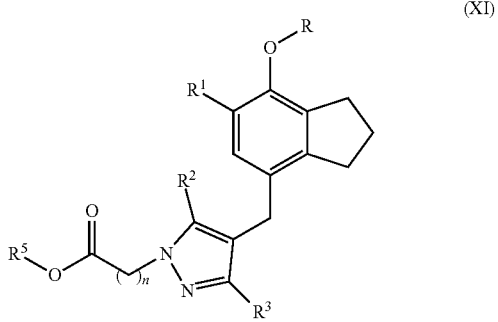

(XI)

wherein R, $R^1$, $R^2$, $R^3$, n, and $Pg^1$ are as defined above and $R^5$ is H; and optionally deprotecting the compound of Formula (XI) to yield substituted pyrazole compound of Formula (I).

In a preferred embodiment, the substituents $R^1$, $R^2$, and $R^3$ are methyl; $R^4$ is H or $C_{1-6}$ alkyl; n is 2; X is Cl; and $Pg^1$ is benzyl.

The present invention is further directed to a method for producing substituted pyrazole compound of Formula (I):

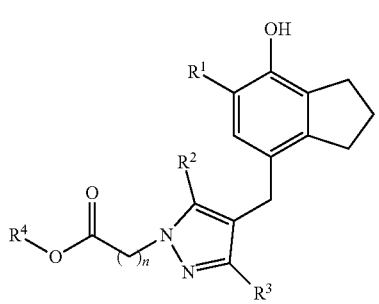
(I)

wherein:
$R^1$, $R^2$ and $R^3$ are each independently selected from H, $C_{1-6}$ alkyl, $C_{1-6}$ alkoxy, or halogen;
$R^4$ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, cyclic imide, or $C_{1-20}$ alkyl tricyclic;
n is 1 to 5;
or its pharmaceutically acceptable salts, solvates, co-crystals, and hydrates thereof;
comprising
converting a compound of Formula (III),

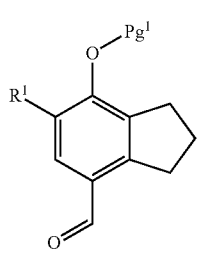
(III)

wherein $R^1$ is as defined above and $Pg^1$ is hydroxy protecting group with the proviso that $Pg^1$ is not methyl; to a compound of Formula (XII),

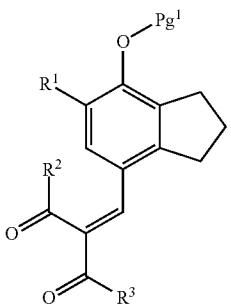
(XII)

wherein $R^2$, $R^3$ and $Pg^1$ are as defined above; reducing a compound of Formula (XII) to obtain a compound of Formula (VIa),

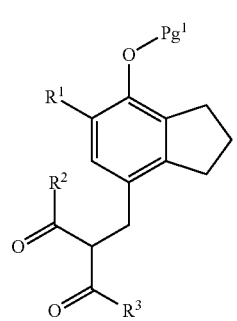
(VIa)

wherein $R^1$, $R^2$, $R^3$ and $Pg^1$ are as defined above; reacting a compound of Formula (VIa) with hydrazine to obtain a compound of Formula (VI),

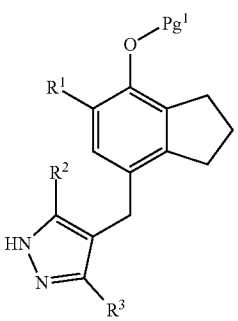
(VI)

wherein $R^1$, $R^2$, $R^3$ and $Pg^1$ are as defined above; and converting the compound of Formula (VI) to substituted pyrazole compound of Formula (I).

In a preferred embodiment, the substituents $R^1$, $R^2$, and $R^3$ are methyl; $R^4$ is H or $C_{1-6}$ alkyl; n is 2; and $Pg^1$ is benzyl.

The present invention is further directed to a method for producing a compound of Formula (IX),

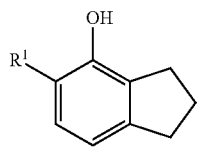

wherein R¹ is selected from H, $C_{1-6}$ alkyl, $C_{1-6}$ alkoxy, and halogen;
comprising
protecting a compound of Formula (XIII),

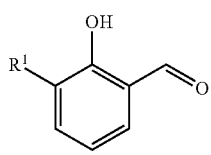

wherein R¹ is as defined above; with a suitable protecting group to obtain a compound of Formula (XIV),

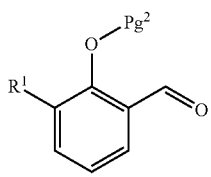

wherein R¹ as defined above and $Pg^2$ is hydroxy protecting group selected from tosyl or benzoyl;
reacting a compound of Formula (XIV) with 2,2-dimethyl-1,3-dioxane-4,6-dione to obtain a compound of Formula (XV).

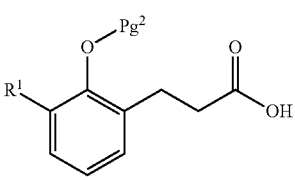

wherein R¹ and $Pg^2$ are as defined above; cyclizing the compound of Formula (XV) to obtain a compound of Formula (XVI),

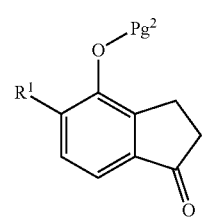

wherein R¹ and $Pg^2$ are as defined above; deprotecting the compound of Formula (XVI) to obtain a compound of Formula (XVII),

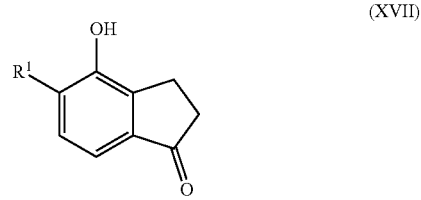

wherein R¹ are as defined above; and reducing the compound of Formula (XVII) to yield a compound of Formula (IX).

In a preferred embodiment, the substituent R¹ is methyl.

The present invention is further directed to a method for producing a compound of Formula (IX),

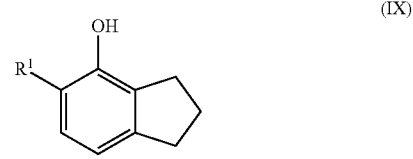

wherein R¹ is selected from H, $C_{1-6}$ alkyl, $C_{1-6}$ alkoxy, and halogen;
comprising
protecting a compound of Formula (XIII),

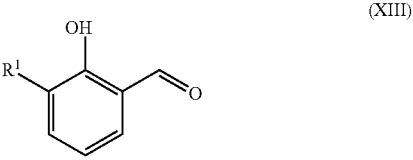

wherein IV is as defined above; with a suitable protecting group to obtain a compound of Formula (XIV),

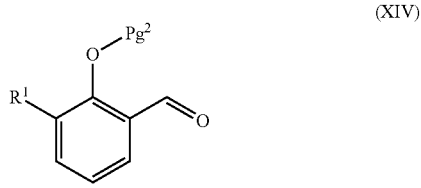

wherein IV as defined above and $Pg^2$ is hydroxy protecting group selected from tosyl or benzoyl;
reacting a compound of Formula (XIV) with 2,2-dimethyl-1,3-dioxane-4,6-dione to obtain a compound of Formula (XV),

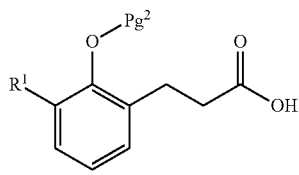

(XV)

wherein $R^1$ and $Pg^2$ are as defined above; cyclizing the compound of Formula (XV) to obtain a compound of Formula (XVI),

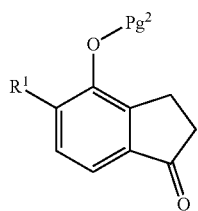

(XVI)

wherein $R^1$ are as defined above; reducing the compound of Formula (XVI) to obtain a compound of Formula (XVIa),

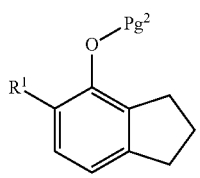

(XVIa)

wherein $R^1$ and $Pg^2$ are as defined above; and deprotecting the compound of Formula (XVIa) to obtain a compound of Formula (IX).

In a preferred embodiment, the substituent $R^1$ is methyl.

The present invention is further directed to a method for producing substituted pyrazole compound of Formula (I):

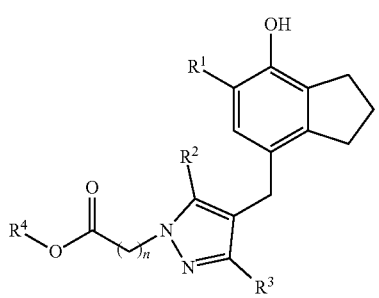

(I)

wherein:

$R^1$, $R^2$ and $R^3$ are each independently selected from H, $C_{1-6}$ alkyl, $C_{1-6}$ alkoxy, or halogen;

$R^4$ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, cyclic imide, or $C_{1-20}$ alkyl tricyclic;

n is 1 to 5;

or its pharmaceutically acceptable salts, solvates, co-crystals, and hydrates thereof;

comprising reacting a compound of Formula (VI),

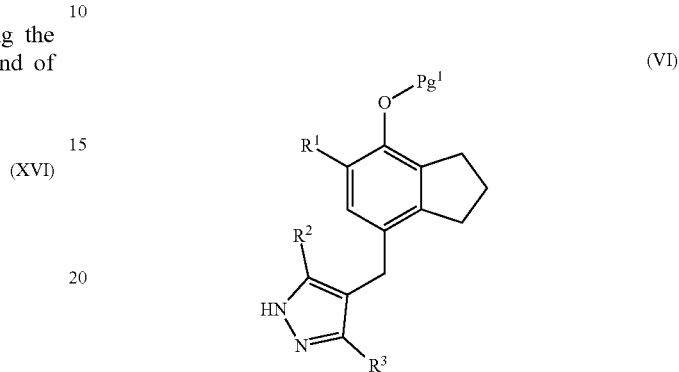

(VI)

wherein $R^1$, $R^2$, $R^3$ and $Pg^1$ are as defined above; with a compound of Formula (VIIa) or (VIIc),

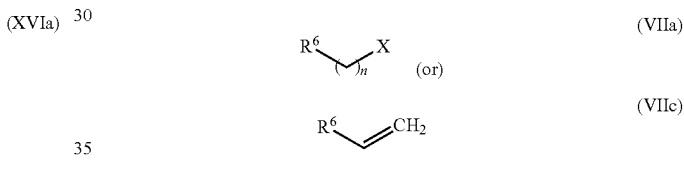

(VIIa)

(or)

(VIIc)

wherein $R^6$ is selected from mono or di-carboxylic acid, acid chloride, ester, nitrile, aldehyde, alcohol, amide, alkyl, alkenyl, alkynyl, alkyl halide, or keto group; X is a leaving group; and n is as defined above; to obtain a compound of Formula (XVIII),

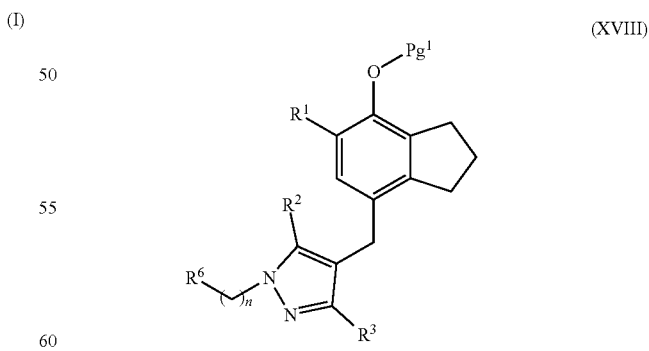

(XVIII)

wherein $R^1$, $R^2$, $R^3$, $R^6$, n, and $Pg^1$ are as defined above; optionally converting the compound of Formula (XVIII) to a compound of Formula (VIII),

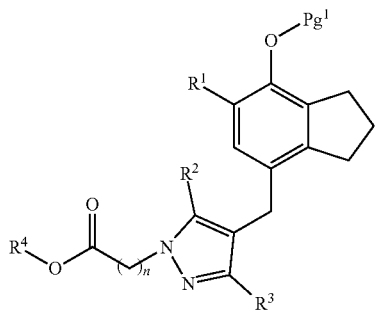
(VIII)

wherein $R^1$, $R^2$, $R^3$, $R^4$, n, and $Pg^1$ are as defined above; and deprotecting the compound of Formula (VIII) to obtain substituted pyrazole compound of Formula (I).

In a preferred embodiment, the substituents $R^1$, $R^2$, and $R^3$ are methyl; $R^4$ is H or $C_{1-6}$ alkyl; $R^6$ is ester; n is 2; and $Pg^1$ is benzyl.

The present invention is further directed to novel intermediate compounds, which are useful in the preparation of substituted pyrazole compound of Formula (I). The novel intermediate compounds of the present invention include compounds of Formula (III), (V), (VI), (VIa), (VIII), and (XII).

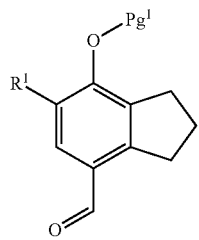
(III)

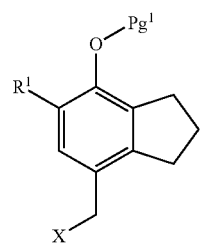
(V)

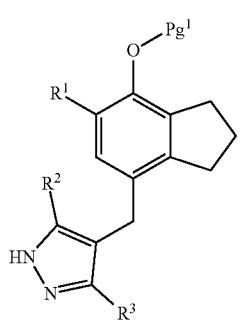
(VI)

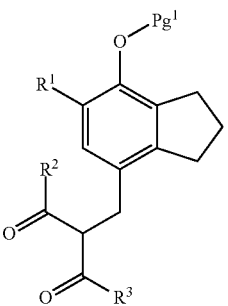
(VIa)

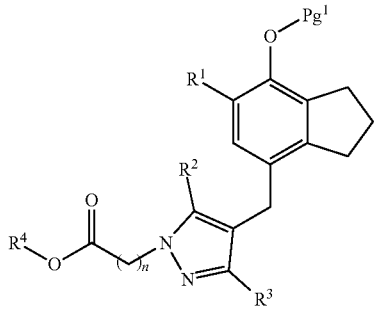
(VIII)

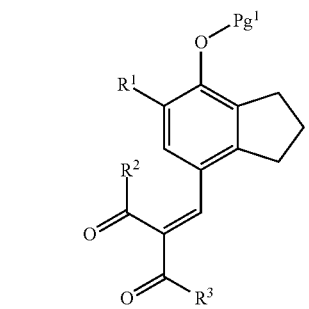
(XII)

wherein $R^1$, $R^2$, $R^3$, $R^4$, X, n, and $Pg^1$ are as defined above.

In a preferred embodiment, the substituents $R^1$, $R^2$, and $R^3$ are methyl; $R^4$ is H or $C_{1-6}$ alkyl; n is 2; and $Pg^1$ is benzyl.

The present invention is directed to a novel method of producing substituted pyrazole compound of Formula (I):

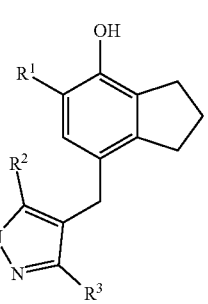
(I)

wherein:
$R^1$, $R^2$ and $R^3$ are each independently selected from H, $C_{1-6}$ alkyl, $C_{1-6}$ alkoxy, or halogen;
$R^4$ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, or $C_{1-20}$ alkyl tricyclic;
n is 1 to 5;
or its pharmaceutically acceptable salts, solvates, co-crystals, and hydrates thereof;
comprising
condensing a compound of Formula (XIX),

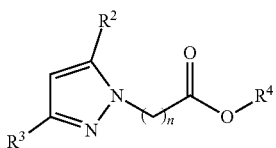

(XIX)

wherein $R^2$, $R^3$, $R^4$ and n are as defined above; with a compound of Formula (XX),

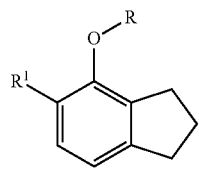

(XX)

wherein R is H or $Pg^1$;
wherein $Pg^1$ is hydroxy protecting group, and $R^1$ is as defined above; in the presence of a condensing agent to obtain a compound of Formula (VIIIa),

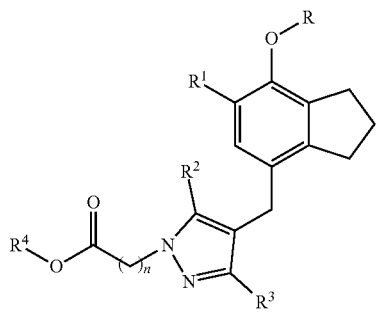

(VIIIa)

wherein R, $R^1$, $R^2$, $R^3$, $R^4$ and n are as defined above; and optionally deprotecting and/or hydrolysing the compound of Formula (VIIIa) to yield substituted pyrazole compound of Formula (I).

In a preferred embodiment, the substituents $R^1$, $R^2$, and $R^3$ are methyl; $R^4$ is H or $C_{1-6}$ alkyl; n is 2; and $Pg^1$ is methyl or benzyl.

In one embodiment, the compound of Formula (XIX),

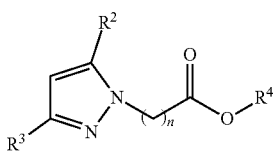

(XIX)

wherein $R^2$, $R^3$, $R^4$ and n are as defined above; is produced by the method, comprising condensing a compound of Formula (XXI),

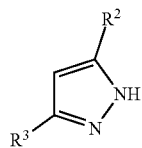

(XXI)

wherein $R^2$, $R^3$, $R^4$ and n are as defined above; with a compound of Formula (VII),

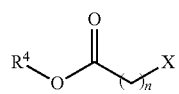

(VII)

wherein $R^4$ and n are as defined above, and X is a leaving group; to obtain the compound of Formula (XIX).

In a preferred embodiment, the substituents $R^2$ and $R^3$ are methyl; $R^4$ is H or $C_{1-6}$ alkyl; n is 2; and X is Cl or Br.

The present invention is also directed to a novel method of producing substituted pyrazole compound of Formula (I):

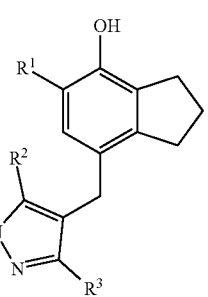

(I)

wherein:
$R^1$, $R^2$ and $R^3$ are each independently selected from H, $C_{1-6}$ alkyl, $C_{1-6}$ alkoxy, or halogen;
$R^4$ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, or $C_{1-20}$ alkyl tricyclic;
n is 1 to 5;
or its pharmaceutically acceptable salts, solvates, co-crystals, and hydrates thereof;
comprising
condensing a compound of Formula (XX),

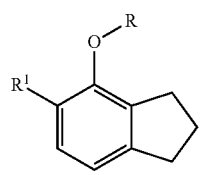

(XX)

wherein R is H or $Pg^1$,
wherein $Pg^1$ is hydroxy protecting group, and $R^1$ is as defined above; with a compound of Formula (XXII),

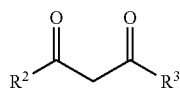

(XXII)

wherein $R^2$ and $R^3$ are as defined above; in the presence of a condensing agent to obtain a compound of Formula (VIb),

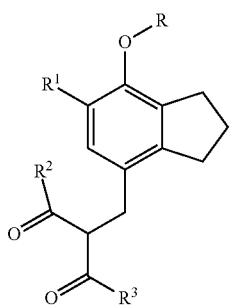

(VIb)

wherein R, $R^1$, $R^2$, and $R^3$ are as defined above; cyclizing the compound of Formula (VIb) with hydrazine to yield a compound of Formula (VIc),

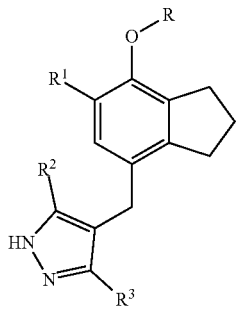

(VIc)

wherein R, $R^1$, $R^2$, and $R^3$ are as defined above; and converting the compound of Formula (VIc) to substituted pyrazole compound of Formula (I).

In a preferred embodiment, the substituents $R^1$, $R^2$, and $R^3$ are methyl; $R^4$ is H or $C_{1-6}$ alkyl; n is 2; and $Pg^1$ is methyl or benzyl.

The present invention is also directed to a novel method of producing substituted pyrazole compound of Formula (I):

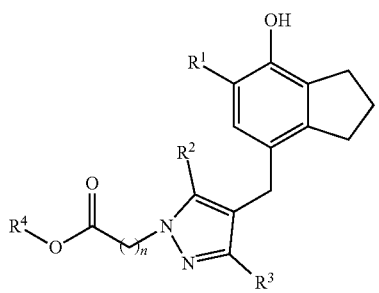

(I)

wherein:

$R^1$, $R^2$ and $R^3$ are each independently selected from H, $C_{1-6}$ alkyl, $C_{1-6}$ alkoxy, or halogen;

$R^4$ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, or $C_{1-20}$ alkyl tricyclic;

n is 1 to 5;

or its pharmaceutically acceptable salts, solvates, co-crystals, and hydrates thereof;

comprising condensing a compound of Formula (XX),

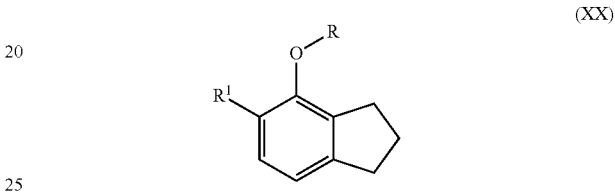

(XX)

wherein R is H or $Pg^1$;

wherein $Pg^1$ is hydroxy protecting group, and $R^1$ is as defined above; with a compound of Formula (XXIII),

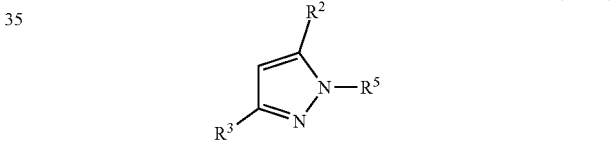

(XXIII)

wherein $R^1$, and $R^3$ are as defined above and $R^5$ is H or $Pg^3$;

wherein $Pg^3$ is amino protecting group; in the presence of a condensing agent to obtain a compound of Formula (XXIV),

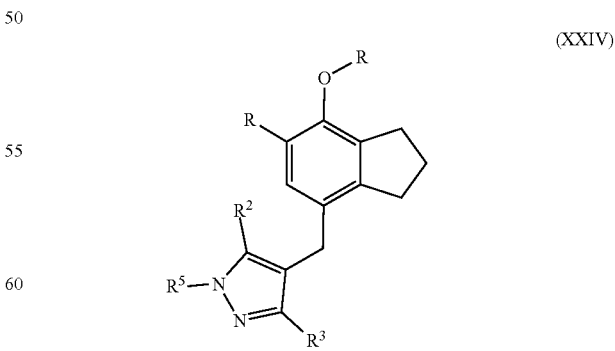

(XXIV)

wherein R, $R^1$, $R^2$, $R^3$, and $R^5$ are as defined above; optionally deprotecting the compound of Formula (XXIV) to yield a compound of Formula (VIc),

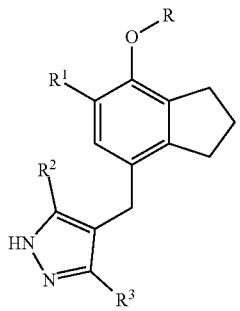
(VIc)

wherein R, R¹, R², and R³ are as defined above; and converting the compound of Formula (VIc) to substituted pyrazole compound of Formula (I).

In a preferred embodiment, the substituents R¹, R², and R³ are methyl; R⁴ is H or $C_{1-6}$ alkyl; n is 2; and $Pg^1$ is methyl or benzyl.

The present invention is further directed to a novel method of producing substituted pyrazole compound of Formula (I):

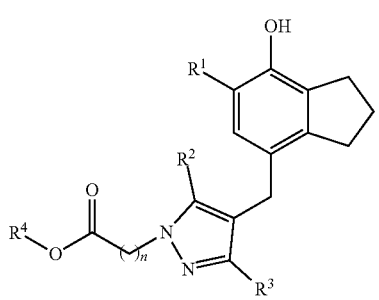
(I)

wherein:
R¹, R² and R³ are each independently selected from H, $C_{1-6}$ alkyl, $C_{1-6}$ alkoxy, or halogen;
R⁴ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, or $C_{1-20}$ alkyl tricyclic;
n is 1 to 5;
or its pharmaceutically acceptable salts, solvates, co-crystals, and hydrates thereof;
comprising
condensing a compound of Formula (XXV),

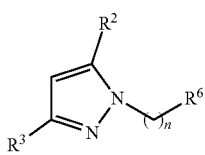
(XXV)

wherein R², R³ and n are as defined above, and R⁶ is selected from mono or di-carboxylic acid, acid chloride, ester, nitrile, aldehyde, alcohol, amide, alkyl, alkenyl, alkynyl, alkyl halide, or keto group; with a compound of Formula (XX),

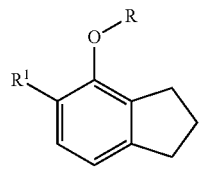
(XX)

wherein R is H or $Pg^1$,
wherein $Pg^1$ is hydroxy protecting group, and R¹ is as defined above; in the presence of a condensing agent to obtain a compound of Formula (XVIIIa),

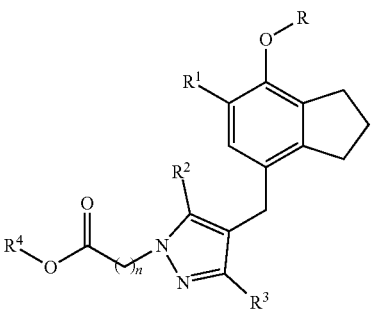
(XVIIIa)

wherein R, R¹, R², R³, R⁴, R⁶ and n are as defined above; optionally converting the compound of Formula (XVIIIa) to a compound of Formula (VIIIa), (VIIIa)

wherein R, R¹, R², R³, R⁴, and n are as defined above; and optionally deprotecting and/or hydrolysing the compound of Formula (VIIIa) to yield substituted pyrazole compound of Formula (I).

In a preferred embodiment, the substituents R¹, R², and R³ are methyl; R⁴ is H or $C_{1-6}$ alkyl; n is 2; and $Pg^1$ is methyl or benzyl.

In one embodiment, the compound of Formula (XXV),

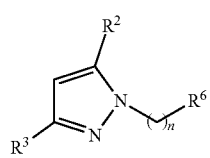
(XXV)

wherein $R^2$, $R^3$, $R^6$ and n are as defined above; is produced by the method, comprising condensing a compound of Formula (XXI),

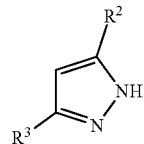

(XXI)

wherein $R^2$ and $R^3$ are as defined above; with a compound of Formula (VIIa),

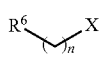

(VIIa)

wherein $R^6$ and n are as defined above, and X is a leaving group; to obtain the compound of Formula (XXV).

In a preferred embodiment, the substituents $R^2$ and $R^3$ are methyl; $R^6$ is mono carboxylic acid or ester; n is 2; and X is Cl or Br.

The present invention is further directed to a method of making 3-{4-[(7-hydroxy-6-methyl-indan-4-yl)methyl]-3,5-dimethyl-1H-pyrazol-1-yl}propanoic acid. The method comprises treating ester of 3-{4-[(7-hydroxy-6-methyl-indan-4-yl)methyl]-3,5-dimethyl-1H-pyrazol-1-yl}propanoic acid with acid to yield 3-{4-[(7-hydroxy-6-methyl-indan-4-yl)methyl]-3,5-dimethyl-1H-pyrazol-1-yl}propanoic acid.

The present invention further provides a pharmaceutical composition comprising a therapeutically effective amount of substituted pyrazole compound of Formula (I) and one or more pharmaceutically acceptable excipients and/or carrier.

The present invention further provides polymorphic forms of 3-{4-[(7-hydroxy-6-methyl-indan-4-yl)methyl]-3,5-dimethyl-1H-pyrazol-1-yl}-propanoic acid.

In one aspect, the invention provides crystalline Form-$T_{15-1}$ of 3-{4-[(7-hydroxy-6-methyl-indan-4-yl)methyl]-3,5-dimethyl-1H-pyrazol-1-yl}-propanoic acid.

In one embodiment, the crystalline Form-$T_{15-1}$ of 3-{4-[(7-hydroxy-6-methyl-indan-4-yl)methyl]-3,5-dimethyl-1H-pyrazol-1-yl}propanoic acid that exhibits an X-ray powder diffraction pattern having characteristic peaks expressed in degrees 2-theta at about 6.1±0.2, 7.4±0.2, 10.7±0.2, 11.9±0.2, 12.3±0.2, 12.7±0.2, 14.9±0.2, 18.7±0.2, 20.2±0.2, 22.1±0.2, and 22.9±0.2.

In another embodiment, the crystalline Form-$T_{15-1}$ of 3-{4-[(7-hydroxy-6-methyl-indan-4-yl)methyl]-3,5-dimethyl-1H-pyrazol-1-yl}propanoic acid is characterized by X-ray powder diffraction (XRPD) pattern substantially similar to the XRPD pattern provided in FIG. 1.

In another embodiment, the crystalline Form-$T_{15-1}$ of 3-{4-[(7-hydroxy-6-methyl-indan-4-yl)methyl]-3,5-dimethyl-1H-pyrazol-1-yl}propanoic acid is characterized by a differential scanning calorimetry (DSC) thermogram substantially similar to the DSC thermogram in FIG. 2.

In another embodiment, the crystalline Form-$T_{15-1}$ of 3-{4-[(7-hydroxy-6-methyl-indan-4-yl)methyl]-3,5-dimethyl-1H-pyrazol-1-yl}propanoic acid is characterized by a Thermogravimetric analysis (TGA) curve substantially similar to the TGA curve in FIG. 3.

In another embodiment, the invention provides a method of making crystalline Form-$T_{15-1}$ of 3-{4-[(7-hydroxy-6-methyl-indan-4-yl)methyl]-3,5-dimethyl-1H-pyrazol-1-yl}propanoic acid. The method comprises:
a) treating 3-{4-[(7-hydroxy-6-methyl-indan-4-yl)methyl]-3,5-dimethyl-1H-pyrazol-1-yl}propanoic acid or its ester with aqueous base, and
b) acidifying the reaction mixture of step a) with acid at about 10° C. to about 50° C. to yield crystalline Form-$T_{15-1}$.

In another embodiment, the invention provides a method of making crystalline Form-$T_{15-1}$ of 3-{4-[(7-hydroxy-6-methyl-indan-4-yl)methyl]-3,5-dimethyl-1H-pyrazol-1-yl}propanoic acid. The method comprises:
a) treating 3-(4-{[7-(Pg$^1$-oxy)-6-methyl-indan-4-yl]methyl-3,5-dimethyl-1H-pyrazol-1-yl}propanoic acid or its ester, wherein $Pg^1$ is hydroxy protecting group, with a suitable hydroxy deprotecting agent in presence of aqueous base, and
b) acidifying the reaction mixture of step a) with acid at about 10° C. to about 50° C. to yield crystalline Form-$T_{15-1}$.

In another embodiment, the invention provides a pharmaceutical composition comprising a therapeutically effective amount of a crystalline Form-$T_{15-1}$ of 3-{4-[(7-hydroxy-6-methyl-indan-4-yl)methyl]-3,5-dimethyl-1H-pyrazol-1-yl}propanoic acid and pharmaceutically acceptable excipient and/or carrier.

In another aspect, the invention provides crystalline Form-$T_{15-2}$ of 3-{4-[(7-hydroxy-6-methyl-indan-4-yl)methyl]-3,5-dimethyl-1H-pyrazol-1-yl}-propanoic acid.

In one embodiment, the invention provides crystalline Form-$T_{15-2}$ of 3-{4-[(7-hydroxy-6-methyl-indan-4-yl)methyl]-3,5-dimethyl-1H-pyrazol-1-yl}propanoic acid that exhibits an X-ray powder diffraction pattern having characteristic peaks expressed in degrees 2-theta at about 7.4±0.2, 11.9±0.2, 12.7±0.2, and 14.9±0.2.

In another embodiment, the crystalline Form-$T_{15-2}$ of 3-{4-[(7-hydroxy-6-methyl-indan-4-yl)methyl]-3,5-dimethyl-1H-pyrazol-1-yl}propanoic acid is further characterised by X-ray powder diffraction pattern having characteristic peaks expressed in degrees 2-theta at about 12.2±0.2, 18.7±0.2, 19.7±0.2, 22.1±0.2, 24.8±0.2, and 25.8±0.2.

In another embodiment, the crystalline Form-Tis-2 of 3-{4-[(7-hydroxy-6-methyl-indan-4-yl)methyl]-3,5-dimethyl-1H-pyrazol-1-yl}propanoic acid is characterized by X-ray powder diffraction pattern substantially similar to the X-ray powder diffraction pattern provided in FIG. 4.

In another embodiment, the crystalline Form-Tis-2 of 3-{4-[(7-hydroxy-6-methyl-indan-4-yl)methyl]-3,5-dimethyl-1H-pyrazol-1-yl}propanoic acid is characterized by a differential scanning calorimetry (DSC) thermogram substantially similar to the DSC thermogram in FIG. 5.

In another embodiment, the crystalline Form-Tis-2 of 3-{4-[(7-hydroxy-6-methyl-indan-4-yl)methyl]-3,5-dimethyl-1H-pyrazol-1-yl}propanoic acid is characterized by a Thermogravimetric analysis (TGA) curve substantially similar to the TGA curve in FIG. 6.

In another embodiment, the invention provides a method of making crystalline Form-$T_{15-2}$ of 3-{4-[(7-hydroxy-6-methyl-indan-4-yl)methyl]-3,5-dimethyl-1H-pyrazol-1-yl}propanoic acid. The method comprises:
a) treating 3-{4-[(7-hydroxy-6-methyl-indan-4-yl)methyl]-3,5-dimethyl-1H-pyrazol-1-yl}propanoic acid or its ester with aqueous base,
b) acidifying the reaction mixture of step a) at below 10° C.,
c) isolating the solid, and
d) drying the solid under vacuum to provide crystalline Form-$T_{15-2}$.

In another embodiment, the invention provides a pharmaceutical composition comprising a therapeutically effective amount of a crystalline Form-$T_{15\text{-}2}$ of 3-{4-[(7-hydroxy-6-methyl-indan-4-yl)methyl]-3,5-dimethyl-1H-pyrazol-1-yl}propanoic acid and pharmaceutically acceptable excipient and/or carrier.

In another aspect, the invention provides crystalline Form-Tis-3 of 3-{4-[(7-hydroxy-6-methyl-indan-4-yl) methyl]-3,5-dimethyl-1H-pyrazol-1-yl}-propanoic acid.

In one embodiment, the invention provides crystalline Form-Tis-3 of 3-{4-[(7-hydroxy-6-methyl-indan-4-yl) methyl]-3,5-dimethyl-1H-pyrazol-1-yl}propanoic acid that exhibits an X-ray powder diffraction pattern having characteristic peaks expressed in degrees 2-theta at about 6.2±0.2, 10.7±0.2, 16.5±0.2, and 21.6±0.2.

In another embodiment, the crystalline Form-$T_{15\text{-}3}$ of 3-{4-[(7-hydroxy-6-methyl-indan-4-yl)methyl]-3,5-dimethyl-1H-pyrazol-1-yl}propanoic acid is further characterised by X-ray powder diffraction pattern having characteristic peaks expressed in degrees 2-theta at about 12.4±0.2, 20.3±0.2, 22.5±0.2, and 23.0±0.2.

In another embodiment, the crystalline Form-$T_{15\text{-}3}$ of 3-{4-[(7-hydroxy-6-methyl-indan-4-yl)methyl]-3,5-dimethyl-1H-pyrazol-1-yl}propanoic acid is characterized by X-ray powder diffraction pattern substantially similar to the X-ray powder diffraction pattern provided in FIG. 7.

In another embodiment, the crystalline Form-$T_{15\text{-}3}$ of 3-{4-[(7-hydroxy-6-methyl-indan-4-yl)methyl]-3,5-dimethyl-1H-pyrazol-1-yl}propanoic acid is characterized by a differential scanning calorimetry (DSC) thermogram substantially similar to the DSC thermogram in FIG. 8.

In another embodiment, the crystalline Form-$T_{15\text{-}3}$ of 3-{4-[(7-hydroxy-6-methyl-indan-4-yl)methyl]-3,5-dimethyl-1H-pyrazol-1-yl}propanoic acid is characterized by a Thermogravimetric analysis (TGA) curve substantially similar to the TGA curve in FIG. 9.

In another embodiment, the invention provides a method of making crystalline Form-$T_{15\text{-}3}$ of 3-{4-[(7-hydroxy-6-methyl-indan-4-yl)methyl]-3,5-dimethyl-1H-pyrazol-1-yl}propanoic acid. The method comprises: treating 3-{4-[(7-hydroxy-6-methyl-indan-4-yl)methyl]-3,5-dimethyl-1H-pyrazol-1-yl}propanoic acid or its ester with base in organic solvent or in a mixture of organic solvent and water and then acidifying with acid at above 10° C. to provide crystalline Form-$T_{15\text{-}3}$.

In another embodiment, the invention provides a method of making crystalline Form-$T_{15\text{-}3}$ of 3-{4-[(7-hydroxy-6-methyl-indan-4-yl)methyl]-3,5-dimethyl-1H-pyrazol-1-yl}propanoic acid. The method comprises treating 3-(4-{[7-($Pg^1$-oxy)-6-methyl-indan-4-yl]methyl}-3,5-dimethyl-1H-pyrazol-1-yl)propanoic acid, wherein $Pg^1$ is hydroxy protecting group; with a suitable hydroxy deprotecting agent in organic solvent or in a mixture of organic solvent and water at above 10° C. to yield crystalline Form-$T_{15\text{-}3}$.

In another embodiment, the invention provides a method of making crystalline Form-$T_{15\text{-}3}$ of 3-{4-[(7-hydroxy-6-methyl-indan-4-yl)methyl]-3,5-dimethyl-1H-pyrazol-1-yl}propanoic acid. The method comprises combining 3-{4-[(7-hydroxy-6-methyl-indan-4-yl)methyl]-3,5-dimethyl-1H-pyrazol-1-yl}-propanoic acid with organic solvent and optionally adding anti-solvent to provide crystalline Form-$T_{15\text{-}3}$ of 3-{4-[(7-hydroxy-6-methyl-indan-4-yl)methyl]-3,5-dimethyl-1H-pyrazol-1-yl}propanoic acid.

In another embodiment, the invention provides a pharmaceutical composition comprising a therapeutically effective amount of a crystalline Form-$T_{15\text{-}3}$ of 3-{4-[(7-hydroxy-6-methyl-indan-4-yl)methyl]-3,5-dimethyl-1H-pyrazol-1-yl}propanoic acid and pharmaceutically acceptable excipient and/or carrier.

In another aspect, the invention provides crystalline Form-$T_{15\text{-}4}$ of 3-{4-[(7-hydroxy-6-methyl-indan-4-yl)methyl]-3,5-dimethyl-1H-pyrazol-1-yl}-propanoic acid.

In one embodiment, the crystalline Form-$T_{15\text{-}4}$ of 3-{4-[(7-hydroxy-6-methyl-indan-4-yl)methyl]-3,5-dimethyl-1H-pyrazol-1-yl}propanoic acid is hydrate.

In another embodiment, the invention provides crystalline Form-$T_{15\text{-}4}$ of 3-{4-[(7-hydroxy-6-methyl-indan-4-yl)methyl]-3,5-dimethyl-1H-pyrazol-1-yl}propanoic acid that exhibits an X-ray powder diffraction pattern having characteristic peaks expressed in degrees 2-theta at about 8.1±0.2, 11.9±0.2, 12.6±0.2 and, 19.6±0.2.

In another embodiment, the crystalline Form-$T_{15\text{-}4}$ of 3-{4-[(7-hydroxy-6-methyl-indan-4-yl)methyl]-3,5-dimethyl-1H-pyrazol-1-yl}propanoic acid is characterized by X-ray powder diffraction pattern substantially similar to the X-ray powder diffraction pattern provided in FIG. 10.

In another embodiment, the crystalline Form-$T_{15\text{-}4}$ of 3-{4-[(7-hydroxy-6-methyl-indan-4-yl)methyl]-3,5-dimethyl-1H-pyrazol-1-yl}propanoic acid is characterized by a differential scanning calorimetry (DSC) thermogram substantially similar to the DSC thermogram in FIG. 11.

In another embodiment, the crystalline Form-$T_{15\text{-}4}$ of 3-{4-[(7-hydroxy-6-methyl-indan-4-yl)methyl]-3,5-dimethyl-1H-pyrazol-1-yl}propanoic acid is characterized by a Thermogravimetric analysis (TGA) curve substantially similar to the TGA curve in FIG. 12.

In another embodiment, the invention provides a method of making crystalline Form-$T_{15\text{-}4}$ of 3-{4-[(7-hydroxy-6-methyl-indan-4-yl)methyl]-3,5-dimethyl-1H-pyrazol-1-yl}propanoic acid. The method comprises:

a) treating 3-{4-[(7-hydroxy-6-methyl-indan-4-yl) methyl]-3,5-dimethyl-1H-pyrazol-1-yl}propanoic acid or its ester with aqueous base,
 b) acidifying the reaction mixture of step a) with acid at below 10° C.,
 c) isolating the solid, and
 d) air drying the solid to provide crystalline Form-$T_{15\text{-}4}$.

In another embodiment, the invention provides a pharmaceutical composition comprising a therapeutically effective amount of a crystalline Form-$T_{15\text{-}4}$ of 3-{4-[(7-hydroxy-6-methyl-indan-4-yl)methyl]-3,5-dimethyl-1H-pyrazol-1-yl}propanoic acid and a pharmaceutically acceptable excipient and/or carrier.

In another aspect, the invention provides dimethyl sulfoxide (DMSO) solvate of 3-{4-[(7-hydroxy-6-methyl-indan-4-yl)methyl]-3,5-dimethyl-1H-pyrazol-1-yl}-propanoic acid.

In one embodiment, the invention provides DMSO solvate of 3-{4-[(7-hydroxy-6-methyl-indan-4-yl)methyl]-3,5-dimethyl-1H-pyrazol-1-yl}propanoic acid that exhibits an X-ray powder diffraction pattern having characteristic peaks expressed in degrees 2-theta at about 13.2±0.2, 14.9±0.2, 16.7±0.2, 18.5±0.2, and, 22.4±0.2.

In another embodiment, the DMSO solvate of 3-{4-[(7-hydroxy-6-methyl-indan-4-yl)methyl]-3,5-dimethyl-1H-pyrazol-1-yl}propanoic acid is characterized by X-ray powder diffraction pattern substantially similar to the X-ray powder diffraction pattern provided in FIG. 13.

In another embodiment, the DMSO solvate of 3-{4-[(7-hydroxy-6-methyl-indan-4-yl)methyl]-3,5-dimethyl-1H-pyrazol-1-yl}propanoic acid is also characterized by a differential scanning calorimetry (DSC) thermogram substantially similar to the DSC thermogram in FIG. 14.

In another embodiment, the DMSO solvate of 3-{4-[(7-hydroxy-6-methyl-indan-4-yl)methyl]-3,5-dimethyl-1H-pyrazol-1-yl}propanoic acid is further characterized by a Thermogravimetric analysis (TGA) curve substantially similar to the TGA curve in FIG. 15.

In another embodiment, the invention provides a method of making DMSO solvate of 3-{4-[(7-hydroxy-6-methyl-indan-4-yl)methyl]-3,5-dimethyl-1H-pyrazol-1-yl}propanoic acid. The method comprises treating 3-{4-[(7-hydroxy-6-methyl-indan-4-yl)methyl]-3,5-dimethyl-1H-pyrazol-1-yl}propanoic acid with DMSO to provide DMSO solvate of 3-{4-[(7-hydroxy-6-methyl-indan-4-yl)methyl]-3,5-dimethyl-1H-pyrazol-1-yl}propanoic acid.

In another embodiment, the invention provides a pharmaceutical composition comprising a therapeutically effective amount of DMSO solvate of 3-{4-[(7-hydroxy-6-methyl-indan-4-yl)methyl]-3,5-dimethyl-1H-pyrazol-1-yl}propanoic acid and pharmaceutically acceptable excipient and/or carrier.

In another aspect, the invention provides disodium salt of 3-{4-[(7-hydroxy-6-methyl-indan-4-yl)methyl]-3,5-dimethyl-1H-pyrazol-1-yl}-propanoic acid.

In one embodiment, the invention provides disodium salt of 3-{4-[(7-hydroxy-6-methyl-indan-4-yl)methyl]-3,5-dimethyl-1H-pyrazol-1-yl}propanoic acid that exhibits an X-ray powder diffraction pattern having characteristic peaks expressed in degrees 2-theta at about 13.9±0.2, 14.4±0.2, 19.5±0.2, 21.7±0.2, and, 22.5±0.2.

In another embodiment, the disodium salt of 3-{4-[(7-hydroxy-6-methyl-indan-4-yl)methyl]-3,5-dimethyl-1H-pyrazol-1-yl}propanoic acid is characterized by X-ray powder diffraction pattern substantially similar to the X-ray powder diffraction pattern provided in FIG. 16.

In another embodiment, the disodium salt of 3-{4-[(7-hydroxy-6-methyl-indan-4-yl)methyl]-3,5-dimethyl-1H-pyrazol-1-yl}propanoic acid is also characterized by a differential scanning calorimetry (DSC) thermogram substantially similar to the DSC thermogram in FIG. 17.

In another embodiment, the disodium salt of 3-{4-[(7-hydroxy-6-methyl-indan-4-yl)methyl]-3,5-dimethyl-1H-pyrazol-1-yl}propanoic acid is further characterized by a Thermogravimetric analysis (TGA) curve substantially similar to the TGA curve in FIG. 18.

In another embodiment, the invention provides a method of making disodium salt of 3-{4-[(7-hydroxy-6-methyl-indan-4-yl)methyl]-3,5-dimethyl-1H-pyrazol-1-yl}propanoic acid. The method comprises treating 3-{4-[(7-hydroxy-6-methyl-indan-4-yl)methyl]-3,5-dimethyl-1H-pyrazol-1-yl}propanoic acid with sodium ion source in organic solvent, water or mixture thereof to provide disodium salt of 3-{4-[(7-hydroxy-6-methyl-indan-4-yl)methyl]-3,5-dimethyl-1H-pyrazol-1-yl}propanoic acid.

In another embodiment, the invention provides a pharmaceutical composition comprising a therapeutically effective amount of disodium salt of 3-{4-[(7-hydroxy-6-methyl-indan-4-yl)methyl]-3,5-dimethyl-1H-pyrazol-1-yl}propanoic acid and pharmaceutically acceptable excipient and/or carrier.

In another aspect, the invention provides amorphous form of 3-{4-[(7-hydroxy-6-methyl-indan-4-yl)methyl]-3,5-dimethyl-1H-pyrazol-1-yl}propanoic acid.

In another aspect, the invention provides amorphous solid dispersion of 3-{4-[(7-hydroxy-6-methyl-indan-4-yl)methyl]-3,5-dimethyl-1H-pyrazol-1-yl}propanoic acid.

In another aspect, the invention provides a method treating disease in a subject, comprising the steps of administering therapeutically effective amount of the pharmaceutical composition comprising crystalline Form-$T_{15-1}$ or Form-$T_{15-2}$ or Form-$T_{15-3}$ or Form-$T_{15-4}$, or DMSO solvate, or disodium salt or amorphous form of 3-{4-[(7-hydroxy-6-methyl-indan-4-yl)methyl]-3,5-dimethyl-1H-pyrazol-1-yl}propanoic acid and a pharmaceutically acceptable excipient and/or carrier.

BRIEF DESCRIPTION OF THE DRAWINGS

The novel features of the invention are set forth particularity in the appended aspects. A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
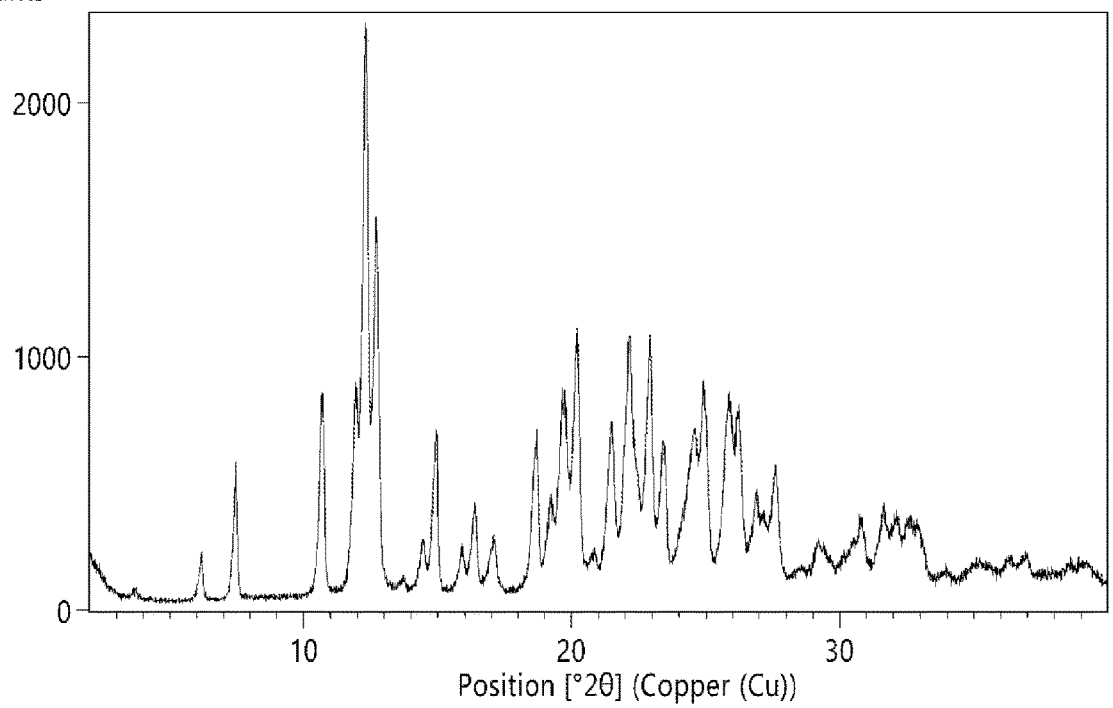
FIG. 1 illustrates an X-ray powder diffraction (XRPD) pattern of the crystalline Form-$T_{15}$-1.

While selected embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The following definitions apply to the terms as used throughout this specification, unless otherwise limited in specific instances.

The singular form "a", "an" and "the" as used herein includes plural references unless the context clearly dictates otherwise.

The term "about" as used herein refers to the numeric value±10% of the indicated value.

The term "suitable protecting group" or "hydroxy protecting group" as used herein refers to a moiety that temporarily blocks hydroxyl reactive site in a compound. Generally, this is done so that a chemical reaction can be carried out selectively at another reactive site in a multifunctional compound, or to stabilize the hydroxy group. The hydroxy protecting group is preferably removable selectively by a chemical reaction. The "suitable protecting group" or "hydroxy protecting group include, the group which forms an ester, ether or silyl-protecting group. For example, the ester formed is acetyl (Ac), benzoyl (Bz) or pivaloyl (Piv). For example, the ether protecting group formed is methyl, benzyl (Bn), methoxyethoxymethyl ether (MEM), trityl (Tr), para-methoxybenzyl (PMB), dimethoxy trityl (DMT), methoxymethyl ether (MOM), tetrahydropyranyl (THP), or ethoxyethyl ether (EE). For example, the silyl protecting group formed is trimethylsilyl (TMS), triethylsilyl (TES), tert-butyldimethylsilyl (TBDMS or TBS), tri-iso-propylsilyloxymethyl (TOM), or triisopropylsilyl (TIPS ether). Other protecting group formed is para-bromobenzoyl, para-nitrobenzoyl, triisopropylsilyl (TIPS), benzyloxymethyl (BOM), p-methoxy-benzyloxymethyl (PMBM), [(3,4-dimethoxybenzypoxy]-methyl (DMBM), methylthiomethyl (MTM), 2-(trimethyl-silyl)-ethoxymethyl (SEM).

The term "solvent," includes single solvent or solvent mixtures, such as water, esters, alcohols, halogenated hydrocarbons, ketones, ethers, polar aprotic solvents, hydrocarbon solvents, or mixtures thereof.

Examples of esters include methyl acetate, ethyl acetate, n-propyl acetate, isopropyl acetate, t-butyl acetate, and n-butyl acetate. Examples of alcohols include those primary, secondary and tertiary alcohols having from one to six carbon atoms. Examples of alcohol include methanol, ethanol, n-propanol, isopropanol, butanol, 2-methoxyethanol and 2-ethoxyethanol. Examples of halogenated hydrocarbons include dichloromethane, chloroform and 1,2-dichloroethane. Examples of ketones include acetone, methyl isobutyl ketone, and methyl ethyl ketone. Examples of ethers include diethyl ether, 2-methyl tetrahydrofuran, cyclopentyl methyl ether, and tetrahydrofuran. Examples of polar aprotic solvents include N,N-dimethylformamide, N,N-dimethylacetamide, dimethylsulphoxide, acetonitrile, and N-methylpyrrolidone. Examples of hydrocarbon solvents include $C_6$ to $C_7$ substituted or unsubstituted acyclic or cyclic aliphatic hydrocarbon, hexane, heptane, cyclohexane and aromatic hydrocarbons like toluene, xylene, benzene.

The term "leaving group" according to the present invention includes, but not limited to, halo group, especially fluoro, chloro, bromo, or iodo and substituted or unsubstituted alkyl sulfonyloxy groups, substituted or unsubstituted aryl sulfonyloxy groups, substituted or unsubstituted arylalkyl sulfonyloxy groups, and substituted or unsubstituted haloalkyl sulfonyloxy groups.

The term "reducing agent" according to the present invention refers to a reagent that causes reduction reaction of an organic molecule. Examples of suitable reducing agent include hydride reducing agents, boranes and metal catalysts. Preferred hydride reducing agents are sodium borohydride, sodium triacetoxyborohydride, lithium borohydride, diisobutylaluminium hydride, lithium aluminum hydride, triethylsilane, and the like; preferred boranes include diborane and borane dimethylsulfide in refluxing tetrahydrofuran and the like. Metal catalysts are copper, palladium, platinum, nickel, zinc, iron, rhodium, ruthenium either as the elements or in the form of a salt and either pure or on an inert carrier. Suitable catalysts include raney-nickel, palladium on carbon, platinum on carbon and the like. Preferred metal catalysts are selected from the group consisting of raney-nickel, palladium on carbon, platinum on carbon, ruthenium on carbon, rhodium on carbon, and platinum dioxide, in particular from raney-nickel, palladium on carbon, platinum on carbon, and platinum dioxide.

The term "acid catalyst" according to the present invention may be a Lewis acid or a Bronsted acid. Lewis acids, for example, are zinc chloride, zinc iodide, aluminium chloride, aluminium bromide, and boron trifluoride etherate. Bronsted acids, for example, include inorganic acids, such as hydrochloric acid, hydrobromic acid, nitric acid, sulfuric acid and phosphoric acids, carboxylic acids, such as acetic and trifluoroacetic acids, sulfonic acids, such as methanesulfonic, benzenesulphonic, 1-naphthalenesulfonic, 1-butanesulfonic, ethane sulfonic, 4-ethylbenzene sulfonic, 1-hexane sulfonic, 1,5-naphthalene disulfonic, 1-octanesulfonic, camphorsulfonic, trifluoromethane-sulfonic, and p-toluene-sulfonic acids. Additionally, the term "acid catalyst" includes cation exchange resins, which may also be referred to as resin-based acid catalysts.

The term "hydroxy deprotecting agent" according to the present invention refers to a reagent that is capable of cleaving hydroxy protecting group to form free hydroxy group. Examples of such hydroxy deprotecting reagents include, but not limited to, boron tribromide, tetra-n-butylammonium fluoride, tris(dimethylamino)sulfonium difluorotrimethylsilicate, hydrogen bromide, hydrogen fluoride, hydrogen fluoride pyridine, silicon tetrafluoride, hexafluorosilicic acid, cesium fluoride, hydrochloric acid, acetic acid, trifluoroacetic acid, pyridinium p-toluenesulfonate, p-toluenesulfonic acid, formic acid, periodic acid, palladium on carbon, and base.

The term "hydroxy activating agent" according to the present invention refers to a reagent that increases the reactivity of a hydroxyl group thereby making the hydroxyl group a better leaving group. Examples of such hydroxy activating agents include p-toluenesulfonyl chloride, 4-nitrophenylsulfonyl chloride, thionyl chloride, oxalyl chloride, triflic anhydride, mesyl chloride, mesyl anhydride, triphenylphosphine, acyl chloride, 4-dimethylaminopyridine, trialkyl phosphine, triarylphosphine, triheteroarylphosphine, trimethylphosphine, tributylphosphine, tri(o-tolyl)phosphine, tri(m-tolyl)phosphine, tri(p-tolyl)phosphine, tri(2-pyridyl)-phosphine, tri(3-pyridyl)-phosphine, or tri(4-pyridyl)phosphine.

The term "acid," according to present invention includes mineral acids or organic acids. The mineral acids include hydrochloric acid, hydrobromic acid, sulfuric acid, nitric acid, and phosphoric acid, and the like. The organic acids include formic acid, acetic acid, propionic acid, butyric acid, valeric acid, caproic acid, oxalic acid, lactic acid, malic acid, citric acid, carbonic acid, succinic acid, benzoic acid and p-toluenesulphonic acid, and the like.

The term "base," according to present invention includes alkali metal carbonates such as sodium carbonate, potassium carbonate, lithium carbonate and the like; alkali metal bicarbonates such as sodium bicarbonate, potassium bicarbonate and the like; alkali metal hydroxides such as sodium hydroxide, potassium hydroxide, lithium hydroxide and the like;

alkali metal alkoxides such as sodium methoxide, sodium ethoxide, potassium methoxide, potassium ethoxide, sodium tert.butoxide, potassium tert.butoxide, lithium tert.butoxide and the like; alkali metal hydrides such as sodium hydride, potassium hydride, lithium hydride and the like; alkali metal amides such as sodium amide, potassium amide, lithium amide and the like; and organic bases like dimethylamine, diethylamine, diisopropyl amine, diisopropylethylamine, diisobutylamine, triethylamine, pyridine, 4-dimethylaminopyridine, N-methyl morpholine, 2,6-lutidine, lithium diisopropylamide; organosilicon bases such as lithium hexamethyldisilazide, sodium hexamethyldisilazide, potassium hexamethyldisilazide, or mixtures thereof.

The term "amino protecting group" as used herein refers to a moiety that temporarily blocks amine reactive site in a compound. Generally, this is done so that a chemical reaction can be carried out selectively at another reactive site in a multifunctional compound, or to stabilize the amino group. The amino protecting group is preferably removable selectively by a chemical reaction. The "amino protecting group" include, 9-fluorenylmethyl carbamate, formyl, acetyl, trifluoroacetyl, carbobenzyloxy, benzoyl, benzyl, benzyloxycarbonyl, m-nitrophenyloxycarbonyl, o-nitrobenzyloxycarbonyl, 3,5-dimethoxybenzyloxy-carbonyl, p-nitrobenzyloxycarbonyl, p-methoxybenzyl, p-methoxybenzylcarbonyl, 3,4-dimethoxybenzyl, tert-butoxycarbonyl, trimethylsilyl, tosyl, 2-trimethylsilylethane-sulfonyl, diphenylmethyl, trichloroethyl chloroformate, trityl and substituted trityl groups, allyloxycarbonyl, nitroveratryloxycarbonyl, and allyloxycarbonyl.

The term "amino deprotecting agent" as used herein refers to a reagent or combination of reagents which will selectively remove the amino protecting group. The selection of the deprotecting agent to be used in a specific reaction will depend the protecting group and other features of the compound on which the reaction is taking place. Examples of deprotecting agents include, but not limited to, agents such as hydrochloric acid, hydrobromic acid, sulfuric acid, formic acid, trifluoroacetic acid, palladium on carbon, or mixtures thereof.

The term "combining" includes adding, dissolving, slurrying, stirring, or a combination thereof.

The term "therapeutically effective amount" refers to that amount of a compound described herein that is sufficient to effect the intended application including but not limited to disease treatment, as defined below. The therapeutically effective amount may vary depending upon the intended application or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

The term "phase-transfer catalyst" according to present invention includes quaternary ammonium salts, phosphonium salts, crown ethers, polyethylene glycols and combinations thereof. Quaternary ammonium halides include, for example, tetrabutylammonium halides, tetrabutylammonium hydrogen sulfate, tetrabutylammonium thiocyanate, tetrabutylammonium tetrafluoroborate, benzyltributylammonium halides, hexadecyltrimethylammonium halides, hexadecyltrimethylammonium hydrogen sulfate, methyltriethylammonium halides, methyltrioctadecylammonium halides, tetraethylammonium halides, tetraethylammonium hexafluorophosphate, tetraethylammonium tetrafluoroborate, tetrahexylammonium hydrogen sulfate, tetramethylammonium halides, tetraoctylammonium halides and mixtures thereof. Phosphonium salts include, for example, tributylhexadecylphosphonium and tetrabutylphosphonium halides and mixtures thereof. Crown ether include, for example, 12-crown-4, 1-aza-15-crown-5, 18-crown-6, dibenzo-18-crown-6, dicyclohexano-18-crown-6, dicyclohexano-24-crown-8, tris[2-(2-methoxyethoxy)ethyl]amine, 4,7,13,16,21,24-hexaoxa-1,10-diazabicyclo[8.8.8]hexacosane, and mixtures thereof. Polyethylene glycols include, for example, polyethylene glycol 200, 400, 600, 1000, and mixtures thereof.

The term "therapeutic effect," as used herein, refers to a therapeutic benefit and/or a prophylactic benefit as described above. A prophylactic benefit includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable excipient" or "pharmaceutically acceptable carrier" according to the present invention means, but not limited to, any one or more inactive ingredient which is required for the composition of 3-{4-[(7-hydroxy-6-methyl-indan-4-yl)methyl]-3,5-dimethyl-1H-pyrazol-1-yl}propanoic acid in a suitable dosage form. Particularly the excipient includes, but not limited to, diluents, carriers, fillers, bulking agents, binders, disintegrants, polymer, lubricant, glidant, surface active agents, stabilizers, absorption accelerators, flavoring agents, preservatives, antioxidants, buffering agents, release modifying material, coating material and any other excipient commonly used in the pharmaceutical industry.

The term "subject" refers to an animal, such as a mammal, for example a human. The methods described herein can be useful in both human therapeutics and veterinary applications. In some embodiments, the patient is a mammal, and in some embodiments, the patient is human.

Experimental Instrumentation and Conditions

X-ray Power Diffraction (XRPD) was performed with a PANalytical X-ray diffractometer with CuKα-radiation. The standard measuring conditions were: tube power 45 kV/40 mA; step size 0.008° (2θ); step time 10±2 sec; scanning range 2°-40° (2θ); divergence slit automatic; the samples were rotated; an X-Celerator detector was used; the y-axis shows the value intensity and X-axis shows 2-theta value.

Differential Scanning calorimetry (DSC) was performed with a Mettler Toledo Differential Scanning calorimeter 2, using closed aluminium crucibles, and a heating rate of 10° C. min$^{-1}$ over a range from 25° C. to 300° C.

Thermal gravimetric analysis (TGA) was performed with a Mettler Toledo-TG1 using alumina crucible, under a nitrogen atmosphere, and at a heating range of 10° C. min$^{-1}$ over the range of 25° C. to 300° C.

Fourier transform Infrared Spectroscopy (FTIR) was performed with a Bruker Tensor 27 instrument, using 20 scans over the range of 4000 cm$^{-1}$ to 400 cm$^{-1}$ with 2 cm$^{-1}$ resolution.

In one particular aspect of the present invention, protecting hydroxy group of a compound of Formula (II) with a suitable protecting agent is conducted in the presence of a base and an activating agent in a solvent to yield a compound of Formula (III). Preferably, the suitable protecting group is benzyl. The hydroxy protection is preferably carried out in the presence of a base such as lithium hydroxide, sodium hydroxide, potassium hydroxide, magnesium hydroxide, sodium carbonate, potassium carbonate, cesium carbonate, magnesium carbonate, sodium bicarbonate, and potassium bicarbonate. More preferably, the base is potassium carbonate. Preferably, the activating agent is, for example, potassium iodide. The hydroxy protection is preferably carried out in the presence of a polar aprotic solvent such as N,N-dimethylformamide, N,N-dimethylacetamide, dimethylsulphoxide, acetonitrile, and N-methylpyrrolidone. More preferably, the polar aprotic solvent is N,N-dimethylformamide.

The compound of Formula (II) can be prepared from compound of Formula (IX) by the methods as known in the prior art such as, for example, U.S. Pat. No. 8,378,118.

The hydroxy protected compound of Formula (III) is then treated with a reducing agent in the presence of a catalyst in a solvent to provide the compound of Formula (IV), which is further converted to a compound of Formula (V) by reacting a compound of Formula (IV) with hydroxy activating agent in the presence of a solvent. The reduction is preferably carried out in the presence of a reducing agent such as sodium borohydride, sodium triacetoxyborohydride, lithium borohydride, diisobutylaluminium hydride, lithium aluminium hydride. More preferably, the reducing agent is sodium borohydride. Preferably, the reduction is carried out in the presence of a catalyst such as, for example, acetic acid. The reduction is preferably carried out in the presence of a halogenated solvent such as, for example, dichloromethane.

The conversion of a compound of Formula (IV) to a compound of Formula (V) is preferably carried out in the presence of hydroxy activating agent such as p-toluenesulfonyl chloride, 4-nitrophenylsulfonyl chloride, thionyl chloride, oxalyl chloride, triflic anhydride, mesyl chloride, mesyl anhydride, or acyl chloride. More preferably, the hydroxy activating agent is thionyl chloride. The hydroxy activation reaction is preferably carried out in the presence of a solvent such as, for example, dichloromethane.

The compound of Formula (V) is then reacted with acetyl acetone in the presence of a base and an activating agent in a solvent. The obtained product (i.e., compound of Formula (VIa)) is further treated with hydrazine in the presence of acid catalyst in a solvent to yield the compound of Formula (VI). Preferably, the base is selected from lithium hydroxide, sodium hydroxide, potassium hydroxide, magnesium hydroxide, sodium carbonate, potassium carbonate, cesium carbonate, magnesium carbonate, sodium bicarbonate, and potassium bicarbonate. More preferably, the base is potassium carbonate. Preferably, the activating agent is, for example, sodium iodide, or potassium iodide.

The conversion of a compound of Formula (V) to a compound of Formula (VIa) is preferably carried out in the presence of a solvent such as, for example, acetone and a catalytic amount of N,N-dimethylformamide. The acid catalyst is preferably selected from acetic acid or trifluoroacetic acid. More preferably, the acid catalyst is acetic acid. The reaction of compound of Formula (VIa) with hydrazine is preferably carried out in the presence of a solvent selected from methanol, ethanol, n-propanol, isopropanol, butanol, 2-methoxyethanol, and 2-ethoxyethanol. Preferably, the solvent is isopropanol.

The compound of Formula (VI) is then condensed with a compound of Formula (VII) in the presence of a base selected from lithium hydroxide, sodium hydroxide, potassium hydroxide, magnesium hydroxide, sodium carbonate, potassium carbonate, cesium carbonate, magnesium carbonate, sodium bicarbonate, and potassium bicarbonate in a solvent to yield the compound of Formula (VIII). More preferably, the base is cesium carbonate. The condensing reaction is preferably carried out in the presence of a polar aprotic solvent such as, for example, N,N-dimethylformamide.

The reaction of a compound of Formula (VI) with a compound of Formula (VIIb) can be carried out in the presence of copper catalyst, for example, copper(II) chloride or copper(II) sulfate.

The hydroxy deprotection of a compound of Formula (VIII) is conducted with hydroxy deprotecting agent in a solvent to yield the substituted pyrazole compound of Formula (I). Preferably, the hydroxy deprotecting agent is, for example, palladium on carbon. The deprotection reaction is preferably carried out in the presence of hydrogen pressure. The hydrogen pressure can be in the range of about 10 pound per square inch (psi) to about 300 psi. The hydroxy deprotection is preferably carried out in the presence of a solvent selected from methyl acetate, ethyl acetate, n-propyl acetate, isopropyl acetate, n-butyl acetate, methanol, ethanol, n-propanol, isopropanol, butanol, 2-methoxyethanol, and 2-ethoxyethanol. More preferably, the solvent is methanol or ethyl acetate.

In accordance with another aspect of the present invention, protecting hydroxy group of a compound of Formula (IX) with a suitable protecting group is conducted in the presence of a base and an activating agent in a solvent to yield a compound of Formula (X). Preferably, the suitable protecting group is benzyl. The hydroxy protection is preferably carried out in the presence of a base such as lithium hydroxide, sodium hydroxide, potassium hydroxide, magnesium hydroxide, sodium carbonate, potassium carbonate, cesium carbonate, magnesium carbonate, sodium bicarbonate and potassium bicarbonate. More preferably, the base is potassium carbonate. Preferably, the activating agent is, for example, sodium iodide or potassium iodide. The hydroxy protection is preferably carried out in the presence of a polar aprotic solvent such as N,N-dimethylformamide, N,N-dimethylacetamide, dimethylsulphoxide, acetonitrile, and N-methylpyrrolidone. More preferably, the polar aprotic solvent is N,N-dimethylformamide.

The protected compound of Formula (X) is then treated with formaldehyde or paraformaldehyde in the presence of hydrochloric acid and acid catalyst in solvent to yield the compound of Formula (V). The reaction is preferably carried out in the presence of acid catalyst selected from zinc chloride, zinc iodide, aluminum chloride, aluminum bromide, sulfuric acid, phosphoric acid, acetic acid or trifluoroacetic acid. More preferably, the acid catalyst is zinc chloride, acetic acid or mixture thereof. The reaction of a compound of Formula (X) with formaldehyde or paraformaldehyde is preferably carried out in the presence of a solvent selected from methyl acetate, ethyl acetate, n-propyl acetate, isopropyl acetate, and n-butyl acetate. More preferably, the solvent is ethyl acetate.

The conversion of a compound of Formula (V) to substituted pyrazole compound of Formula (I) is carried out by the method as described above.

In another aspect of the present invention, the hydrolysis of a compound of Formula (VIIIa) is conducted by ester hydrolysis in the presence of a base to provide the compound of Formula (XI). The ester hydrolysis is preferably carried out by reacting a compound of Formula (VIII) with a base selected from lithium hydroxide, sodium hydroxide, potassium hydroxide, magnesium hydroxide, sodium carbonate, potassium carbonate, cesium carbonate, magnesium carbonate, sodium bicarbonate, and potassium bicarbonate, in a solvent to yield the compound of Formula (XI). More preferably, the base is sodium hydroxide. The reaction is preferably carried out in the presence of a solvent such as water, tetrahydrofuran or mixture thereof.

The deprotection of a compound of Formula (XI) is carried out with hydroxy deprotecting agent in a solvent to yield the substituted pyrazole compound of Formula (I). Preferably, the hydroxy deprotecting agent is, for example, palladium on carbon. The deprotection reaction is preferably carried out in the presence of hydrogen pressure. The hydrogen pressure can be in the range of about 10 pound per square inch (psi) to about 300 psi. The hydroxy deprotection is preferably carried out in the presence of a solvent selected from methyl acetate, ethyl acetate, n-propyl acetate, isopropyl acetate, n-butyl acetate, methanol, ethanol, n-propanol, isopropanol, butanol, 2-methoxyethanol, and 2-ethoxyethanol. More preferably, the solvent is methanol or ethyl acetate.

In a further aspect of the present invention, the compound of Formula (III) is reacted with acetyl acetone in the presence of a catalyst in a solvent to yield the compound of Formula (XII). The catalyst is preferably selected from piperidine, acetic acid, or mixture thereof. Preferably, the solvent is toluene. The reaction of a compound of Formula (III) with acetyl acetone is preferably carried out at a temperature of about 30° C. to about reflux temperature of the reaction mixture.

The compound of Formula (XII) is further reduced with a suitable reducing agent in the presence of a catalyst to provide the compound of Formula (VIa). The reducing agent and catalyst are preferably selected from zinc and acetic acid, respectively. The reduction of a compound of Formula (XII) with reducing agent is preferably carried out at a temperature of about 0° C. to 50° C.

The compound of Formula (VIa) is further treated with hydrazine in the presence of an acid catalyst in a solvent to yield the compound of Formula (VI). The acid catalyst is preferably selected from acetic acid or trifluoroacetic acid. More preferably, the acid catalyst is acetic acid. The cyclization of a compound of Formula (VIa) with hydrazine in a solvent is preferably carried out at about 20° C. to about 90° C. More preferably, the reaction is carried out at about 60° C. to about 85° C. The reaction of a compound of Formula (VIa) with hydrazine is preferably carried out in the presence of a solvent selected from methanol, ethanol, n-propanol, isopropanol, butanol, 2-methoxyethanol, and 2-ethoxyethanol. More preferably, the solvent is isopropanol.

In a further aspect of the present invention, the compound of Formula (IX) is prepared by protecting a compound of Formula (XIII) with a suitable protecting group which is conducted in the presence of a base and an activating agent in a solvent to yield a compound of Formula (XIV). Preferably, the suitable protecting group is tosyl. The hydroxy protection is preferably carried out in the presence of a base such as lithium hydroxide, sodium hydroxide, potassium hydroxide, magnesium hydroxide, sodium carbonate, potassium carbonate, cesium carbonate, magnesium carbonate, sodium bicarbonate and potassium bicarbonate. More preferably, the base is potassium carbonate. Preferably, the activating agent is, for example, sodium iodide or potassium iodide. The hydroxy protection is preferably carried out in the presence of a polar aprotic solvent such as N,N-dimethylformamide, N,N-dimethylacetamide, dimethylsulphoxide, acetonitrile, and N-methylpyrrolidone. More preferably, the polar aprotic solvent is N,N-dimethylformamide.

The compound of Formula (XIII) can be prepared from 2-methylphenol by the methods known in the prior art such as, for example, by the method as described in U.S. Pat. No. 8,486,996 or by the method as described herein.

The reaction of compound of Formula (XIV) with 2,2-dimethyl-1,3-dioxane-4,6-dione (Meldrum's acid) is carried out in the presence of a base and a catalyst in a solvent to yield a compound of Formula (XV). The reaction is preferably carried out in the presence of a base selected from pyridine, trimethylamine, triethylamine, diethylamine, diisopropylethylamine, imidazoles, triethanolamine, morpholine, or N-methyl morpholine. More preferably, the base is triethylamine. Preferably, the reaction is carried out in the presence of a catalyst such as, for example, formic acid. Further, the reaction is preferably carried out in the presence of a polar aprotic solvent selected from N,N-dimethylformamide, N,N-dimethylacetamide, dimethylsulphoxide, acetonitrile, and N-methylpyrrolidone. More preferably, the polar aprotic solvent is N,N-dimethylformamide.

The cyclization of a compound of Formula (XV) is carried out by reacting a compound of Formula (XV) with halogenating agent and then with Lewis acid in a solvent to yield a compound of Formula (XVI). The halogenating agent is preferably, for example, thionyl chloride. The Lewis acid is preferably selected from zinc chloride, zinc iodide, aluminium chloride, aluminium bromide, and boron trifluoride etherate. More preferably, the Lewis acid is aluminium chloride. The solvent can be preferably selected from methanol, ethanol, n-propanol, isopropanol, butanol, 2-methoxyethanol, 2-ethoxyethanol, dichloromethane, chloroform, 1,2-dichloroethane or mixtures thereof. More preferably, the solvent is dichloromethane, methanol, or mixture thereof.

The deprotection of a compound of Formula (XVI) is conducted in the presence of a base in a solvent to yield a compound of Formula (XVII). The deprotection reaction is preferably carried out in the presence of a base selected from lithium hydroxide, sodium hydroxide, potassium hydroxide, magnesium hydroxide, sodium carbonate, potassium carbonate, cesium carbonate, magnesium carbonate, sodium bicarbonate, or potassium bicarbonate. More preferably, the base is sodium hydroxide. The deprotection reaction is preferably carried out in the presence of a solvent selected from water, methanol, ethanol, n-propanol, isopropanol, butanol, 2-methoxyethanol, 2-ethoxyethanol, or mixtures thereof. More preferably, the solvent is water, methanol or mixture thereof.

The reduction of a compound of Formula (XVII) is carried out in the presence of a reducing agent selected from sodium borohydride, sodium triacetoxyborohydride, lithium borohydride, diisobutylaluminium hydride, lithium aluminium hydride, triethylsilane, and palladium on carbon. More preferably, the reducing agent is palladium on carbon. Preferably, the reduction is carried out in the presence of hydrogen pressure. The hydrogen pressure can be in the range of about 10 pound per square inch (psi) to about 300 psi. Preferably, the reduction is carried out in the presence of a catalyst such as, for example, acetic acid. The reduction is preferably carried out in the presence of alcohol solvent such as, for example, methanol, ethanol, and isopropanol. More preferably, the solvent is methanol.

The reduction of a compound of Formula (XVI) is carried out in the presence of a reducing agent selected from sodium borohydride, sodium triacetoxyborohydride, lithium borohydride, diisobutylaluminium hydride, lithium aluminium hydride, triethylsilane, and palladium on carbon. More preferably, the reducing agent is triethylsilane. Preferably, the reduction is carried out in the presence of a catalyst such as, for example, aluminium chloride or boron trifluoride diethyl etherate. The reduction is preferably carried out in the presence of alcohol solvent such as, for example, methanol, ethanol, and isopropanol. More preferably, the solvent is methanol.

The deprotection of a compound of Formula (XVIa) is conducted in the presence of a base in a solvent to yield a compound of Formula (IX). The deprotection reaction is preferably carried out in the presence of a base selected from lithium hydroxide, sodium hydroxide, potassium hydroxide, magnesium hydroxide, sodium carbonate, potassium carbonate, cesium carbonate, magnesium carbonate, sodium bicarbonate, or potassium bicarbonate. More preferably, the base is sodium hydroxide. The deprotection reaction is preferably carried out in the presence of a solvent selected from water, methanol, ethanol, n-propanol, isopropanol, butanol, 2-methoxyethanol, 2-ethoxyethanol, or mixtures thereof. More preferably, the solvent is water, methanol or mixture thereof.

In yet another aspect of the present invention, the reaction of a compound of Formula (VI) with a compound of Formula (VIIa) is carried out in the presence of a base selected from lithium hydroxide, sodium hydroxide, potassium hydroxide, magnesium hydroxide, sodium carbonate, potassium carbonate, cesium carbonate, magnesium carbonate, sodium bicarbonate and potassium bicarbonate in a solvent to yield the compound of Formula (XVIII). The reaction is preferably carried out in the presence of a polar aprotic solvent such as, for example, N,N-dimethylformamide.

The reaction of a compound of Formula (VI) with a compound of Formula (VIIc) can be carried out at about 25° C. to about 150° C., optionally in the presence a catalyst selected from hydroquinone, iron catalyst, or copper catalyst such as copper (II) chloride, copper sulfate.

In a particular embodiment of the present invention, the compound of Formula (VIIa) or (VIIc), wherein $R^6$ is a group selected from mono or di-carboxylic acid, acid chloride, ester, nitrile, aldehyde, alcohol, amide, alkyl, alkenyl, alkynyl, alkyl halide, or keto group, which can eventually be converted to mono carboxylic acid, when $R^6$ is not mono carboxylic acid.

The conversion of a compound of Formula (XVIII) to a compound of Formula (VIII), when $R^6$ is not mono carboxylic acid, can be carried out by any conventional method.

The deprotection of a compound of Formula (VIII) is conducted with hydroxy deprotecting agent in a solvent to yield the substituted pyrazole compound of Formula (I). Preferably, the hydroxy deprotecting agent is, for example, palladium on carbon. The deprotection reaction is carried out in the presence of hydrogen pressure. The hydrogen pressure can be in the range of about 10 pound per square inch (psi) to about 300 psi. The hydroxy deprotection is preferably carried out in the presence of a solvent selected from methyl acetate, ethyl acetate, n-propyl acetate, isopropyl acetate, n-butyl acetate, methanol, ethanol, n-propanol, isopropanol, butanol, 2-methoxyethanol and 2-ethoxyethanol. More preferably, the solvent is methanol or ethyl acetate.

The reaction of treating ester of 3-{4-[(7-hydroxy-6-methyl-indan-4-yl)methyl]-3,5-dimethyl-1H-pyrazol-1-yl}-propanoic acid with acid selected from mineral acid or organic acid or a mixture thereof is preferably carried out at about 30° C. to about 120° C.

The mineral acid is preferably selected from hydrochloric acid, hydrobromic acid, sulfuric acid, nitric acid, and phosphoric acid. More preferably, the mineral acid is hydrochloric acid. The organic acid is preferably acetic acid.

In one particular aspect of the present invention, the condensation of a compound of Formula (XIX) with a compound of Formula (XX) is carried out in the presence of a condensing agent optionally in combination with acid catalyst in a solvent to yield a compound of Formula (XIIIa). The condensing agent is preferably selected from formaldehyde, paraformaldehyde, 1,3,5-trioxane, or mixtures thereof. More preferably, the condensing agent is paraformaldehyde. The acid catalyst is preferably selected from hydrochloric acid, sulphuric acid, p-toluenesulfonic acid, zinc chloride, or tin(II)chloride. The solvent is preferably selected from acetic acid, N,N-dimethylformamide, N,N-dimethylacetamide, dimethylsulphoxide, acetonitrile, N-methylpyrrolidone, cyclohexane, toluene, xylene or benzene. More preferably, the solvent is acetic acid, cyclohexane, toluene, or xylene. The condensation reaction is preferably carried out at about 30° C. to about 150° C. More preferably, the condensation reaction is carried out at about 40° C. to about 140° C.

The condensation of a compound of Formula (XIX) with a compound of Formula (XX) in the presence of a condensing agent is carried out by either combining a compound of Formula (XIX), compound of Formula (XX), and a condensing agent together in one pot, or by combining a compound of Formula (XIX) with a condensing agent and then reacting the resultant product with a compound of Formula (XX) to provide a compound of Formula (XIIIa) or a compound of Formula (I). Preferably, the condensation reaction is carried out by combining a compound of Formula (XIX) with a condensing agent and then reacting the resulted product with a compound of Formula (XX) to provide a compound of Formula (XIIIa) or a compound of Formula (I).

The hydroxy deprotection of a compound of Formula (VIIIa), wherein $Pg^1$ is benzyl, is carried with hydroxy deprotecting agent in a solvent to yield the substituted pyrazole compound of Formula (I). Preferably, the hydroxy deprotecting agent is, for example, palladium on carbon. The deprotection reaction is preferably carried out in the presence of hydrogen pressure. The hydrogen pressure can be in the range of about 10 pound per square inch (psi) to about 300 psi. The hydroxy deprotection is preferably carried out in the presence of a solvent selected from methyl acetate, ethyl acetate, n-propyl acetate, isopropyl acetate, n-butyl acetate, methanol, ethanol, n-propanol, isopropanol, butanol, 2-methoxyethanol, and 2-ethoxyethanol. More preferably, the solvent is methanol or ethyl acetate.

The hydrolysis of a compound of Formula (VIIIa), wherein $R^4$ is $C_{1-10}$ alkyl, is carried out by ester hydrolysis in the presence of a base to yield the substituted pyrazole compound of Formula (I). The ester hydrolysis is preferably carried out by reacting a compound of Formula (VIIIa), wherein $R^4$ is $C_{1-10}$ alkyl, with a base selected from lithium hydroxide, sodium hydroxide, potassium hydroxide, magnesium hydroxide, sodium carbonate, potassium carbonate, cesium carbonate, magnesium carbonate, sodium bicarbonate, and potassium bicarbonate, in a solvent to yield the substituted pyrazole compound of Formula (I). More preferably, the base is sodium hydroxide. The reaction is preferably carried out in a solvent such as water, tetrahydrofuran or mixture thereof.

The compound of Formula (XIX) is prepared by condensing a compound of Formula (XXI) with a compound of Formula (VII) in the presence of a base selected from lithium hydroxide, sodium hydroxide, potassium hydroxide, magnesium hydroxide, sodium carbonate, potassium carbonate, cesium carbonate, magnesium carbonate, sodium bicarbonate, and potassium bicarbonate, in a solvent to yield a compound of Formula (XIX). More preferably, the base is cesium carbonate. The reaction is preferably carried out in a solvent such as N,N-dimethylformamide, N,N-dimethylacetamide, dimethylsulphoxide, acetonitrile, and N-methylpyrrolidone. More preferably, the solvent is N,N-dimethylformamide. The condensation of a compound of Formula (XXI) with a compound of Formula (VII) is carried out in the presence of phase-transfer catalyst selected from quaternary ammonium salts, phosphonium salts, crown ethers, polyethylene glycols and combinations thereof. Preferably the reaction is carried out in the presence of quaternary ammonium salt or crown ether. More preferably, the reaction is carried out in the presence of crown ether.

In another particular aspect of the present invention, the condensation of a compound of Formula (XX) with a compound of Formula (XXII) is carried out in the presence of a condensing agent optionally in combination with acid catalyst in a solvent to yield a compound of Formula (VIb). The condensing agent is preferably selected from formaldehyde, paraformaldehyde, 1,3,5-trioxane, or mixtures thereof. More preferably, the condensing agent is paraformaldehyde. The acid catalyst is preferably selected from hydrochloric acid, sulphuric acid, p-toluenesulfonic acid, zinc chloride, or tin(II)chloride. The solvent is preferably selected from acetic acid, N,N-dimethylformamide, N,N-dimethylacetamide, dimethylsulphoxide, acetonitrile, N-methylpyrrolidone, cyclohexane, toluene, xylene, or benzene. More preferably, the solvent is acetic acid, cyclohexane, toluene or xylene. The condensation reaction is preferably carried out at about 30° C. to about 150° C. More preferably, the condensation reaction is carried out at about 40° C. to about 140° C.

The cyclization of a compound of Formula (VIb) is carried out by treating a compound of Formula (VIb) with hydrazine in the presence of an acid catalyst in a solvent to yield the compound of Formula (VIc). The acid catalyst is preferably selected from acetic acid or trifluoroacetic acid. More preferably, the acid catalyst is acetic acid. The cyclization of a compound of Formula (VIb) with hydrazine in a solvent is preferably carried out at about 20° C. to about 90° C. More preferably, the reaction is carried out at about 60° C. to about 85° C. The reaction of a compound of Formula (VIb) with hydrazine is preferably carried out in the presence of a solvent selected from methanol, ethanol, n-propanol, isopropanol, butanol, 2-methoxyethanol, and 2-ethoxyethanol. More preferably, the solvent is isopropanol.

The compound of Formula (VIc) is then reacted with a compound of Formula (VII) in the presence of a base selected from lithium hydroxide, sodium hydroxide, potassium hydroxide, magnesium hydroxide, sodium carbonate, potassium carbonate, cesium carbonate, magnesium carbonate, sodium bicarbonate, and potassium bicarbonate in a solvent to yield the substituted pyrazole compound of Formula (I). More preferably, the base is cesium carbonate. The reaction is preferably carried out in the presence of a polar aprotic solvent such as, for example, N,N-dimethylformamide.

The substituted pyrazole compound of Formula (I) is also prepared by reacting a compound of Formula (Vic) with ethyl acrylate optionally in the presence of a catalyst selected from hydroquinone, iron catalyst, or copper catalyst such as copper (II) chloride, copper sulfate. The reaction of a compound of Formula (Vic) with ethyl acrylate is preferably carried out at about 30° C. to about 120° C. More preferably, the reaction is carried out at about 60° C. to about 110° C.

The hydroxy deprotection of a compound of Formula (VIIIa), wherein $Pg^1$ is methyl, is carried with hydroxy deprotecting agent in a solvent to yield substituted pyrazole compound of Formula (I). Preferably, the hydroxy deprotecting agent is, for example, boron tribromide. The hydroxy deprotection is preferably carried out in the presence of a solvent selected from methyl acetate, ethyl acetate, n-propyl acetate, isopropyl acetate, n-butyl acetate, dichloromethane, chloroform, and 1,2-dichloroethane. More preferably, the solvent is dichloromethane or ethyl acetate.

The condensation of a compound of Formula (XX) with a compound of Formula (XXIII) can be carried out in the presence of a condensing agent optionally in combination with acid catalyst in a solvent to yield a compound of Formula (XXIV). The condensing agent is preferably selected from formaldehyde, paraformaldehyde, 1,3,5-trioxane, or mixtures thereof. More preferably, the condensing agent is paraformaldehyde. The acid catalyst is preferably selected from hydrochloric acid, sulphuric acid, p-toluenesulfonic acid, zinc chloride, or tin(II) chloride. The solvent is preferably selected from acetic acid, N,N-dimethylformamide, N,N-dimethylacetamide, dimethylsulphoxide, acetonitrile, N-methylpyrrolidone, cyclohexane, toluene, xylene, or benzene. More preferably, the solvent is acetic acid, cyclohexane, toluene, or xylene. The condensation reaction is preferably carried out at about 30° C. to about 150° C. More preferably, the condensation reaction is carried out at about 40° C. to about 140° C.

The deprotection of a compound of Formula (XXIV) can be carried out with amino deprotecting agent in solvent to yield a compound of Formula (Vic).

In another particular aspect of the present invention, the condensation of a compound of Formula (XXV) with a compound of Formula (XX) is carried out in the presence of a condensing agent optionally in combination with acid catalyst in a solvent to yield a compound of Formula (XVIIIa). The condensing agent is preferably selected from formaldehyde, paraformaldehyde, 1,3,5-trioxane, or mixtures thereof. More preferably, the condensing agent is paraformaldehyde. The acid catalyst is preferably selected from hydrochloric acid, sulphuric acid, p-toluenesulfonic acid, zinc chloride, or tin(II) chloride. The solvent is preferably selected from acetic acid, N,N-dimethylformamide, N,N-dimethylacetamide, dimethylsulphoxide, acetonitrile, N-methylpyrrolidone, cyclohexane, toluene, xylene, or benzene. More preferably, the solvent is acetic acid, cyclohexane, toluene or xylene. The condensation reaction is preferably carried out at about 30° C. to about 150° C. More preferably, the condensation reaction is carried out at about 40° C. to about 140° C.

In a particular embodiment of the present invention, the compound of Formula (XXV), wherein $R^6$ is a group which can be converted to carboxylic acid. Such group is selected from di-carboxylic acid, acid chloride, ester, nitrile, aldehyde, alcohol, amide, alkyl, alkenyl, alkynyl, alkyl halide, or keto group.

The conversion of a compound of Formula (XVIIIa), when $R^6$ is not mono carboxylic acid, to a compound of Formula (VIIIa) can be carried out by any conventional method.

The compound of Formula (XXV) can be prepared by condensing a compound of Formula (XXI) with a compound of Formula (VIIa) in the presence of a base selected from lithium hydroxide, sodium hydroxide, potassium hydroxide, magnesium hydroxide, sodium carbonate, potassium carbonate, cesium carbonate, magnesium carbonate, sodium bicarbonate, and potassium bicarbonate, in a solvent to yield a compound of Formula (XXV). More preferably, the base is cesium carbonate. The reaction is preferably carried out in a solvent such as N,N-dimethylformamide, N,N-dimethylacetamide, dimethylsulphoxide, acetonitrile, and N-methylpyrrolidone. More preferably, the solvent is N,N-dimethylformamide.

In a specific embodiment of the present invention, the substituted pyrazole compounds of Formula (I) synthesized by the present invention can be used for treating disease condition associated with inappropriate thyroid hormone activity selected from obesity, insulin resistance, dyslipidemia, metabolic syndrome, type II diabetes, replacement therapy in elderly subjects with hypothyroidism, depression, cardiovascular diseases and skin disorders by administering therapeutically effective amount of substituted pyrazole compounds of Formula (I) and pharmaceutically acceptable carriers and/or excipients.

Crystalline Form-$T_{15-1}$:

The crystalline Form-$T_{15-1}$ is produced by suspending 3-{4-[(7-hydroxy-6-methyl-indan-4-yl)methyl]-3,5-dimethyl-1H-pyrazol-1-yl}-propanoic acid or its ester in water and then treating with aqueous base. Subsequently, the reaction mixture is acidified with aqueous acid to yield crystalline Form-$T_{15-1}$ of 3-{4-[(7-hydroxy-6-methyl-indan-4-yl)methyl]-3,5-dimethyl-1H-pyrazol-1-yl}-propanoic acid. Preferably, the base is selected from sodium carbonate, potassium carbonate, lithium carbonate sodium bicarbonate, potassium bicarbonate sodium hydroxide, potassium hydroxide, lithium hydroxide. More preferably, the base is sodium hydroxide. Preferably, the acid is hydrochloric acid.

The process of treating 3-{4-[(7-hydroxy-6-methyl-indan-4-yl)methyl]-3,5-dimethyl-1H-pyrazol-1-yl}-propanoic acid with aqueous base is preferably carried out at about 10° C. to about 50° C. The process of acidifying with aqueous acid is more preferably carried out at about 25° C. to about 35° C.

The crystalline Form-$T_{15-1}$ can also be produced by treating 3-(4-{[7-(Pg$^1$-oxy)-6-methyl-indan-4-yl]methyl}-3,5-dimethyl-1H-pyrazol-1-yl)propanoic acid or its ester, wherein Pg$^1$ is hydroxy protecting group, for example, benzyl; with a suitable hydroxy deprotecting agent in presence of aqueous base. Subsequently, the reaction mixture is acidified with aqueous acid to yield crystalline Form-$T_{15-1}$ of 3-{4-[(7-hydroxy-6-methyl-indan-4-yl)methyl]-3,5-dimethyl-1H-pyrazol-1-yl}-propanoic acid. Preferably, the suitable hydroxy deprotecting agent is, for example, Palladium on carbon. Preferably, the base is selected from sodium carbonate, potassium carbonate, lithium carbonate sodium bicarbonate, potassium bicarbonate sodium hydroxide, potassium hydroxide, lithium hydroxide. More preferably, the base is sodium hydroxide. Preferably, the acid is hydrochloric acid.

The deprotection reaction is preferably carried out in the presence of hydrogen pressure. The hydrogen pressure can be in the range of about 10 pound per square inch (psi) to about 300 psi.

The process of treating 3-(4-{[7-(Pg$^1$-oxy)-6-methyl-indan-4-yl]methyl}-3,5-dimethyl-1H-pyrazol-1-yl)propanoic acid with a suitable hydroxy deprotecting agent in presence of aqueous base is preferably carried out at about 0° C. to 80° C. More preferably, the process is carried out at about 40° C. to about 60° C.

The process of acidifying with aqueous acid is preferably carried out at about 10° C. to 50° C. More preferably, the process is carried out at about 20° C. to about 40° C. The isolated crystalline Form-$T_{15-1}$ of 3-{4-[(7-hydroxy-6-methyl-indan-4-yl)methyl]-3,5-dimethyl-1H-pyrazol-1-yl}-propanoic acid is preferably made slurry in ethyl acetate and filtered to remove excess water.

The crystalline Form-$T_{15-1}$ is characterized by several analytical techniques including X-ray powder diffraction (XRPD), Differential scanning calorimetry (DSC), and Thermogravimetric analysis (TGA).

The X-ray powder diffraction pattern of crystal Form-$T_{15-1}$ is shown in FIG. 1. The peak assignments corresponding to the diffraction pattern for crystalline Form-$T_{15-1}$ and their relative intensities are listed in Table 1.

TABLE 1

| Angle 2-Theta° | Relative Intensity (%) | Angle 2-Theta° | Relative Intensity (%) | Angle 2-Theta° | Relative Intensity (%) |
|---|---|---|---|---|---|
| 3.7 | 1.2 | 19.2 | 16.0 | 27.2 | 11.3 |
| 6.1 | 8.5 | 19.7 | 34.8 | 27.6 | 19.4 |
| 7.4 | 24.3 | 20.2 | 45.1 | 29.1 | 7.1 |
| 10.7 | 35.4 | 20.7 | 5.1 | 30.8 | 10.6 |
| 11.9 | 36.9 | 21.4 | 30.1 | 31.6 | 13.0 |
| 12.3 | 100.0 | 21.5 | 26.1 | 32.1 | 10.9 |
| 12.7 | 66.2 | 22.1 | 46.3 | 32.5 | 10.6 |
| 13.7 | 3.0 | 22.9 | 44.8 | 33.0 | 8.2 |
| 14.4 | 9.2 | 23.4 | 23.1 | 33.9 | 1.3 |
| 14.9 | 27.8 | 24.6 | 27.8 | 35.1 | 2.4 |
| 15.9 | 7.7 | 24.9 | 35.6 | 36.3 | 3.0 |
| 16.4 | 14.1 | 25.7 | 31.0 | 36.9 | 3.4 |
| 17.1 | 9.2 | 26.2 | 31.1 | | |
| 18.7 | 25.8 | 26.9 | 16.6 | | |

Figure 2:
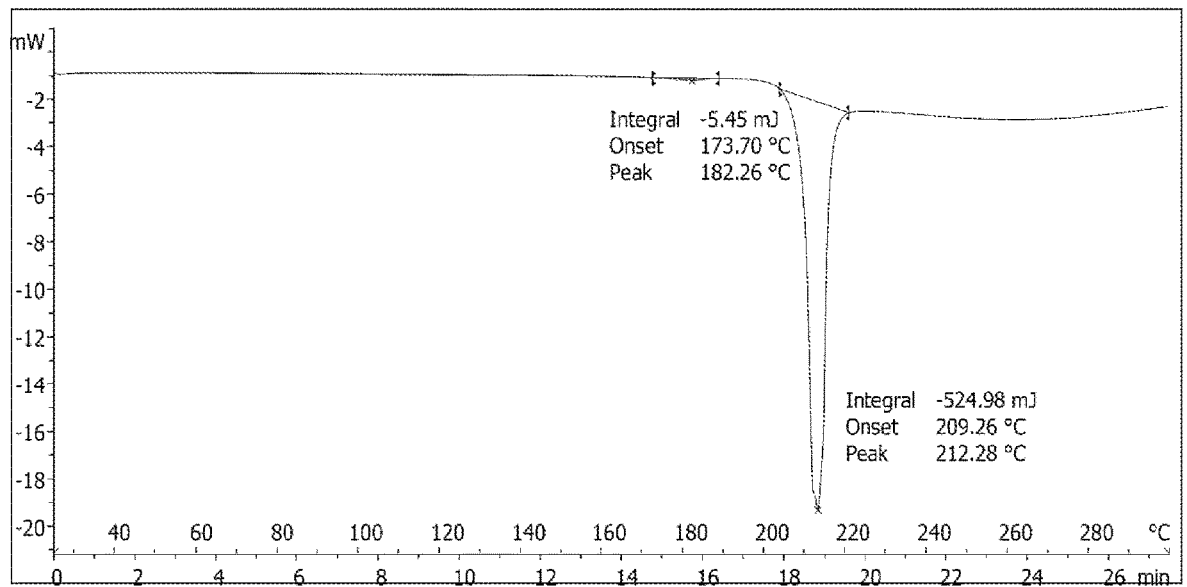
FIG. 2 illustrates a Differential Scanning calorimetry (DSC) thermogram of the crystalline Form-$T_{15-1}$.
Figure 3:
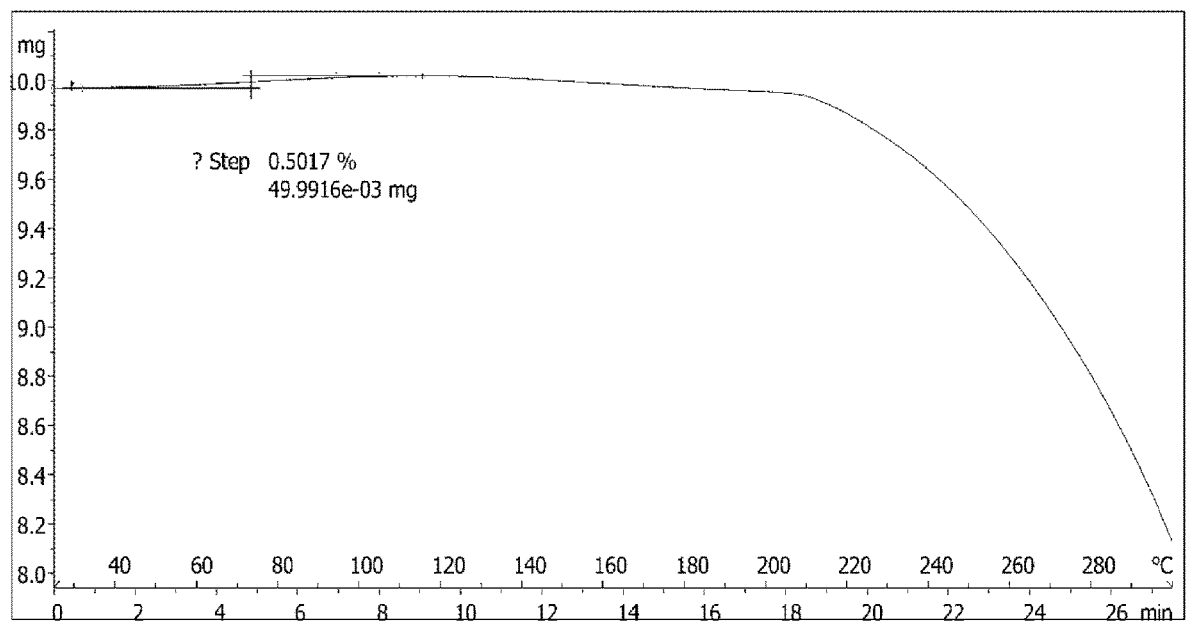
FIG. 3 illustrates a Thermogravimetric analysis (TGA) curve of the crystalline Form-$T_{15-1}$.

Thermogravimetric graph of crystalline Form-$T_{15-1}$ is shown in FIG. 3. A weight loss of about 0.5% observed between the temperature range of 30° C. to 110° C., as determined by TGA. The graph of differential scanning calorimetry of crystalline Form-$T_{15-1}$, performed at a rate of change of 10° C./min, is shown in FIG. 2, wherein an endothermic peak is observed at about 212° C.

Crystalline Form-$T_{15-2}$:

The crystalline Form-$T_{15-2}$ is produced by suspending 3-{4-[(7-hydroxy-6-methyl-indan-4-yl)methyl]-3,5-dimethyl-1H-pyrazol-1-yl}-propanoic acid or its ester in water and then treated with aqueous base. Subsequently, the reaction mixture is then acidified with aqueous acid at below 10° C. to yield crystalline Form-Tis-2 of 3-{4-[(7-hydroxy-6-methyl-indan-4-yl)methyl]-3,5-dimethyl-1H-pyrazol-1-yl}-propanoic acid. Preferably, the base is selected from sodium carbonate, potassium carbonate, lithium carbonate, sodium bicarbonate, potassium bicarbonate, sodium hydroxide, potassium hydroxide, or lithium hydroxide. More preferably, the base is sodium hydroxide. Preferably, the acid is hydrochloric acid.

The process of treating 3-{4-[(7-hydroxy-6-methyl-indan-4-yl)methyl]-3,5-dimethyl-1H-pyrazol-1-yl}-propanoic acid with aqueous base is preferably carried out at about 0° C. to about 50° C.

The isolated crystalline Form-$T_{15-2}$ of 3-{4-[(7-hydroxy-6-methyl-indan-4-yl)methyl]-3,5-dimethyl-1H-pyrazol-1-yl}-propanoic acid is preferably dried in a vacuum tray dryer to remove excess water.

The crystalline Form-$T_{15-2}$ is characterized by several analytical techniques including X-ray powder diffraction (XRPD), Differential scanning calorimetry (DSC), and Thermogravimetric analysis (TGA).

Figure 4:
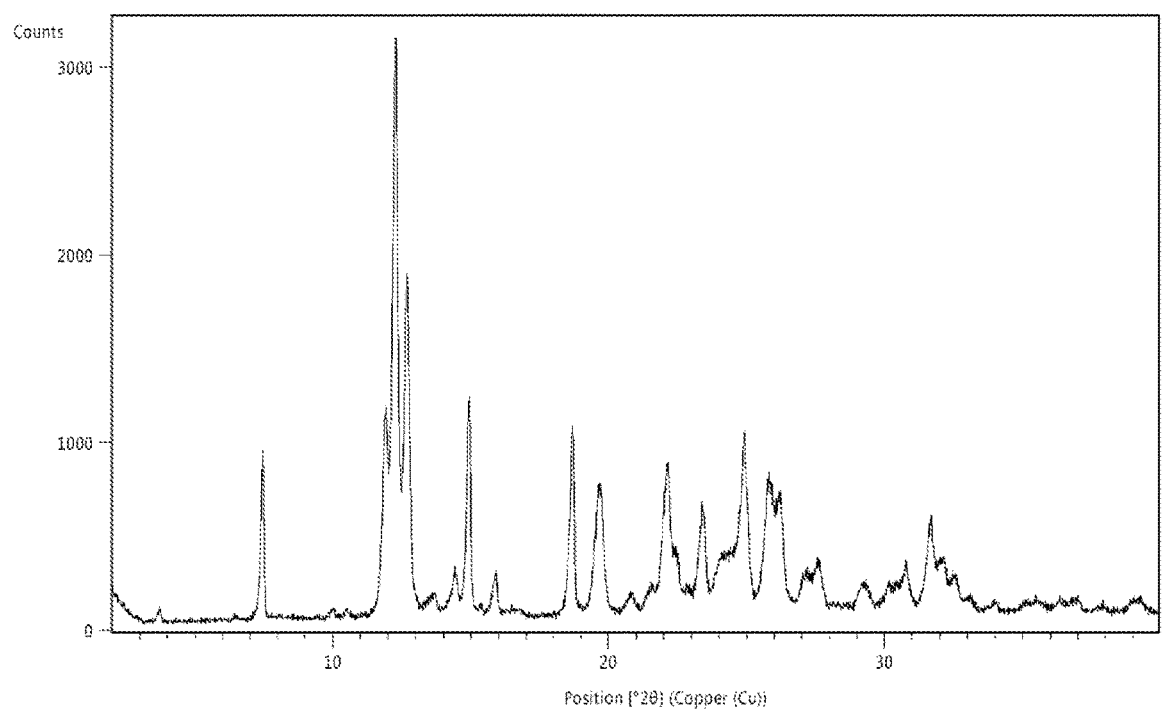
FIG. 4 illustrates an XRPD pattern of the crystalline Form-$T_{15-2}$.

The X-ray powder diffraction pattern of crystal Form-$T_{15-2}$ is shown in FIG. 4.

Figure 5:
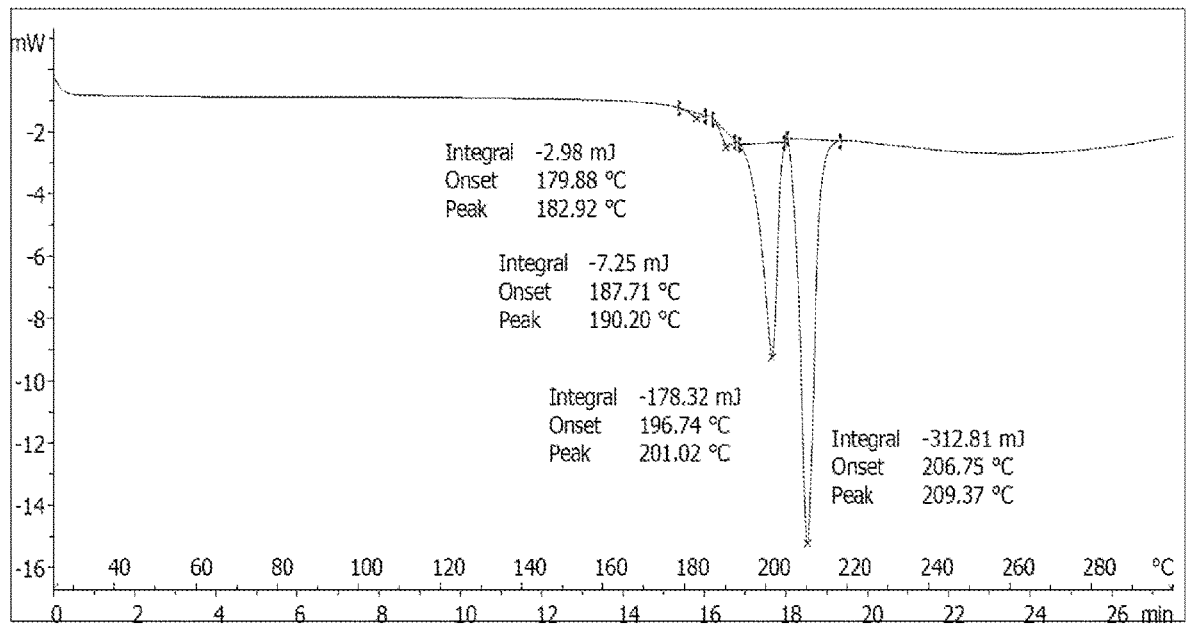
FIG. 5 illustrates a DSC thermogram of the crystalline Form-$T_{15-2}$.
Figure 6:
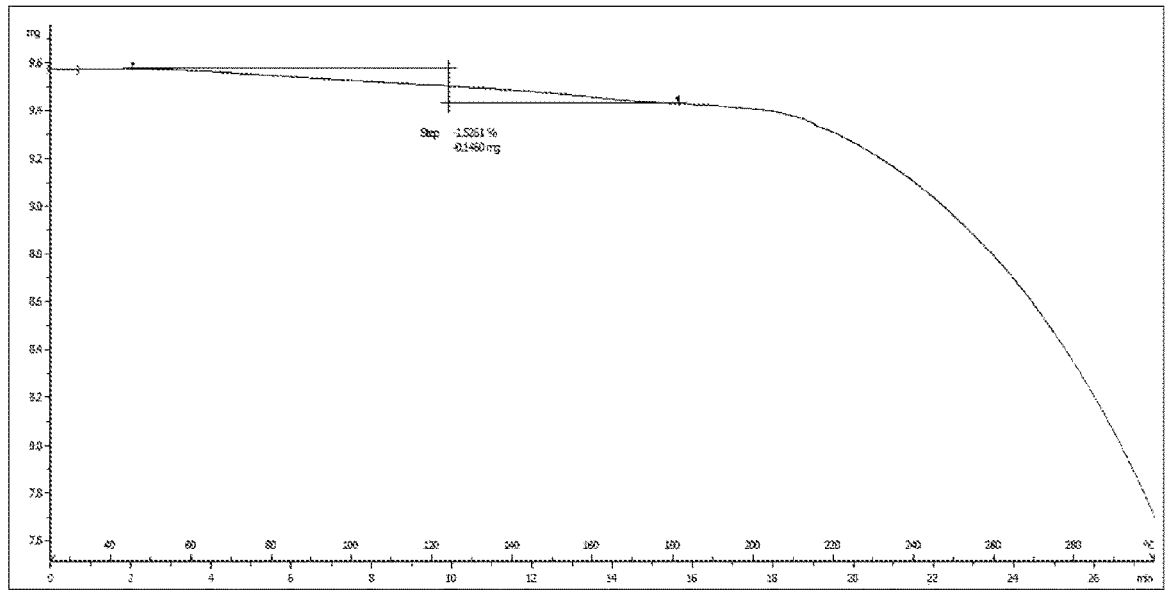
FIG. 6 illustrates a TGA curve of the crystalline Form-$T_{15-2}$.

The crystalline Form-$T_{15-2}$ is also characterized by a weight loss of about 1.5% observed between the temperature range of 45° C. to 180° C., as determined by TGA curve which is shown in FIG. 6. The crystalline Form-$T_{15-2}$ is further characterized by endothermic peaks are observed at about 201° C. and about 209° C., as determined by DSC shown in FIG. 5.

Crystalline Form-$T_{15-3}$:

The crystalline Form-$T_{15-3}$ is produced by treating ester of 3-{4-[(7-hydroxy-6-methyl-indan-4-yl)methyl]-3,5-dimethyl-1H-pyrazol-1-yl}-propanoic acid with acid to yield crystalline Form-$T_{15-3}$ of 3-{4-[(7-hydroxy-6-methyl-indan-4-yl)methyl]-3,5-dimethyl-1H-pyrazol-1-yl}-propanoic acid.

The acid is selected from mineral acid or organic acid or a combination thereof. The mineral acid is preferably selected from hydrochloric acid, hydrobromic acid, sulfuric acid, nitric acid, and phosphoric acid. More preferably, the mineral acid is hydrochloric acid. The organic acid is preferably acetic acid.

The reaction of treating ester of 3-{4-[(7-hydroxy-6-methyl-indan-4-yl)methyl]-3,5-dimethyl-1H-pyrazol-1-yl}-propanoic acid with mineral acid, organic acid, or its mixture thereof is preferably carried out at about 30° C. to about 120° C.

The crystalline Form-$T_{15-3}$ is also produced by suspending 3-{4-[(7-hydroxy-6-methyl-indan-4-yl)methyl]-3,5-dimethyl-1H-pyrazol-1-yl}-propanoic acid or its ester in organic solvent, or in a mixture of organic solvent and water, and then treating with aqueous base. Subsequently, the reaction mixture is acidified with aqueous acid to yield crystalline Form-$T_{15-3}$ of 3-{4-[(7-hydroxy-6-methyl-indan-4-yl)methyl]-3,5-dimethyl-1H-pyrazol-1-yl}-propanoic acid.

The organic solvent is preferably selected from ester solvents, alcohol solvents, hydrocarbon solvents, halogenated hydrocarbon solvents, ketone solvents, ether solvents, polar aprotic solvents, or mixtures thereof.

Preferably, the base is selected from sodium carbonate, potassium carbonate, lithium carbonate sodium bicarbonate, potassium bicarbonate sodium hydroxide, potassium hydroxide, lithium hydroxide. More preferably, the base is sodium hydroxide. Preferably, the acid is hydrochloric acid.

The processes of both treating 3-{4-[(7-hydroxy-6-methyl-indan-4-yl)methyl]-3,5-dimethyl-1H-pyrazol-1-yl}-propanoic acid with aqueous base and acidifying with acid are preferably carried out at about 0° C. to 150° C. More preferably, these processes are carried out at about 10° C. to about 120° C.

The isolated crystalline Form-$T_{15-3}$ of 3-{4-[(7-hydroxy-6-methyl-indan-4-yl)methyl]-3,5-dimethyl-1H-pyrazol-1-yl}-propanoic acid is preferably made slurry in ethyl acetate and filtered to remove excess water.

The crystalline Form-$T_{15-3}$ can also be produced by treating 3-(4-{[7-(Pg$^1$-oxy)-6-methyl-indan-4-yl]methyl}-3,5-dimethyl-1H-pyrazol-1-yl)propanoic acid, wherein Pg$^1$ is hydroxy protecting group, for example, benzyl; with a suitable hydroxy deprotecting agent in organic solvent or in a mixture of organic solvent and water. Preferably, the suitable hydroxy deprotecting agent is, for example, Palladium on carbon.

The deprotection reaction is preferably carried out in the presence of hydrogen pressure. The hydrogen pressure can be in the range of about 10 pound per square inch (psi) to about 300 psi.

The organic solvent is preferably selected from ester solvents, alcohol solvents, hydrocarbon solvents, halogenated hydrocarbon solvents, ketone solvents, ether solvents, polar aprotic solvents, or mixtures thereof.

The crystalline Form-$T_{15-3}$ can also be produced by combining 3-{4-[(7-hydroxy-6-methyl-indan-4-yl)methyl]-3,5-dimethyl-1H-pyrazol-1-yl}propanoic acid with organic solvent and optionally adding anti-solvent.

The organic solvent is preferably selected from ester solvents, alcohol solvents, halogenated hydrocarbon solvents, ketone solvents, ether solvents, polar aprotic solvents, or mixtures thereof.

The anti-solvent is preferably selected from water, hydrocarbon solvents, or mixture thereof.

The processes of combining 3-{4-[(7-hydroxy-6-methyl-indan-4-yl)methyl]-3,5-dimethyl-1H-pyrazol-1-yl}propanoic acid with organic solvent and optionally adding anti-solvent are carried out at about 0° C. to reflux temperature of the mixture.

Figure 7:
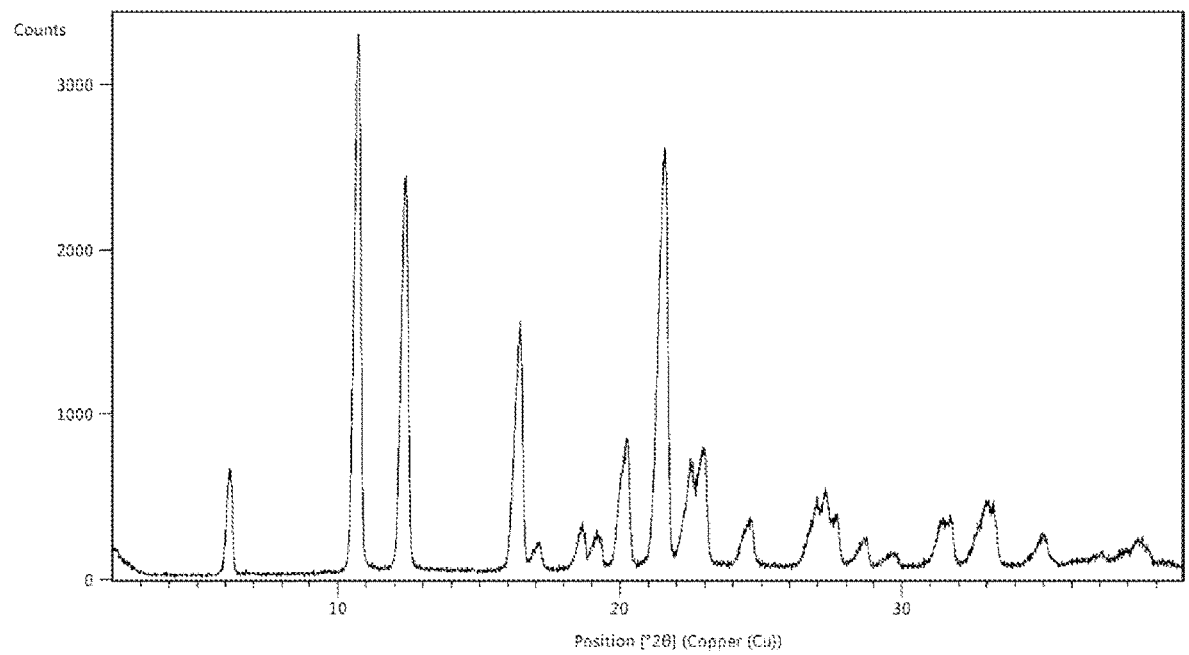
FIG. 7 illustrates an XRPD pattern of the crystalline Form-$T_{15-3}$.

The X-ray powder diffraction pattern of crystalline Form-$T_{15-3}$ is shown in FIG. 7. The peak assignments corresponding to the diffraction pattern for crystalline Form-$T_{15-3}$ and their relative intensities are listed in Table 2.

TABLE 2

| Angle 2-Theta° | Relative Intensity (%) | Angle 2-Theta° | Relative Intensity (%) | Angle 2-Theta° | Relative Intensity (%) |
|---|---|---|---|---|---|
| 2.0 | 4.8 | 19.3 | 5.9 | 27.2 | 15.1 |
| 6.1 | 19.1 | 19.9 | 16.3 | 27.7 | 9.9 |
| 6.2 | 17.4 | 20.2 | 23.6 | 28.7 | 5.9 |
| 10.5 | 62.5 | 21.6 | 72.8 | 29.7 | 3.0 |
| 10.7 | 100.0 | 22.5 | 20.5 | 31.3 | 8.8 |
| 12.4 | 69.3 | 23.0 | 21.7 | 31.7 | 9.1 |
| 16.5 | 36.3 | 24.3 | 6.4 | 33.0 | 12.9 |
| 17.1 | 4.9 | 24.6 | 8.7 | 33.2 | 11.4 |
| 18.7 | 7.5 | 26.9 | 13.0 | 35.0 | 5.8 |
| 37.0 | 3.3 | 38.6 | 4.2 | | |
| 38.3 | 5.7 | | | | |

Figure 8:
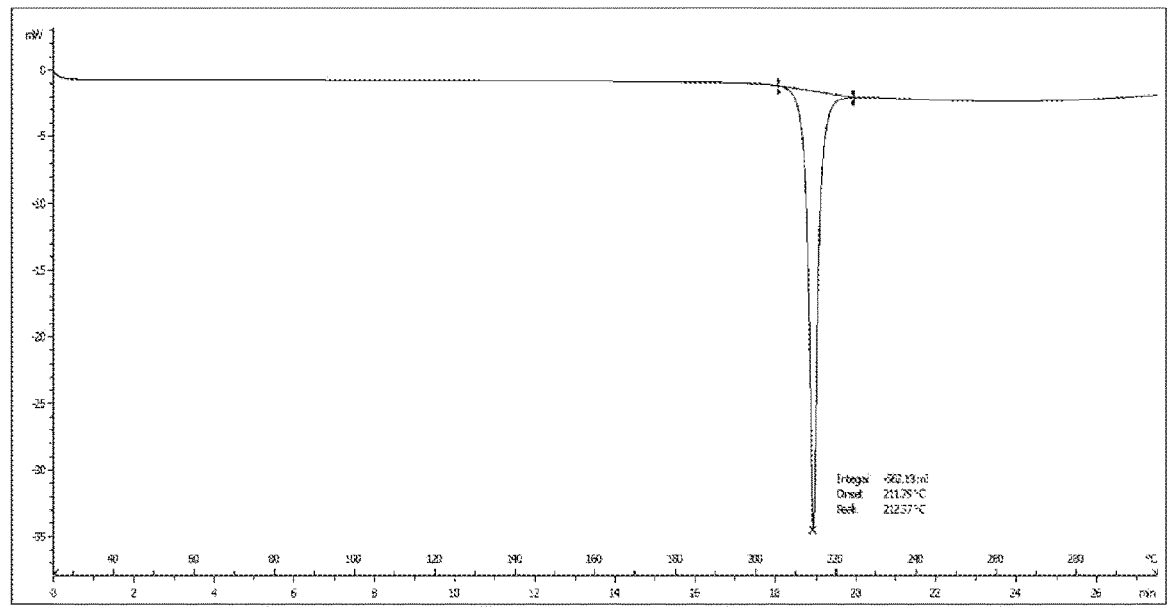
FIG. 8 illustrates a DSC thermogram of the crystalline Form-$T_{15-3}$.
Figure 9:
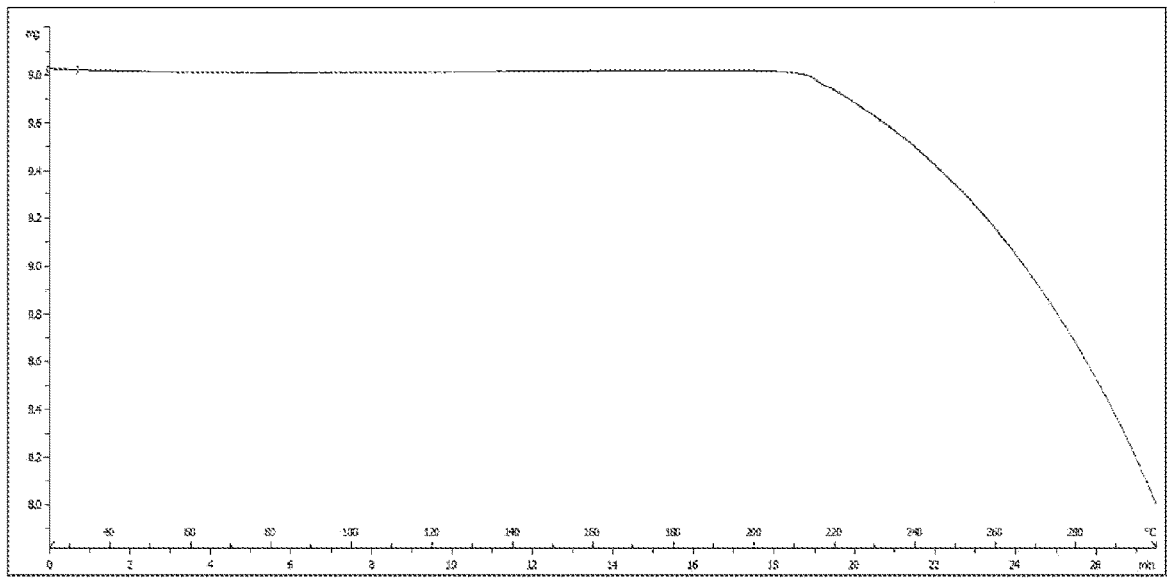
FIG. 9 illustrates a TGA curve of the crystalline Form-$T_{15-3}$.

The crystalline Form-$T_{15-3}$ does not show any weight loss as determined by TGA curve which is shown in FIG. 9. The crystalline Form-$T_{15-3}$ is further characterized by endothermic peak observed at about 212° C., as determined by DSC and its thermogram is shown in FIG. 8.

In another embodiment, the crystalline Form-$T_{15-3}$ of 3-{4-[(7-hydroxy-6-methyl-indan-4-yl)methyl]-3,5-dimethyl-1H-pyrazol-1-yl}-propanoic acid is also prepared by heating crystalline Form-$T_{15-2}$ to 200° C. and cooling to 20° C. to 40° C.

In another embodiment, the crystalline Form-$T_{15-3}$ of 3-{4-[(7-hydroxy-6-methyl-indan-4-yl)methyl]-3,5-dimethyl-1H-pyrazol-1-yl}-propanoic acid is also prepared by suspending crystalline Form-$T_{15-1}$ in organic solvent, heating and cooling to 20° C. to 40° C.

The suspension of crystalline Form-$T_{15-1}$ of 3-{4-[(7-hydroxy-6-methyl-indan-4-yl)methyl]-3,5-dimethyl-1H-pyrazol-1-yl}-propanoic acid in organic solvent is preferably heated to the reflux temperature of the organic solvent and then cooled to 20° C. to 40° C.

The organic solvent is preferably selected from ester solvents, alcohol solvents, hydrocarbon solvents, halogenated hydrocarbon solvents, ketone solvents, ether solvents, polar aprotic solvents, or mixtures thereof.

Crystalline Form-$T_{15-4}$:

The crystalline Form-$T_{15-4}$ is produced by treating 3-{4-[(7-hydroxy-6-methyl-indan-4-yl)methyl]-3,5-dimethyl-1H-pyrazol-1-yl}propanoic acid or its ester with aqueous base, acidifying with acid at below 10° C., isolating the solid, and air drying to provide crystalline Form-$T_{15\text{-}4}$ of 3-{4-[(7-hydroxy-6-methyl-indan-4-yl)methyl]-3,5-dimethyl-1H-pyrazol-1-yl}propanoic acid. Preferably, the base is selected from sodium carbonate, potassium carbonate, lithium carbonate sodium bicarbonate, potassium bicarbonate sodium hydroxide, potassium hydroxide, lithium hydroxide. More preferably, the base is sodium hydroxide. Preferably, the acid is hydrochloric acid.

The process of treating 3-{4-[(7-hydroxy-6-methyl-indan-4-yl)methyl]-3,5-dimethyl-1H-pyrazol-1-yl}-propanoic acid with aqueous acid or base is preferably carried out at about 0° C. to about 40° C.

In one embodiment, the crystalline Form-$T_{15\text{-}4}$ of 3-{4-[(7-hydroxy-6-methyl-indan-4-yl)methyl]-3,5-dimethyl-1H-pyrazol-1-yl}-propanoic acid is hydrate having water content of about 4.5% to about 5.5%, as measured by Karl Fischer method.

Figure 10:
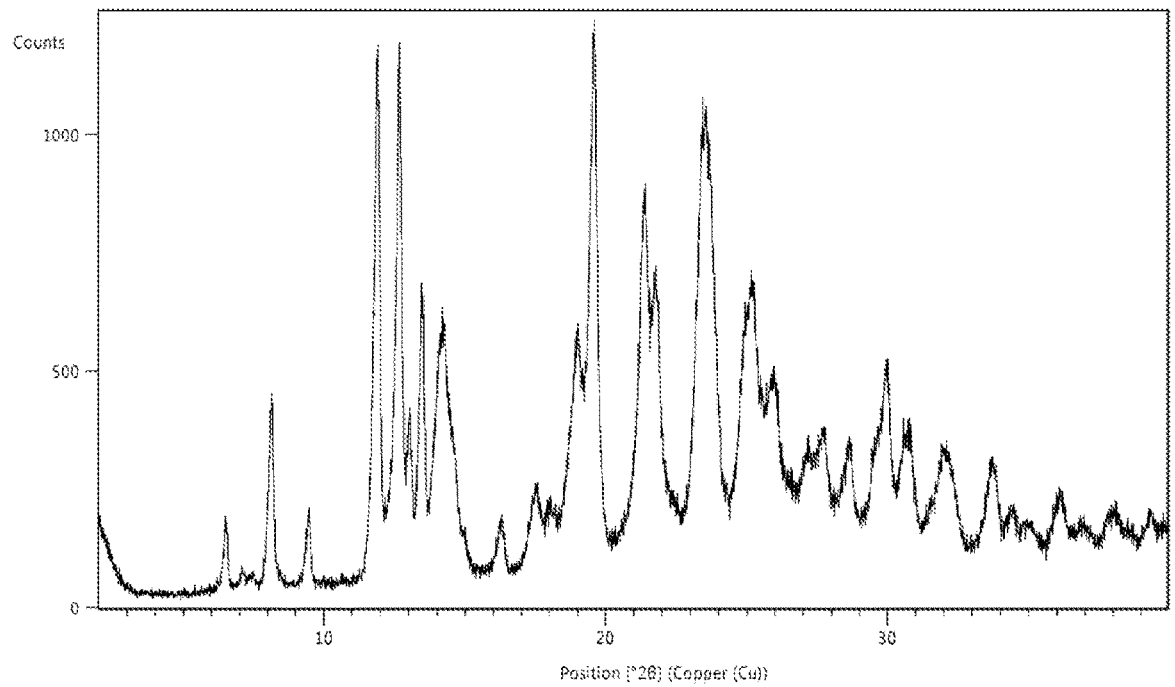
FIG. 10 illustrates an XRPD pattern of the crystalline Form-$T_{15-4}$.

The X-ray powder diffraction pattern of crystalline Form-$T_{15\text{-}4}$ is shown in FIG. 10.

Figure 11:
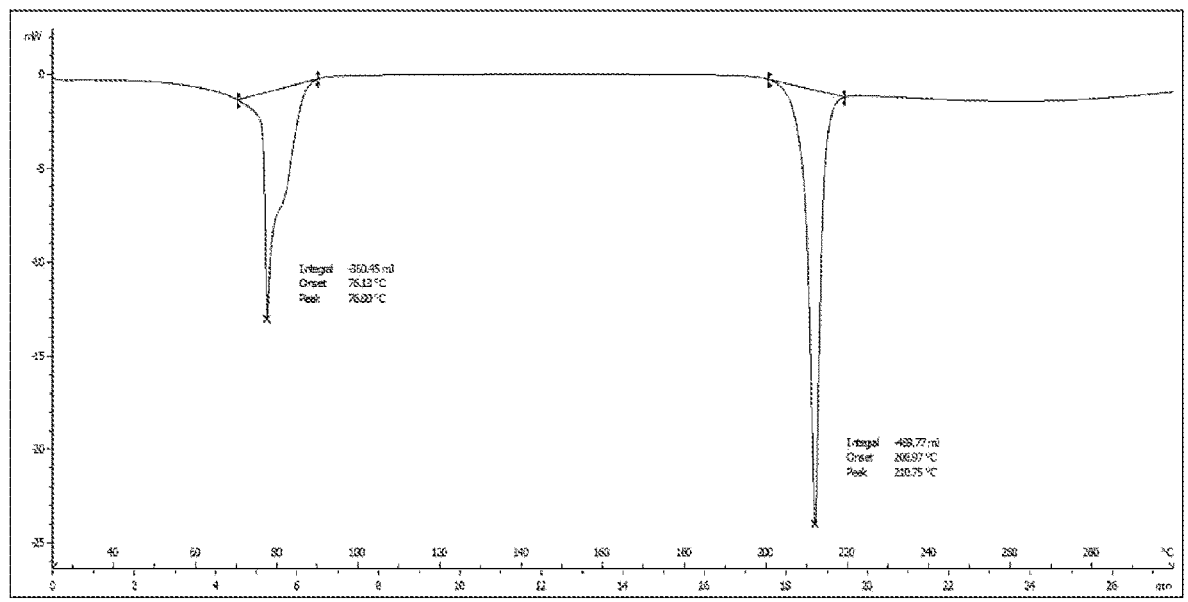
FIG. 11 illustrates a DSC thermogram of the crystalline Form-$T_{15-4}$.
Figure 12:
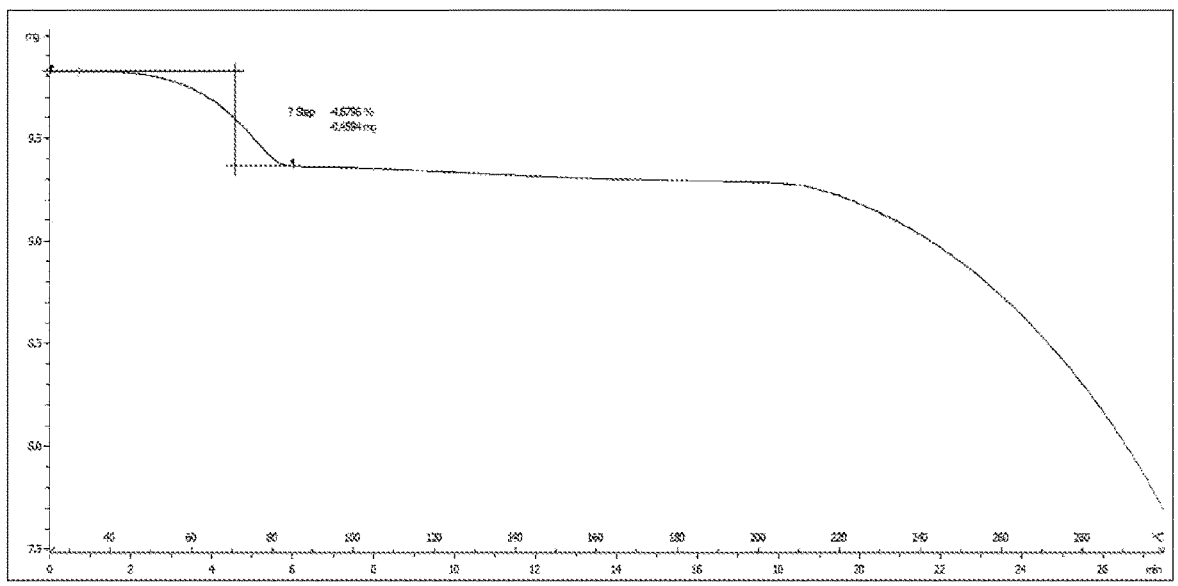
FIG. 12 illustrates a TGA curve of the crystalline Form-$T_{15-4}$.

The crystalline Form-$T_{15\text{-}4}$ is also characterized by a weight loss of about 4.6% observed between the temperature range of 30° C. to 90° C., as determined by TGA curve shown in FIG. 12. The crystalline Form-$T_{15\text{-}4}$ is further characterized by endothermic peaks are observed at about 75° C. to 80° C. and about 210° C., as determined by DSC shown in FIG. 11.

DMSO Solvate:

The DMSO solvate is produced by treating 3-{4-[(7-hydroxy-6-methyl-indan-4-yl)methyl]-3,5-dimethyl-1H-pyrazol-1-yl}-propanoic acid with DMSO to yield DMSO solvate of 3-{4-[(7-hydroxy-6-methyl-indan-4-yl)methyl]-3,5-dimethyl-1H-pyrazol-1-yl}-propanoic acid.

Figure 13:
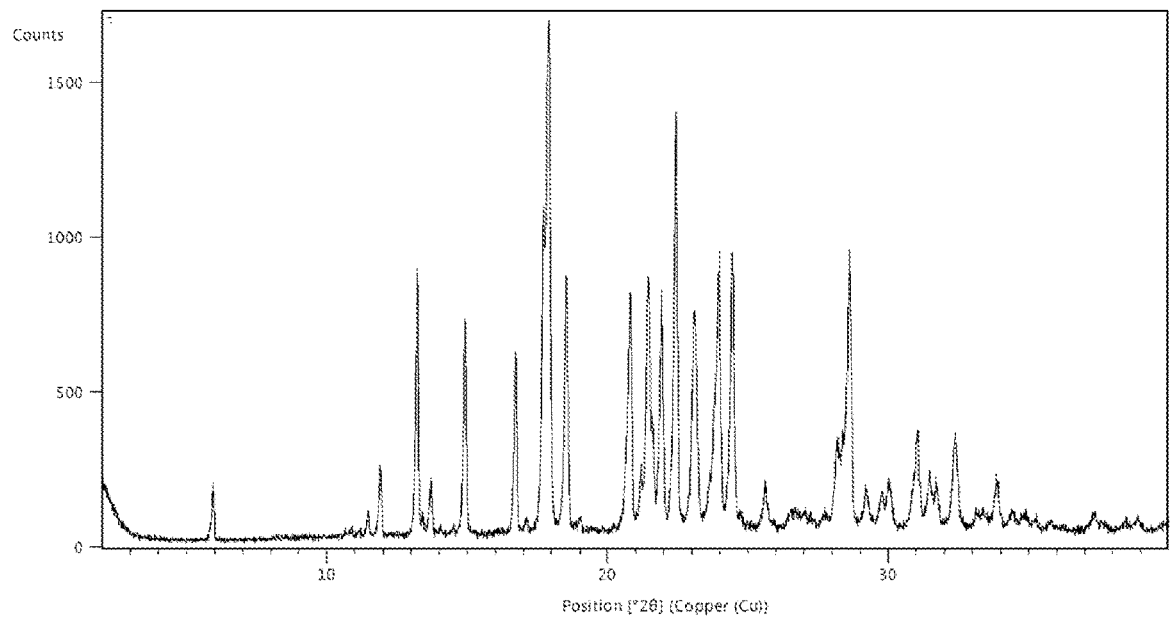
FIG. 13 illustrates an XRPD pattern of the DMSO solvate.
Figure 14:
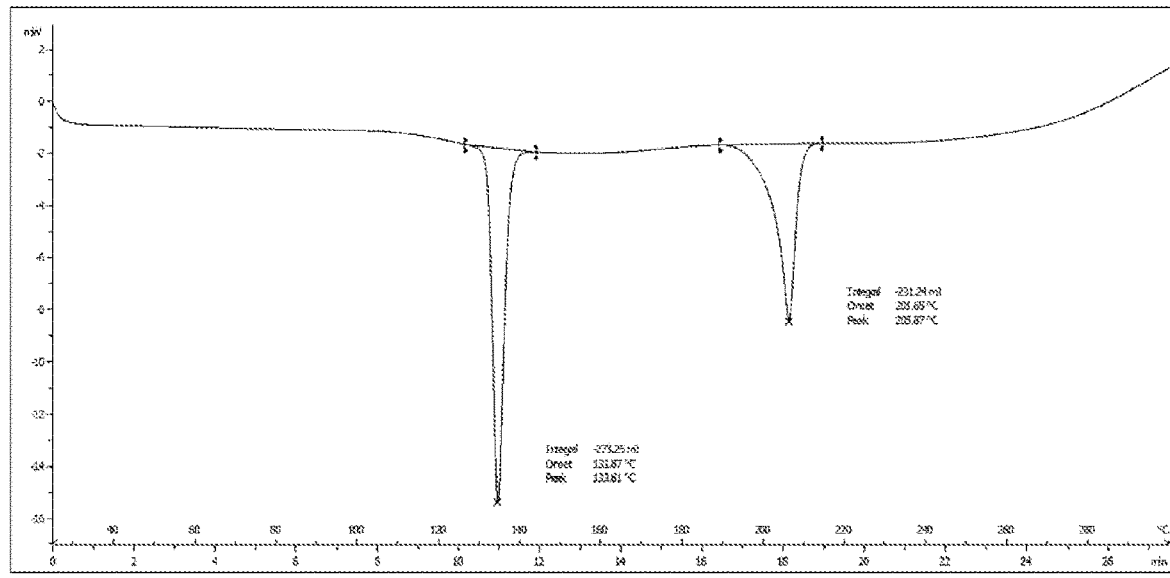
FIG. 14 illustrates a DSC thermogram of the DMSO solvate.
Figure 15:
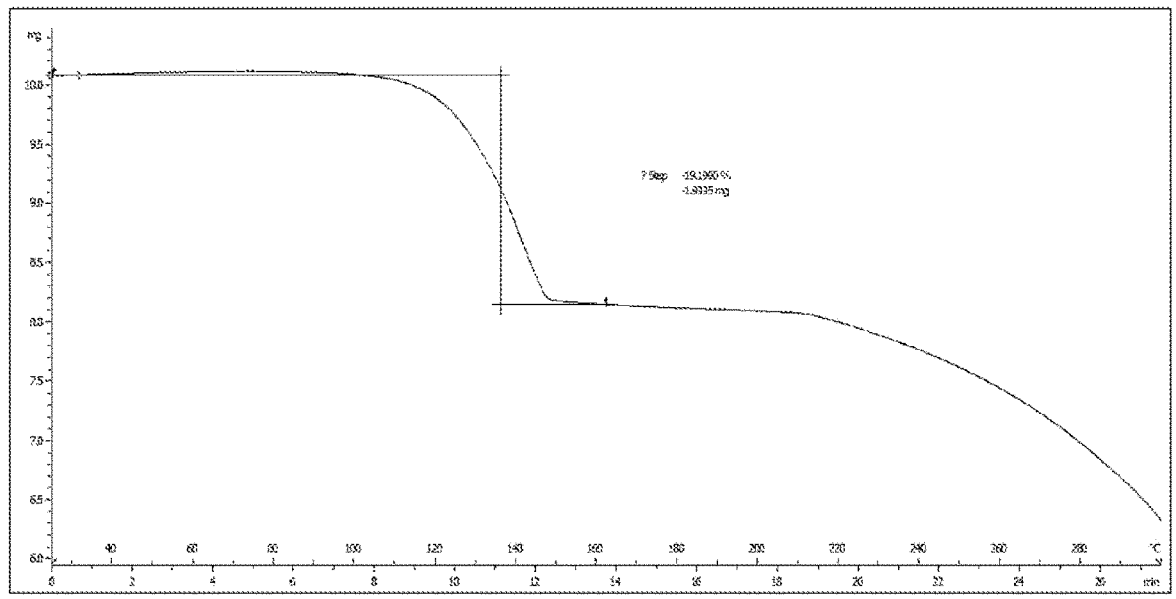
FIG. 15 illustrates a TGA curve of the DMSO solvate.

The X-ray powder diffraction pattern of DMSO solvate of 3-{4-[(7-hydroxy-6-methyl-indan-4-yl)methyl]-3,5-dimethyl-1H-pyrazol-1-yl}-propanoic acid is shown in FIG. 13. The DMSO solvate of 3-{4-[(7-hydroxy-6-methyl-indan-4-yl)methyl]-3,5-dimethyl-1H-pyrazol-1-yl}-propanoic acid is characterized by a weight loss of about 19% observed between the temperature range of 20° C. to 160° C., as determined by TGA curve as shown in FIG. 15. The DMSO solvate is further characterized by endothermic peaks observed at about 133° C. and about 205° C., as determined by DSC as shown in FIG. 14.

In one embodiment, the DMSO solvate of 3-{4-[(7-hydroxy-6-methyl-indan-4-yl)methyl]-3,5-dimethyl-1H-pyrazol-1-yl}-propanoic acid is converted into crystalline Form-$T_{15\text{-}3}$, when a suspension of DMSO solvate in water is stirred for about 30 minutes to about 5 hours.

Disodium Salt:

The disodium salt of 3-{4-[(7-hydroxy-6-methyl-indan-4-yl)methyl]1H-pyrazol-1-yl}-propanoic acid is produced by suspending 3-{4-[(7-hydroxy-6-methyl-indan-4-yl)methyl]-3,5-dimethyl-1H-pyrazol-1-yl}-propanoic acid or its ester in organic solvent and treating the suspension with sodium ion source.

The organic solvent is preferably selected from ester solvents, alcohol solvents, hydrocarbon solvents, halogenated hydrocarbon solvents, ketone solvents, ether solvents, polar aprotic solvents, or mixtures thereof.

Preferably, the sodium ion source is selected from sodium carbonate, sodium bicarbonate, sodium hydroxide, sodium methoxide, or sodium tert-butoxide. More preferably, the sodium ion source is sodium hydroxide.

The process of treating 3-{4-[(7-hydroxy-6-methyl-indan-4-yl)methyl]-3,5-dimethyl-1H-pyrazol-1-yl}-propanoic acid with sodium ion source is carried out at about 10° C. to 40° C. More preferably, the process is carried out at about 25° C. to about 35° C.

Figure 16:
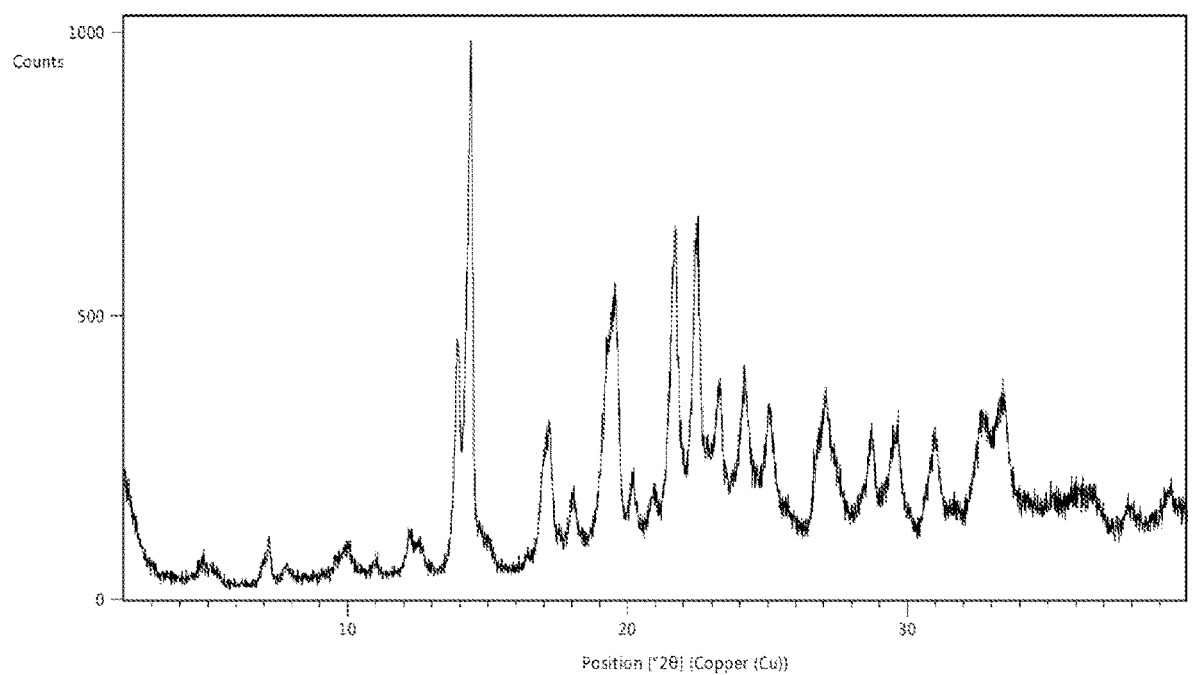
FIG. 16 illustrates an XRPD pattern of the disodium salt.
Figure 17:
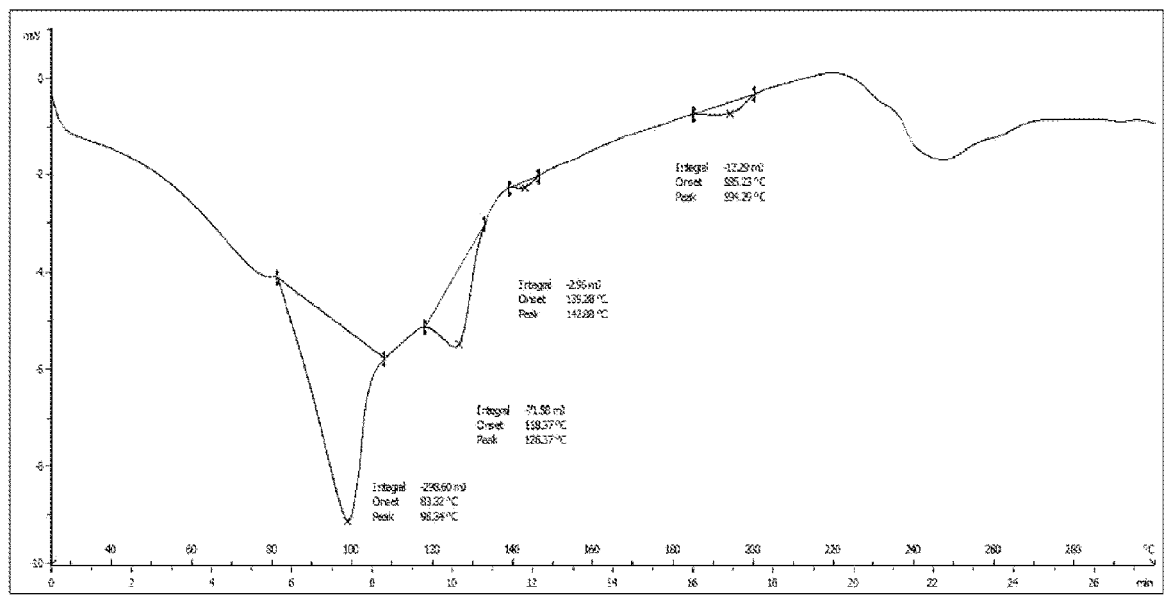
FIG. 17 illustrates a DSC thermogram of the disodium salt.
Figure 18:
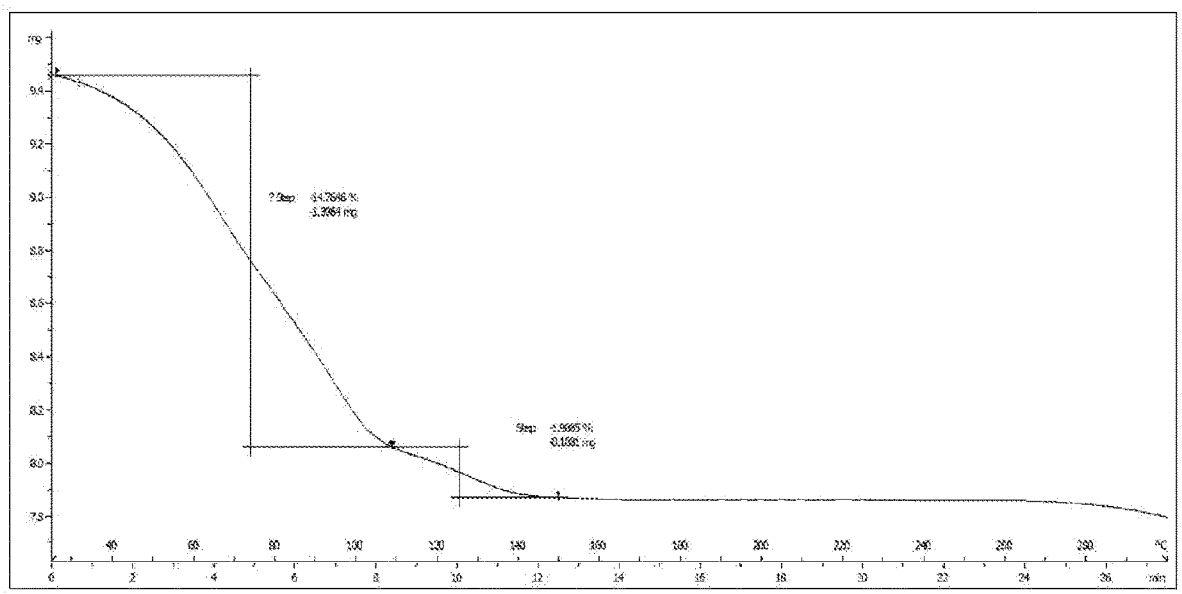
FIG. 18 illustrates a TGA curve of the disodium salt.
Figure 19:
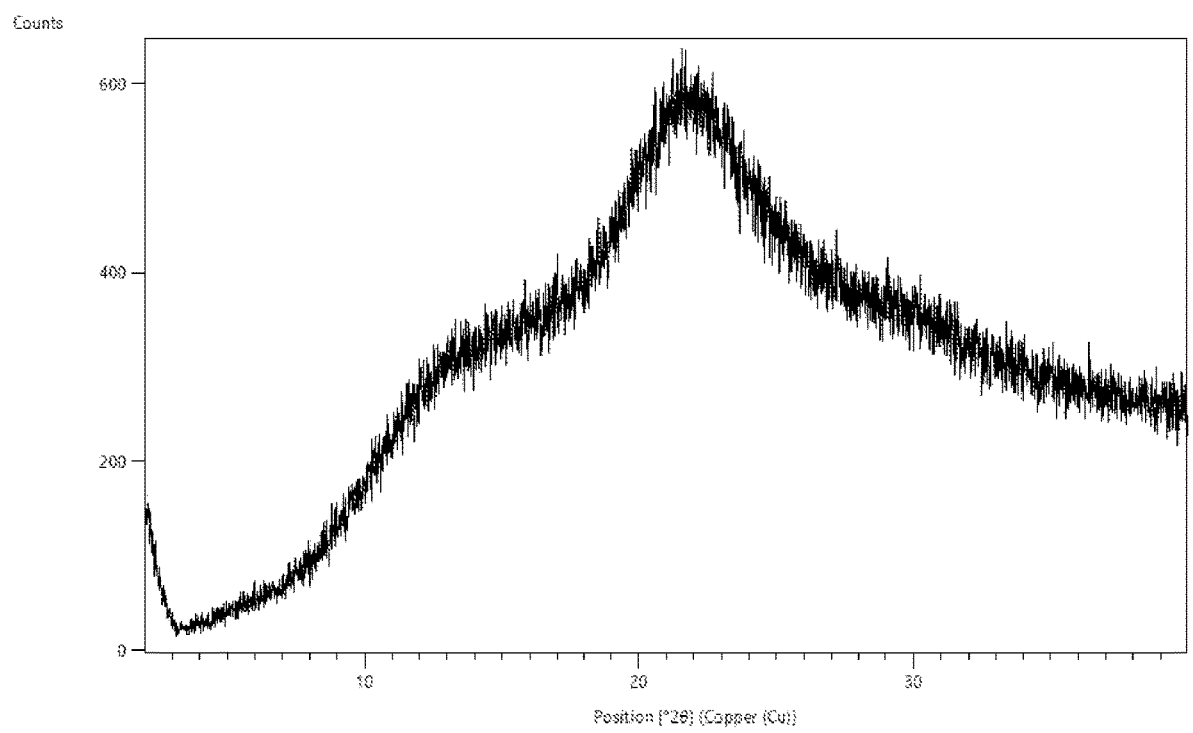
FIG. 19 illustrates an XRPD pattern of the amorphous form.

The X-ray powder diffraction pattern of disodium salt of 3-{4-[(7-hydroxy-6-methyl-indan-4-yl)methyl]-3,5-dimethyl-1H-pyrazol-1-yl}-propanoic acid is shown in FIG. 16. The disodium of 3-{4-[(7-hydroxy-6-methyl-indan-4-yl)methyl]-3,5-dimethyl-1H-pyrazol-1-yl}-propanoic acid is characterized by a weight loss of about 14.7% and about 1.9% observed between the temperature range of 0° C. to 110° C. and 110° C. to 150° C. respectively, as determined by TGA curve as shown in FIG. 18. The DSC of disodium salt 3-{4-[(7-hydroxy-6-methyl-indan-4-yl)methyl]-3,5-dimethyl-1H-pyrazol-1-yl}-propanoic acid is as shown in FIG. 17.

Amorphous Form:

The amorphous form or amorphous solid dispersion of 3-{4-[(7-hydroxy-6-methyl-indan-4-yl)methyl]-3,5-dimethyl-1H-pyrazol-1-yl}-propanoic acid is produced by providing a solution or suspension of 3-{4-[(7-hydroxy-6-methyl-indan-4-yl)methyl]-3,5-dimethyl-1H-pyrazol-1-yl}-propanoic acid in a suitable solvent, optionally adding one or more pharmaceutically acceptable carrier and isolating the amorphous form or amorphous solid dispersion of 3-{4-[(7-hydroxy-6-methyl-indan-4-yl)methyl]-3,5-dimethyl-1H-pyrazol-1-yl}-propanoic acid.

Not intending to limit the invention by a single mechanism of action, the methods of the present invention involve treating disease condition associated with inappropriate thyroid hormone activity selected from obesity, insulin resistance, dyslipidemia, metabolic syndrome, type II diabetes, replacement therapy in elderly subjects with hypothyroidism, depression, cardiovascular diseases and skin disorders by administering the crystalline Forms $T_{15\text{-}1}$, $T_{15\text{-}2}$, $T_{15\text{-}3}$, $T_{15\text{-}4}$, or DMSO solvate, or disodium salt, or amorphous form, or a combination thereof, of 3-{4-[(7-hydroxy-6-methyl-indan-4-yl)methyl]-3,5-dimethyl-1H-pyrazol-1-yl}-propanoic acid.

In various embodiments of the methods of the invention, the crystalline Forms Tis-1, $T_{15\text{-}2}$, $T_{15\text{-}3}$, $T_{15\text{-}4}$, or DMSO solvate, or disodium salt, or amorphous form, or a combination thereof, of 3-{4-[(7-hydroxy-6-methyl-indan-4-yl)methyl]-3,5-dimethyl-1H-pyrazol-1-yl}-propanoic acid are administered in pharmaceutical compositions. The pharmaceutical compositions of the invention comprise pharmaceutically acceptable carriers and excipients as well as crystalline Forms $T_{15\text{-}1}$, $T_{15\text{-}2}$, $T_{15\text{-}3}$, $T_{15\text{-}4}$, or DMSO solvate, or disodium salt, or amorphous form or a combination thereof of 3-{4-[(7-hydroxy-6-methyl-indan-4-yl)methyl]-3,5-dimethyl-1H-pyrazol-1-yl}-propanoic acid in order to formulate the composition for appropriate administration to the subject.

The following examples are presented to illustrate specific embodiments of the present invention and synthetic preparations thereof; and should not be interpreted as limitations upon the scope of the invention.

EXAMPLES

Example-1: Preparation of 7-hydroxy-6-methyl-indan-4-carbaldehyde

To the cooled solution of trifluoroacetic acid (250 mL) and acetic acid (250 mL), 5-methyl-indan-4-ol (100.0 g, 0.6748 mole) and hexamethylenetetramine (94.6 g, 0.6748 mole) were added. The reaction mixture was heated to 95° C. and stirred for 10 hours. After completion of reaction, the reaction mixture was quenched with water (500 mL) and neutralized with sodium hydroxide solution. The separated solid was filtered, washed with water (2×100 mL) and suck dried. The obtained solid was purified in a mixture of N,N-dimethylformamide and water to yield 7-hydroxy-6-methyl-indan-4-carbaldehyde as light brown solid.

Yield: 101.7 g (85.46%)
HPLC Purity: 99.45%
$^1$H-NMR (400 MHz, DMSO-$d_6$): δ 9.86 (1H, s), 7.42 (1H, s), 3.12-3.15 (2H, t), 2.76-2.80 (2H, t), 2.17 (3H, s), 1.99-2.07 (2H, m).
Mass: 175.13 ($M^+$−1)
Melting point: 158.50° C.

Example-2: Preparation of 7-(benzyloxy)-6-methyl-indan-4-carbaldehyde

To a stirred solution of 7-hydroxy-6-methyl-indan-4-carbaldehyde (100.0 g, 0.5675 mole) in N,N-dimethylformamide (250 mL), potassium carbonate (156.8 g, 1.135 mole) was added and stirred for 30 minutes. Subsequently, potassium iodide (9.42 g, 0.0567 mole) and benzyl chloride (71.8 mL, 0.6242 mole) were added to the reaction mixture and stirred for 12 hours at 25° C. to 30° C. After completion of reaction, the reaction mixture was quenched with water (2500 mL). The separated solid was filtered, washed with water (2×500 mL) and suck dried. The obtained solid was purified in hexane to yield 7-(benzyloxy)-6-methyl-indan-4-carbaldehyde as off white solid.

Yield: 127.5 g (84.38%)
HPLC purity: 99.53%
$^1$H-NMR (400 MHz, DMSO-$d_6$): δ 9.99 (1H, s), 7.54 (1H, s), 7.34-7.47 (5H, m), 5.07 (2H, s), 3.15-3.19 (2H, t), 2.95-2.99 (2H, t), 2.22 (3H, s), 2.02-2.09 (2H, m).
Mass: 267.07 ($M^+$−1)
Melting point: 44.96° C.

Example-3: Preparation of 4-(benzyloxy)-7-(chloromethyl)-5-methyl-indane

To the cooled solution of 7-(benzyloxy)-6-methyl-indan-4-carbaldehyde (125.0 g, 0.4693 mole) in dichloromethane (625 mL), sodium borohydride (18.64 g, 0.4928 mole) and acetic acid (125 mL) were added and stirred for 2 hours at 20° C. to 25° C. After completion of reaction, the reaction mixture was quenched with water (625 mL), layers were separated and the aqueous layer was extracted with dichloromethane (125 mL). The combined organic layer was washed with aqueous sodium bicarbonate solution (625 mL) and insitu carried forward to next step.

Thionyl chloride (38.44 mL, 0.5303 mole) was slowly added to the above organic layer at 20° C. to 25° C. and stirred for 2 hours. After completion of reaction, the reaction mixture was quenched into water (500 mL), layers were separated and the aqueous layer was extracted with dichloromethane (250 mL). The combined organic layer was washed with aqueous sodium bicarbonate solution (62.5 g in 700 mL water), and distilled to obtain solid. The obtained solid was purified in hexane to yield 4-(benzyloxy)-7-(chloromethyl)-5-methyl-indane as off white solid.

Yield: 116.5 g (86.53%)
HPLC purity: 99.16%
$^1$H-NMR (400 MHz, DMSO-$d_6$): δ 7.33-7.47 (5H, m), 7.05 (1H, s), 4.91 (2H, s), 4.68 (2H, s), 2.88-2.95 (4H, m), 2.17 (3H, s), 2.00-2.07 (2H, m).
Mass: 251.09 (fragmented peak corresponds to R—$CH_2^+$)
Melting point: 78.57° C.

Example-4: Preparation of 4-{[7-(benzyloxy)-6-methyl-indan-4-yl]methyl}-3,5-dimethyl-1H-pyrazole To a stirred solution of acetyl acetone (49.36 mL, 0.4812 mole) in acetone (575 mL) and N,N-dimethylformamide (5.75 mL), potassium carbonate (66.5 g, 0.4812 mole) was added and stirred at reflux temperature for 1 hour. To this mixture, potassium iodide (76.55 g, 0.4611 mole) and a solution of 4-(benzyloxy)-7-(chloromethyl)-5-methyl-indane (115.0 g, 0.4009 mole) in acetone (575 mL) were added at 40° C. and stirred at reflux temperature for 4 hours. After completion of reaction, the reaction mixture was filtered, washed with acetone (2×230 mL) and the filtrate was distilled to obtain residue. The residue was dissolved in dichloromethane (460 mL) and washed with aqueous hydrochloric acid solution (575 mL). The aqueous layer was extracted with dichloromethane (115 mL), the combined organic layer was washed with water (575 mL) and distilled to get residue. The residue was dissolved in isopropyl alcohol (387 mL), and a solution of hydrazine hydrate (23.87 mL, 0.4865 mole) in isopropyl alcohol (387 mL) and acetic acid (51.15 mL) were added and stirred at reflux temperature for 11 hours. The reaction mixture was distilled to obtain residue. Water (1240 mL) was added to the residue, separated solid was filtered, washed with water (465 ml) and suck dried. The solid was purified in hexane and dried to yield 4-{[7-(benzyloxy)-6-methyl-indan-4-yl]methyl}-3,5-dimethyl-1H-pyrazole as off white solid.

Yield: 111.0 g (79.8%)
HPLC Purity: 99.39%
$^1$H-NMR (400 MHz, DMSO-$d_6$): δ 11.97 (1H, s), 7.31-7.44 (5H, m), 6.53 (1H, s), 4.82 (2H, s), 3.50 (2H, s), 2.86-2.89 (2H, t), 2.73-2.77 (2H, t), 2.17 (3H, s), 1.97-2.09 (8H, m).
Mass: 347.16 (M++1)
Melting point: 133.75° C.

Example-5: Preparation of ethyl 3-(4-{[7-(benzyloxy)-6-methyl-indan-4-yl]methyl}-3,5-dimethyl-1H-pyrazol-1-yl)propanoate To a stirred solution of 4-{[7-(benzyloxy)-6-methyl-indan-4-yl]methyl}-3,5-dimethyl-1H-pyrazole (109.0 g, 0.3146 mole) in N,N-dimethylformamide (545 mL), cesium carbonate (205.0 g, 0.6292 mole) was added and stirred for 1 hour at 25° C. to 30° C. Subsequently, ethyl-3-bromo propionate (44.1 mL, 0.3461 mole) was added to the reaction mixture stirred for 10 hours at 25° C. to 30° C. After completion of reaction, the reaction mixture was filtered and the filtrate was quenched with water (2616 mL). The separated solid was filtered, washed with water, and suck dried. The solid was purified in hexane (872 mL) and dried to yield ethyl 3-(4-{[7-(benzyloxy)-6-methyl-indan-4-yl]methyl}-3,5-dimethyl-1H-pyrazol-1-yl)-propanoate as white solid.

Yield: 90.0 g (64.05%)
HPLC Purity: 97.22%
$^1$H-NMR (400 MHz, DMSO-$d_6$): δ 7.33-7.44 (5H, m), 6.50 (1H, s), 4.82 (2H, s), 4.12-4.15 (2H, t), 4.00-4.05 (2H, q), 3.50 (2H, s), 2.85-289 (2H, t), 2.72-2.79 (4H, m), 2.10 (3H, s), 2.08 (3H, s), 1.97-2.00 (2H, m), 1.91 (3H, s), 1.13-1.15 (3H, t).
Mass: 447.23 (M++1)
Melting point: 72.27° C.

Example-6: Preparation of ethyl 3-{4-[(7-hydroxy-6-methyl-indan-4-yl)methyl]-3,5-dimethyl-1H-pyrazol-1-yl}propanoate To a stirred solution of ethyl 3-(4-{[7-(benzyloxy)-6-methyl-indan-4-yl]methyl}-3,5-dimethyl-1H-pyrazol-1-yl)propanoate (45.0 g) in ethyl acetate (675 mL) in hydrogenator, 10% Palladium on carbon (4.5 g) in water (4.5 mL) were added and stirred under hydrogen pressure (200 psi) at 55° C. to 60° C. for 12 hours. After completion of reaction, dichloromethane (450 mL) was added, the reaction mixture was filtered through Hyflo® bed and the filtrate was distilled to obtain solid. The obtained solid was purified in ethyl acetate to obtain ethyl 3-{4-[(7-hydroxy-6-methyl-indan-4-yl)methyl]-3,5-dimethyl-1H-pyrazol-1-yl}propanoate as white solid.

Yield: 31.0 g (86.32%)
HPLC Purity: 98.70%
$^1$H-NMR (400 MHz, DMSO-$d_6$): δ 8.10 (1H, s), 6.39 (1H, s), 4.10-4.14 (2H, t), 3.99-4.05 (2H, q), 3.42 (2H, s), 2.72-2.78 (4H, m), 2.66-2.70 (2H, m), 2.08 (3H, s), 2.02 (3H, s), 1.93-1.96 (2H, m), 1.89 (3H, s), 1.11-1.15 (3H, t).
Mass: 357.17 (M$^+$+1)
Melting point: 158.34° C.

Example-7: Preparation of 3-{4-[(7-hydroxy-6-methyl-indan-4-yl)methyl]-3,5-dimethyl-1H-pyrazol-1-yl}propionic Acid To a stirred suspension of ethyl 3-{4-[(7-hydroxy-6-methyl-indan-4-yl)methyl]-3,5-dimethyl-1H-pyrazol-1-yl}propanoate (72.0 g, 0.2020 mole) in tetrahydrofuran (360 mL), aqueous sodium hydroxide solution (16.16 g, 0.4040 mole) in water (504 mL) was added at 25° C. to 30° C. and stirred for 3 hours. After completion of reaction, ethyl acetate (1080 mL) was added and layers were separated. The aqueous layer was acidified with aqueous hydrochloric acid solution (72 mL hydrochloric acid in 432 mL water), separated solid was filtered, washed with water and suck dried. The solid was stirred in water (1440 mL) for 1 hour, filtered, washed with water followed by ethyl acetate and suck dried. The solid was further stirred in ethyl acetate (720 mL), filtered, washed with ethyl acetate and dried to get 3-{4-[(7-hydroxy-6-methyl-indan-4-yl)methyl]-3,5-dimethyl-1H-pyrazol-1-yl}propanoic acid as white solid.

Yield: 56.0 g (84.4%)
HPLC Purity: 99.78%
$^1$H-NMR (400 MHz, DMSO-$d_6$): δ 12.31 (1H, bs), 8.09 (1H, s), 6.40 (1H, s), 4.07-4.10 (2H, t), 3.42 (2H, s), 2.67-2.76 (6H, m), 2.08 (3H, s), 2.02 (3H, s), 1.95-1.98 (2H, m), 1.93 (3H, s).
Mass: 329.09 (M$^+$+1)
Melting point: 212.37° C.

Example-8: Preparation of 3-{4-[(7-hydroxy-6-methyl-indan-4-yl)methyl]-3,5-dimethyl-1H-pyrazol-1-yl}propionic Acid (Crystalline Form-$T_{15-3}$)

To a stirred suspension of ethyl 3-{4-[(7-hydroxy-6-methyl-indan-4-yl)methyl]-3,5-dimethyl-1H-pyrazol-1-yl}propanoate (1.0 g) in acetic acid (5.0 mL) and water (5.0 mL), concentrated hydrochloric acid (2.0 mL) was added and stirred for 8 hours at 60° C. to 65° C. To this mixture, concentrated hydrochloric acid (3.0 mL) was added and stirred for 3 hours at 60° C. to 65° C. After completion of reaction, the reaction mixture was cooled to 25° C. to 30° C., water (20.0 mL) was added, and stirred for 30 minutes. The separated solid was filtered, washed with water (10 mL) and dried to yield 3-{4-[(7-hydroxy-6-methyl-indan-4-yl)methyl]-3,5-dimethyl-1H-pyrazol-1-yl}propanoic acid as a white solid.

Yield: 450.0 mg (49.0%)

Example-9: Preparation of 4-(benzyloxy)-5-methyl-indane

To a stirred solution of 5-methyl-indan-4-ol (30.0 g, 0.2027 mole) in N, N-dimethylformamide (70 mL), potassium carbonate (56.0 g, 0.4054 mole) was added and stirred for 30 minutes at 25° C. to 30° C. Subsequently, benzyl chloride (31.0 g, 0.2432 mole) and potassium iodide (3.37 g, 0.0203 mole) were added to the reaction mixture and stirred for 2 hours at 25° C. to 30° C. After completion of reaction, the reaction mixture was quenched with water (300 mL) and extracted with ethyl acetate. The ethyl acetate layer was dried and distilled. The crude product was purified by column chromatography using hexane:ethyl acetate to get 4-(benzyloxy)-5-methyl-indane as a liquid.

Yield: 29.0 g (60.0%)
HPLC Purity: 95.35%
$^1$H-NMR (400 MHz, DMSO-$d_6$): δ 7.43-7.45 (2H, m), 7.14-7.39 (3H, m), 6.93-6.95 (1H, d), 6.80-6.86 (1H, d), 4.85 (2H, s), 2.85-2.89 (2H, m), 2.77-2.81 (2H, m), 2.21 (3H, s), 1.92-2.17 (2H, m).

Example-10: Preparation of 4-(benzyloxy)-7-(chloromethyl)-5-methyl-indane

To the clear solution of 4-(benzyloxy)-5-methyl-indane (5.0 g, 0.0209 mole) in acetic acid (20 mL), paraformaldehyde (1.17 g, 0.0419 mole) was added and hydrochloric acid gas was purged for 2 hours at 25° C. to 30° C. After completion of reaction, water (50 mL) was added to the reaction mixture, the separated solid was filtered and suck dried to get 4-(benzyloxy)-7-(chloromethyl)-5-methyl-indane as a white solid.

Yield: 5.0 g (83.3%)
HPLC Purity: 90.11%
$^1$H-NMR (400 MHz, DMSO-$d_6$): δ 7.32-7.46 (5H, m), 7.04 (1H, s), 4.87 (2H, s), 4.67 (2H, s), 2.87-2.92 (4H, m), 2.16 (3H, s), 1.99-2.16 (2H, m).
Melting point: 70.96° C.
Mass: 250.92 (fragmented peak corresponds to R—CH$_2$$^+$)

Example-11: Preparation of 3-(4-{[7-(benzyloxy)-6-methyl-indan-4-yl]methyl}-3,5-dimethyl-1H-pyrazol-1-yl)propanoic Acid To a stirred suspension of ethyl 3-(4-{[7-(benzyloxy)-6-methyl-indan-4-yl]methyl}-3,5-dimethyl-1H-pyrazol-1-yl)propanoate (8.5 g, 0.019 mole) in tetrahydrofuran (42.5 mL), aqueous sodium hydroxide solution (1.5 g, 0.038 mole in water (18 mL)) was added and stirred for 3 hours for 25° C. to 30° C. After completion of reaction, water (115.7 mL) was added to the reaction mixture and washed with ethyl acetate (67 mL). The aqueous layer was acidified with 2N aqueous hydrochloric acid (20 mL), separated solid was filtered, washed with water (85 mL) and dried to yield 3-(4-{[7-(benzyl oxy)-6-methyl-indan-4-yl]methyl}-3,5-dimethyl-1H-pyrazol-1-yl)propanoic acid as white solid.

Yield: 7.2 g (90.4%)
HPLC Purity: 99.15%

¹H-NMR (400 MHz, DMSO-d$_6$): δ 12.31 (1H, bs), 7.31-7.45 (5H, m), 6.52 (1H, s), 4.83 (2H, s), 4.09-4.13 (2H, t), 3.50 (1H, s), 2.86-2.90 (2H, t), 2.69-2.76 (4H, m), 2.11 (3H, s), 2.10 (3H, s), 1.77-2.03 (2H, m), 1.17 (3H, t).
Melting point: 140.18° C.
Mass: 419.14 (M$^+$+1)

Example-12: Preparation 3-{4-[(7-hydroxy-6-methyl-indan-4-yl)methyl]-3,5-dimethyl-1H-pyrazol-1-yl}propanoic Acid (Crystalline Form-T$_{15\text{-}3}$)

A suspension of 10% palladium on carbon (0.3 g in 0.3 mL water), 3-(4-{[7-(benzyl oxy)-6-methyl-indan-4-yl]methyl}-3,5-dimethyl-1H-pyrazol-1-yl)-propanoic acid (3.0 g, 0.0077 mole) and methanol (50 mL) were added into hydrogenator and stirred under hydrogen pressure (200 psi) for 8 hours at 55° C. After completion of reaction, the reaction mixture was cooled to 25° C. to 30° C. and dichloromethane (100 mL) was added. The reaction mixture was filtered through Hyflo® bed and the filtrate was distilled to obtain crude product (2.0 g). Ethyl acetate (30 mL) was added to the crude product, stirred for 1 hour, separated solid was filtered and washed with ethyl acetate (15 mL) to get 3-{4-[(7-hydroxy-6-methyl-indan-4-yl)methyl]-3,5-dimethyl-1H-pyrazol-1-yl}propanoic acid as a white solid.
Yield: 1.86 g (78.96%)
HPLC Purity: 97.81%
¹H-NMR (400 MHz, DMSO-d$_6$): δ 12.31 (1H, bs), 8.09 (1H, s), 6.40 (1H, s), 4.07-4.10 (2H, t), 3.42 (2H, s), 2.67-2.76 (6H, m), 2.08 (3H, s), 2.02 (3H, s), 1.93-1.97 (2H, m), 1.90 (3H, s).
Melting point: 210.2° C.
Mass: 329.15 (M$^+$+1)

Example-13: Preparation 3-{4-[(7-hydroxy-6-methyl-indan-4-yl)methyl]-3,5-dimethyl-1H-pyrazol-1-yl}propanoic Acid (Crystalline Form-T$_{15\text{-}1}$)

A suspension of 10% palladium on carbon (0.3 g in 0.3 mL water) and aqueous sodium hydroxide solution (0.57 g, 0.0143 mole) in water (70 mL) was added into hydrogenator and then 3-(4-{[7-(benzyloxy)-6-methyl-indan-4-yl]methyl}-3,5-dimethyl-1H-pyrazol-1-yl)propanoic acid (3.0 g, 0.0077 mole) was added. The reaction mixture was stirred under hydrogen pressure (200 psi) for 5 hours at 55° C. After completion of reaction, the reaction mixture was cooled to 25° C. to 30° C., filtered through Hyflo® bed and washed with water (40 mL). The filtrate was acidified with 50% aqueous hydrochloric acid (20 mL) and stirred for 15 minutes. The separated solid was filtered, washed with water (15 mL) and such dried. The solid was suspended in water (60 mL), stirred for 1 hour, filtered and washed with water (18 mL) and then with ethyl acetate (15 mL). The solid was further suspended in ethyl acetate (30 mL), stirred for 30 minutes, filtered, washed with ethyl acetate (15 mL) and dried to yield 3-{4-[(7-hydroxy-6-methyl-indan-4-yl)methyl]-3,5-dimethyl-1H-pyrazol-1-yl}propanoic acid as a white solid.
Yield: 1.4 g (59.4%)
HPLC Purity: 98.79%
¹H-NMR (400 MHz, DMSO-d$_6$): δ 12.31 (1H, bs), 8.09 (1H, s), 6.40 (1H, s), 4.07-4.11 (2H, t), 3.42 (2H, s), 2.67-2.76 (6H, m), 2.08 (3H, s), 2.02 (3H, s), 1.93-1.98 (2H, m), 1.90 (3H, s).
Melting point: 210.5° C.
Mass: 329.12 (M$^+$+1)

Example-14: Preparation of 3-{[7-(benzyloxy)-6-methyl-indan-4-yl]-methylidene}pentane-2,4-dione To a stirred solution of 7-(benzyloxy)-6-methyl-indan-4-carbaldehyde (20.0 g, 0.0751 mole) and acetyl acetone (37.59 g, 0.3755 mole) in toluene (200 mL), piperidine (1.5 mL) was added and refluxed for 4 hours. The by-product water was removed during reflux with dean-stark apparatus. Thereafter, a second lot of acetyl acetone (37.59 g, 0.3755 mole) was added, refluxed for 3 hours and distilled to obtain residue. The obtained residue was purified by column chromatography to yield 3-{[7-(benzyloxy)-6-methyl-indan-4-yl]methylidene}pentane-2,4-dione HPLC Purity: 96.57%
¹H-NMR (400 MHz, DMSO-d$_6$): δ 7.56 (1H, s), 7.32-7.46 (5H, m), 6.87 (1H, s), 4.98 (2H, s), 2.96-3.00 (4H, m), 2.40 (3H, s), 2.22 (3H, s), 2.12 (3H, s), 2.01-2.10 (2H, m).
Mass: 349.11 (M$^+$+1)

Example-15: Preparation of 3-{[7-(benzyloxy)-6-methyl-indan-4-yl]methyl}-pentane-2,4-dione To a suspension of 3-{[7-(benzyloxy)-6-methyl-indan-4-yl]methylidene}-pentane-2,4-dione (1.0 g, 0.00286 mole) and Zinc dust (2.06 g, 0.0315 mole), acetic acid (7.0 mL) was added and stirred for 2 hours at 25° C. to 30° C. Ethyl acetate (10 ml) was added to the reaction mixture, filtered through Hyflo® bed and washed with ethyl acetate. The filtrate was washed with water, dried over sodium sulphate, and distilled to obtain crude product, which was purified by column chromatography to yield 3-{[7-(benzyloxy)-6-methyl-indan-4-yl]methyl}pentane-2,4-dione.

Example-16: Preparation of 4-{[7-(benzyloxy)-6-methyl-indan-4-yl]methyl}-3,5-dimethyl-1H-pyrazole To a stirred solution of 3-{[7-(benzyloxy)-6-methyl-indan-4-yl]methyl}-pentane-2,4-dione (0.5 g, 0.00142 mole) in isopropyl alcohol (4.0 mL), hydrazine hydrate (0.11 g, 0.00214 mole) in isopropyl alcohol (5.0 mL) was added, heated the mixture to 80° C. to 85° C., and stirred for 1 hour. Subsequently, acetic acid (0.5 mL) was added and stirred for 11 hours at 80° C. to 85° C. Thereafter, water (15 mL) was added to the reaction mixture and extracted with dichloromethane. The organic layer was dried over sodium sulphate and distilled to obtain crude product, which was purified by column chromatography to yield 4-{[7-(benzyloxy)-6-methyl-indan-4-yl]methyl}-3,5-dimethyl-1H-pyrazole.
HPLC Purity: 93.38%
¹H-NMR (400 MHz, DMSO-d$_6$): δ 11.94 (1H, s), 7.31-7.44 (5H, m), 6.53 (1H, s), 4.82 (2H, s), 3.50 (2H, s), 2.86-2.89 (2H, t), 2.73-2.77 (2H, t), 2.32 (3H, s), 1.97-2.09 (8H, m).
Mass: 347.10 (M$^+$+1)
Melting point: 133.75° C.

Example-17: Preparation of 2-hydroxy-3-methylbenzaldehyde

To a stirred solution of 2-methyl phenol (100.0 g, 0.9248 mole) in acetonitrile (1000 mL), magnesium chloride (176.1 g, 1.8496 mole), triethylamine (562.0 g, 5.5488 mole), and paraformaldehyde (166.6 g, 5.5488 mole) were added and stirred for 2 hours at reflux temperature. After completion of reaction, the reaction mixture was cooled and quenched with aqueous hydrochloric acid (600 mL) in water (400 mL). The reaction mixture was filtered through Hyflo® bed and the filtrate was extracted with ethyl acetate (2×1000 mL). The combined organic layer was washed with saturated aqueous sodium chloride solution (1000 mL) and distilled to obtain 2-hydroxy-3-methylbenzaldehyde as thick liquid.

Yield: 120.0 g (96%)
HPLC Purity: 92.16%
$^1$H-NMR (400 MHz, DMSO-$d_6$): δ 11.05 (1H, s), 10.03 (1H, s), 7.59-7.60 (1H, d), 7.47-7.49 (1H, d), 6.96-7.00 (1H, m), 2.18 (3H, s).
Mass: 135 ($M^+$−1)

Example-18: Preparation of 2-formyl-6-methylphenyl-4-methylbenzene-sulfonate To a stirred solution of 2-hydroxy-3-methylbenzaldehyde (110.0 g, 0.8079 mole) in N,N-dimethylformamide (330 mL), potassium carbonate (133.8 g, 0.9681 mole) was added and stirred for 30 minutes at 25° C. to 30° C. Tosyl chloride (169.4 g, 0.8887 mole) was added to the reaction mixture and stirred for 3 hours at 25° C. to 30° C. After completion of reaction, the reaction mixture was quenched with water (1650 mL). The separated solid was filtered, washed with water (2×275 mL) and dried under vacuum to obtain 2-formyl-6-methylphenyl-4-methylbenzene-sulfonate as off white solid.

Yield: 198.0 g (84.5%)
HPLC Purity: 94.80%
$^1$H-NMR (400 MHz, DMSO-$d_6$): δ 9.88 (1H, s), 7.78-7.81 (2H, d), 7.64-7.74 (2H, m), 7.52-7.54 (2H, d), 7.42-7.46 (1H, d), 2.42 (3H, s), 2.04 (3H, s).
Mass: 291 ($M^+$+1)
Melting point: 60.7° C.

Example-19: Preparation of 3-(3-methyl-2-{[(4-methylphenyl)sulfonyl]oxy}-phenyl)propionic Acid To a stirred solution of formic acid (39.64 g, 0.8611 mole) and N,N-dimethylformamide (300 mL), trimethylamine (34.85 g, 0.3444 mole) was slowly added at 25° C. to 30° C. and stirred for 30 minutes. 2,2-dimethyl-1,3-dioxane-4,6-dione (Meldrum's acid) (52.13 g, 0.3617 mole) and 2-formyl-6-methylphenyl 4-methylbenzenesulfonate (100.0 g, 0.3444 mole) were added to the reaction mixture and stirred for 3 hours at 100±3° C. After completion of reaction, the reaction mixture was cooled to 25° C. to 30° C. and quenched with water (1200 mL). The separated solid was filtered, washed with water (2×250 mL) and dried to yield 3-(3-methyl-2-{[(4-methylphenyl)sulfonyl]oxy}phenyl) propionic acid as off white solid.

Yield: 106.0 g (92.17%)
HPLC Purity: 91.26%
$^1$H-NMR (400 MHz, DMSO-$d_6$): δ 7.86-7.88 (2H, d), 7.51-7.53 (2H, d), 7.15-7.18 (3H, m), 2.68-2.72 (2H, t), 2.58 (3H, s), 2.39-2.43 (2H, t), 2.04 (3H, s).
Mass: 333.07 ($M^+$−1)
Melting point: 106.05° C.

Example-20: Preparation of 5-methyl-1-oxo-indan-4-yl-4-methylbenzene-sulfonate To a stirred solution of 3-(3-methyl-2-{[(4-methylphenyl) sulfonyl]oxy}-phenyl)propionic acid (100.0 g, 0.2990 mole) in dichloromethane (600 mL), thionyl chloride (53.37 g, 0.4485 mole) was added slowly and stirred for 1 hour at 25° to 30° C. The reaction mixture was slowly added to a suspension of aluminium chloride (119.63 g, 0.8971 mole) in dichloromethane (600 mL) at 25° C. to 30° C. and stirred for 1 hour. After completion of reaction, the reaction mixture was quenched with 1N aqueous hydrochloric acid (1000 mL) and layers were separated. The organic layer was washed with water (1000 mL), dried and distilled to obtain crude product which was purified in methanol (200 mL) to obtain 5-methyl-1-oxo-indan-4-yl-4-methylbenzene-sulfonate as off white solid.

Yield: 70.0 g (74.5%)
HPLC Purity: 99.61%
$^1$H-NMR (400 MHz, DMSO-$d_6$): δ 7.90-7.92 (2H, d), 7.52-7.56 (3H, m), 7.38-7.40 (1H, d), 2.88-2.91 (2H, t), 2.58-2.61 (2H, t), 2.50 (3H, s), 2.12 (3H, s).
Mass: 316.99 ($M^+$+1)
Melting point: 126.85° C.

Example-21: Preparation of 4-hydroxy-5-methyl-indan-1-one

To a stirred suspension of 5-methyl-1-oxo-indan-4-yl-4-methyl benzenesulfonate (69.0 g, 0.2183 mole) in methanol (345 mL), aqueous sodium hydroxide solution (26.2 g, 0.655 mole) in water (690 mL) was added at 25° C. to 30° C. The reaction mixture was heated to 70° C. and stirred for 5 hours. After completion of reaction, the reaction mixture was distilled to remove methanol and then acidified with dilute aqueous hydrochloric acid. The separated solid was filtered, washed with water (200 mL) and dried to obtain 4-hydroxy-5-methyl-indan-1-one as off white solid.

Yield: 26.0 g (73.9%)
HPLC Purity: 99.14%
$^1$H-NMR (400 MHz, DMSO-$d_6$): δ 9.20 (1H, s), 7.14-7.16 (1H, d), 7.03-7.05 (1H, d), 2.94-2.97 (2H, t), 2.58-2.59 (2H, t), 2.24 (3H, s).
Mass: 161.08 ($M^+$−1)
Melting point: 210.83° C.

Example-22: Preparation of 5-methyl-indan-4-ol

A suspension of 4-hydroxy-5-methyl-indan-1-one (30.0 g) in methanol (300 mL) was added into hydrogenator and then 10% Palladium on carbon (3.0 g) in water (3.0 mL) and acetic acid (3.0 mL) were added. The reaction mixture was stirred under hydrogen pressure (200 psi) for 12 hours at 55° C. After completion of reaction, the reaction mixture was filtered through Hyflo® bed and the filtrate was distilled to obtain residue. The obtained residue was dissolved in ethyl acetate (200 mL), washed with saturated aqueous sodium bicarbonate solution (200 mL) and then with water (200 mL). The organic layer was distilled to yield 5-methyl-indan-4-ol as off white solid.

Yield: 26.0 g (95.2%)
HPLC Purity: 98.31%
$^1$H-NMR (400 MHz, DMSO-$d_6$): δ 8.35 (1H, s), 6.80-6.82 (1H, d), 6.57-6.58 (1H, d), 2.74-2.78 (4H, m), 2.10 (3H, s), 1.92-1.97 (2H, m).
Mass: 148.93 ($M^+$+1)
Melting point: 95.79° C.

Example-23: Preparation of 5-methyl-indan-4-yl 4-methylbenzene-1-sulfonate

To a stirred solution of 5-methyl-1-oxo-indan-4-yl 4-methylbenzene-1-sulfonate (10.0 g, 0.031 mole) in dichloromethane (100 mL), triethylsilane (40.36 mL, 0.252 mole)

and boron trifluoride etherate (23.98 mL, 0.1940 mole) were added at 0° C. to −5° C. and stirred for 12 hours at 25° C. to 30° C. After completion of reaction, water (100 mL) was added and neutralized with sodium carbonate. The reaction mixture was extracted with ethyl acetate (2×100 mL), combined organic layer was dried and distilled to afford crude product. The crude product was purified in methanol to yield 5-methyl-indan-4-yl 4-methylbenzene-1-sulfonate as a solid.

Yield: 4.1 g

Example-24: Preparation of 5-methyl-indan-4-yl 4-methylbenzene-1-sulfonate

To a stirred solution of 5-methyl-1-oxo-indan-4-yl 4-methylbenzene-1-sulfonate (15.0 g, 0.0474 mole) in dichloromethane (180 mL), anhydrous aluminium chloride (18.96 g, 0.1422 mole) and triethylsilane (30.27 mL, 0.1896 mole) were added and stirred for 4 hours at 25° C. to 30° C. After completion of reaction, 1N aqueous hydrochloric acid (150 mL) was added, stirred for 30 minutes, and layers were separated. The aqueous layer was extracted with dichloromethane (150 mL) and the combined organic layer was washed with water (2×150 mL) and distilled to afford crude product. The crude product was purified in methanol (50 mL) to yield 5-methyl-indan-4-yl 4-methylbenzene-1-sulfonate as a solid.

Yield: 3.37 g

Example-25: Preparation of 5-methyl-1H-indan-4-ol

To a stirred suspension of 5-methyl-indan-4-yl 4-methylbenzene-1-sulfonate (4.0 g, 0.0126 mole) in methanol (20 mL), sodium hydroxide (2.02 g, 0.05 mole) was added and stirred for 6 hours at 50-55° C. After completion of reaction, water (20 mL) was added and acidified with dilute hydrochloric acid. The precipitated solid was filtered, washed with water and dried to yield 5-methyl-1H-indan-4-ol.

Yield: 1.4 g

Example-26: Preparation of ethyl 3-(3,5-dimethyl-1H-pyrazol-1-yl)-propanoate

To a stirred suspension of 3,5-dimethyl-1H-pyrazole (20.0 g, 0.2080 mole) and cesium carbonate (135.5 g, 0.4158 mole) in N,N-dimethylformamide (100 mL), ethyl-3-bromopropionate (37.66 g, 0.2080 mole) was added at 25° C. to 30° C. The reaction mixture was heated to 40° C. and stirred for 3 hours. The reaction mixture further heated to 90° C. and stirred for 3 hours. Subsequently, ethyl-3-bromo propionate (9.2 g, 0.050 mole) was added and stirred for 3 hours at 90° C. Thereafter, water (200 mL) was added and extracted reaction mixture with ethyl acetate (2×200 mL). The combined organic layer was washed with water and distilled to afford ethyl 3-(3,5-dimethyl-1H-pyrazol-1-yl) propanoate.

Yield: 32.6 g (79.9%)
HPLC Purity: 86.14%
$^1$H-NMR (400 MHz, DMSO-$d_6$): δ 5.73 (1H, s), 4.09-4.13 (2H, t), 4.00-4.06 (2H, q), 2.76-2.79 (2H, t), 2.20 (3H, s), 2.06 (3H, s), 1.15-1.18 (3H, t).
Mass: 197.09 ($M^+$+1)

Example-27: Preparation of ethyl 3-{4-[(7-hydroxy-6-methyl-indan-4-yl)-methyl]-3,5-dimethyl-1H-pyrazol-1-yl}propanoate To a stirred suspension of 5-methyl-indan-4-ol (5.0 g, 0.033 mole) and paraformaldehyde (1.01 g, 0.033 mole) in acetic acid (50 mL), ethyl 3-(3,5-dimethyl-1H-pyrazol-1-yl) propanoate (6.62 g, 0.033 mole) was added and stirred for 6 hours at 65° C. to 68° C. Subsequently, paraformaldehyde (0.30 g, 0.009 mole) and ethyl 3-(3,5-dimethyl-1H-pyrazol-1-yl)propanoate (1.98 g, 0.01 mole) were added and stirred for 6 hours at 65° C. to 68° C. The reaction mixture was cooled to 25° C. to 30° C. and water (150 mL) was added. The precipitated solid was filtered, washed with water and such dried. The filtered solid was suspended in ethyl acetate (70 mL) and stirred for 30 minutes at 65° C. The mixture was filtered, washed with ethyl acetate and dried to yield ethyl 3-{4-[(7-hydroxy-6-methyl-indan-4-yl)methyl]-3,5-dimethyl-1H-pyrazol-1-yl}propanoate as a white solid.

Yield: 4.45 g (37%)
HPLC Purity: 97.34%
$^1$H-NMR (400 MHz, DMSO-$d_6$): δ 8.10 (1H, s), 6.39 (1H, s), 4.10-4.12 (2H, t), 3.99-4.05 (2H, q), 3.42 (2H, s), 2.66-2.78 (6H, m), 2.08 (3H, s), 2.05 (3H, s), 1.93-1.98 (2H, m), 1.90 (3H, s), 1.13-1.17 (3H, t).
Mass: 357.17 ($M^+$+1)
Melting point: 158.09

Example-28: Preparation of 3-{4-[(7-hydroxy-6-methyl-indan-4-yl)methyl]-3,5-dimethyl-1H-pyrazol-1-yl}propanoic Acid To a stirred solution of ethyl 3-{4-[(7-hydroxy-6-methyl-indan-4-yl)methyl]-3,5-dimethyl-1H-pyrazol-1-yl}propanoate (4.0 g, 0.011 mole) in tetrahydrofuran (20 mL), aqueous sodium hydroxide solution [sodium hydroxide (0.897 g) in water (28 mL)] was added and stirred for 2 hours at 25° C. to 30° C. Ethyl acetate (40 mL) was added to the mixture and layers were separated. The aqueous layer was acidified to pH 2 with dilute hydrochloric acid. The precipitated solid was filtered, washed with water (50 mL) and suck dried. The filtered solid was suspended in ethyl acetate (40 mL) and stirred for 30 minutes at 25° C. to 30° C. The mixture was filtered, washed with ethyl acetate and dried to yield 3-{4-[(7-hydroxy-6-methyl-indan-4-yl) methyl]-3,5-dimethyl-1H-pyrazol-1-yl}propanoic acid as a white solid.

Yield: 2.2 g (59.7%)
HPLC Purity: 99.84%
$^1$H-NMR (400 MHz, DMSO-$d_6$): δ 12.31 (1H, bs), 8.11 (1H, s), 6.40 (1H, s), 4.07-4.11 (2H, t), 3.42 (2H, s), 2.67-2.76 (6H, m), 2.08 (3H, s), 2.02 (3H, s), 1.93-1.98 (2H, m), 1.90 (3H, s).
Mass: 329.15 ($M^+$+1)
Melting point: 212.38° C.

Example-29: Preparation of 4-(benzyloxy)-5-methyl-indane

To a clear solution of 5-methyl-indan-4-ol (30.0 g, 0.2027 mole) in N,N-dimethylformamide (70 mL), potassium carbonate (56.0 g, 0.4054 mole) was added and stirred for 30 minutes at 25° to 30° C. Subsequently, benzyl chloride (31.0 g, 0.2432 mole) and potassium iodide (3.37 g, 0.0203 mole) were added and stirred for 2 hours at 25° C. to 30° C. After completion of reaction, water (300 mL) and ethyl acetate were added and layers were separated. The ethyl acetate layer was dried and distilled to obtain residue. The obtained residue was purified by column chromatography using hexane:ethyl acetate to afford 4-(benzyloxy)-5-methyl-indane as a liquid.

Yield: 29.0 g (60.0%)
HPLC Purity: 95.35%

¹H-NMR (400 MHz, DMSO-d₆): δ 7.43-7.45 (2H, m), 7.14-7.39 (3H, m), 6.93-6.95 (1H, d), 6.80-6.86 (1H, d), 4.85 (2H, s), 2.85-2.89 (2H, m), 2.77-2.81 (2H, m), 2.21 (3H, s), 1.92-2.17 (2H, m).

Example-30: Preparation of ethyl 3-(4-{[7-(benzyloxy)-6-methyl-indan-4-yl]methyl}-3,5-dimethyl-1H-pyrazol-1-yl)propanoate To a stirred suspension of 4-(benzyloxy)-5-methyl-indane (1.0 g, 0.004 mole) and paraformaldehyde (126 mg, 0.004 mole) in acetic acid (10 mL), ethyl 3-(3,5-dimethyl-1H-pyrazol-1-yl)propanoate (824 mg, 0.004 mole) was added and stirred for 7 hours at 85° C. to 90° C. Subsequently, paraformaldehyde (126 mg, 0.004 mole) and anhydrous zinc chloride (100 mg) were added and stirred for 10 hours at 85° C. to 90° C. After completion of reaction, water (40 mL) was added and precipitated solid was filtered. The filtered solid was washed water and purified in hexane to afford ethyl 3-(4-{[7-(benzyloxy)-6-methyl-indan-4-yl]methyl}-3,5-dimethyl-1H-pyrazol-1-yl)propanoate as an off white solid.

HPLC Purity: 89.49%
¹H-NMR (400 MHz, DMSO-d₆): δ 7.33-7.44 (5H, m), 6.50 (1H, s), 4.82 (2H, s), 4.12-4.15 (2H, t), 4.00-4.05 (2H, q), 3.50 (2H, s), 2.85-2.87 (2H, t), 2.73-2.79 (4H, m), 2.10 (3H, s), 2.09 (3H, s), 1.98-2.00 (2H, m), 1.91 (3H, s), 1.11-1.15 (3H, t).
Mass: 447.11 (M⁺+1)
Melting point: 66.53° C.

Example-31: Preparation of 4-methoxy-5-methyl-indane

To a stirred solution of 5-methyl-indan-4-ol (10.0 g, 0.067 mole) in N,N-dimethylformamide (40 mL), potassium carbonate (18.65 g, 0.134 mole) was added and stirred for 30 minutes at 25° C. to 30° C. Subsequently, methyl iodide (14.36 g, 0.101 mole) was added and stirred for 26 hours at 25° C. to 30° C. Methyl iodide (2.0 mL) was added to the reaction mixture and stirred for 7 hours at 25° C. to 30° C. After completion of reaction of reaction, water (160 mL) and ethyl acetate (50 mL) were added and layers were separated. The ethyl acetate layer was washed with water and distilled to yield crude product, which was purified by CombiFlash® to afford 4-methoxy-5-methyl-indane.

Yield: 6.0 g (55.0%)
HPLC Purity: 99.30%
¹H-NMR (400 MHz, DMSO-d₆): δ 6.91-6.93 (1H, d), 6.82-6.84 (1H, d), 3.69 (3H, s), 2.85-2.89 (2H, t), 2.77-2.81 (2H, t), 2.16 (3H, s), 1.95-1.99 (2H, m).

Example-32: Preparation of ethyl 3-(4-{[7-(methoxy)-6-methyl-indan-4-yl]methyl}-3,5-dimethyl-1H-pyrazol-1-yl)propanoate To a stirred solution of 4-methoxy-5-methyl-indane (3.0 g, 0.018 mole) and ethyl 3-(3,5-dimethyl-1H-pyrazol-1-yl)propanoate (3.63 g, 0.018 mole) in acetic acid (15 mL), paraformaldehyde (0.55 g, 0.018 mole) and anhydrous tin (II) chloride (0.3 g) were added and stirred for 20 hours at 80° C. to 85° C. After completion of reaction, water (100 mL) was added and filtered the precipitated solid. The filtered solid was washed with water and suck dried. The solid was suspended in water (50 mL) and stirred for 30 minutes at 25° C. to 30° C. The mixture was filtered, washed with water and suck dried. The solid was further suspended in hexane (30 mL) and stirred for 1 hour at 25° C. to 30° C. The mixture was filtered, washed with hexane (2×10 mL) and dried to yield ethyl 3-(4-{[7-(methoxy)-6-methyl-indan-4-yl]methyl}-3,5-dimethyl-1H-pyrazol-1-yl)propanoate.

Yield: 2.68 g (39.18%)
HPLC Purity: 94.21%
¹H-NMR (400 MHz, DMSO-d₆): δ 6.47 (1H, s), 4.11-4.15 (2H, t), 3.99-4.05 (2H, q), 3.63 (3H, s), 3.48 (2H, s), 2.70-2.79 (6H, m), 2.06 (3H, s), 2.02 (3H, s), 1.95-2.00 (2H, m), 1.89 (3H, s), 1.15-1.18 (3H, t).
Mass: 371.21 (M⁺+1)
Melting point: 99.93° C.

Example-33: Preparation of 3-(4-{[7-(methoxy)-6-methyl-indan-4-yl]methyl}-3,5-dimethyl-1H-pyrazol-1-yl)propanoic acid To a stirred solution of ethyl 3-(4-{[7-(methoxy)-6-methyl-indan-4-yl]methyl}-3,5-dimethyl-1H-pyrazol-1-yl)propanoate (2.5 g, 0.006 mole) in tetrahydrofuran (12.5 mL), aqueous sodium hydroxide solution [sodium hydroxide (0.539 g) in water (12.5 mL)] was added and stirred for 2.5 hours at 25° C. to 30° C. After completion of reaction, water (20 mL) was added and washed reaction mixture with ethyl acetate (2×20 mL). The aqueous layer was acidified with dilute hydrochloric acid and stirred for 30 minutes at 25° C. to 30° C. The precipitated solid was filtered, washed with water (2×20 mL) and dried to yield 3-(4-{[7-(methoxy)-6-methyl-indan-4-yl]methyl}-3,5-dimethyl-1H-pyrazol-1-yl)propanoic acid as a white solid.

Yield: 1.88 g (81.38%)
HPLC Purity: 95.93%
¹H-NMR (400 MHz, DMSO-d₆): δ 12.3 (1H, s), 6.48 (1H, s), 4.08-4.12 (2H, t), 3.64 (3H, s), 3.48 (2H, s), 2.84-2.87 (2H, t), 2.68-2.75 (4H, m), 2.26 (6H, s), 2.10-2.23 (2H, m), 2.08 (3H).
Mass: 343.25 (M⁺+1)
Melting point: 158.86

Example-34: Preparation of 3-{4-[(7-hydroxy-6-methyl-indan-4-yl)methyl]-3,5-dimethyl-1H-pyrazol-1-yl}propanoic Acid To a stirred suspension of 3-(4-{[7-(methoxy)-6-methyl-indan-4-yl]methyl}-3,5-dimethyl-1H-pyrazol-1-yl)propanoic acid (1.5 g, 0.0043 mole) in dichloromethane (15 mL), boron tribromide (2.2 g, 0.0087 mole) in dichloromethane (7.5 mL) was slowly added at 3±3° C. and stirred for 2 hours at 25° C. to 30° C. Subsequently, water (70 mL) was added and stirred for 1 hour. The precipitated solid was filtered, washed with water (2×20 mL) and ethyl acetate (10 mL) and dried to yield 3-{4-[(7-hydroxy-6-methyl-indan-4-yl)methyl]-3,5-dimethyl-1H-pyrazol-1-yl}propanoic acid as a white solid HPLC Purity: 92.37%
¹H-NMR (400 MHz, DMSO-d₆): δ 6.43 (1H, s), 4.21-4.24 (2H, t), 3.50 (2H, s), 2.70-2.78 (4H, m), 2.67-2.68 (2H, t), 2.02 (3H, s), 2.03 (6H, s), 1.93-1.97 (2H, m).
Mass: 329.21 (M⁺+1)
Melting point: 214.59° C.

Example-35: Preparation of 3-{[7-(benzyloxy)-6-methyl-indan-4-yl]methyl}-pentane-2,4-dione To a stirred solution of 4-(benzyloxy)-5-methyl-indane (5.0 g, 0.0209 mole) and acetyl acetone (2.1 g, 0.0209 mole) in acetic acid (50 mL), paraformaldehyde (0.63 g, 0.0209 mole) and anhydrous zinc chloride (0.5 g) were added and stirred for 18 hours at 80° C. to 85° C. After completion of reaction, water (100 mL) was added and extracted with ethyl acetate (2×70 mL). The combined ethyl acetate layer was washed with water (2×100 mL), dried over sodium sulphate, and distilled to afford crude product, which was purified by CombiFlash® to afford 3-{[7-(benzyloxy)-6-methyl-indan-4-yl]methyl}pentane-2,4-dione as an yellow liquid.

Example-36: Preparation of 4-{[7-(benzyloxy)-6-methyl-indan-4-yl]methyl}-3,5-dimethyl-1H-pyrazole To a stirred solution of 3-{[7-(benzyloxy)-6-methyl-indan-4-yl]methyl}-pentane-2,4-dione (0.6 g, 0.0017 mole) in isopropyl alcohol (10 mL), hydrazine hydrate (0.094 g, 0.0019 mole) was added and stirred for 1 hour at 80° C. to 85° C. Subsequently, acetic acid (0.6 mL) was added and stirred for 10 hours at 80° C. to 85° C. After completion of reaction, water (30 mL) was added and extracted reaction mixture with ethyl acetate (2×20 mL). The combined ethyl acetate layer was washed with water (30 mL), dried over sodium sulphate and distilled to get crude product, which was purified by CombiFlash® to yield 4-{[7-(benzyl oxy)-6-methyl-indan-4-yl]methyl}-3,5-dimethyl-1H-pyrazole as a solid.

HPLC Purity: 98.19%

$^1$H-NMR (400 MHz, DMSO-$d_6$): δ 7.31-744 (5H, m), 6.53 (1H, s), 4.82 (2H, s), 3.50 (2H, s), 2.86-2.89 (2H, t), 2.73-2.77 (2H, t), 2.09 (3H, s), 1.97-2.01 (8H, m).

Mass: 347.16 ($M^+$+1)

Melting point: 132.58° C.

Example-37: Preparation of 3-[(7-hydroxy-6-methyl-indan-4-yl)methyl]-pentane-2,4-dione To a stirred solution of 5-methyl-indan-4-ol (20.0 g, 0.1349 mole) and acetyl acetone (13.51 g, 0.1349 mole) in acetic acid (200 mL), paraformaldehyde (4.05 g, 0.1349 mole) was added and stirred for 12 hours at 64° C. to 68° C. After completion of reaction, water (200 mL) was added and extracted reaction mixture with dichloromethane (2×150 mL). The combined dichloromethane layer was washed with water (2×100 mL), dried over sodium sulphate, and distilled to get crude product, which was purified by CombiFlash® to yield 3-[(7-hydroxy-6-methyl-indan-4-yl)methyl]pentane-2,4-dione as a yellowish solid.

Example-38: Preparation of 7-[(3,5-dimethyl-1H-pyrazol-4-yl)methyl]-5-methyl-indan-4-ol To a stirred solution of 3-[(7-hydroxy-6-methyl-indan-4-yl)methyl]pentane-2,4-dione (8.0 g, 0.0307 mole) in isopropyl alcohol (80 mL), hydrazine hydrate (3.078 g, 0.0615 mole) was added and stirred for 1 hour at 80° C. to 85° C. Subsequently, acetic acid (8.0 mL) was added and stirred for 12 hours at 80° C. to 85° C. The reaction mixture was cooled to 25° C. to 30° C. and stirred for 2 hours. The precipitated solid was filtered and dried to obtain 7-[(3,5-dimethyl-1H-pyrazol-4-yl)methyl]-5-methyl-indan-4-ol as a solid.

HPLC Purity: 96.74%

$^1$H-NMR (400 MHz, DMSO-$d_6$): δ 11.90 (1H, s), 8.10 (1H, s), 6.41 (1H, s), 3.43 (2H, s), 2.70-2.76 (4H, m), 2.08 (3H, s), 1.93-2.02 (8H, m).

Mass: 257.26 ($M^+$+1)

Melting point: 229.22° C.

Example-39: Preparation of ethyl 3-{4-[(7-hydroxy-6-methyl-indan-4-yl)methyl]-3,5-dimethyl-1H-pyrazol-1-yl}propanoate A stirred mixture of ethyl acrylate (4.0 mL) and 7-[(3,5-dimethyl-1H-pyrazol-4-yl)methyl]-5-methyl-indan-4-ol (1.0 g, 0.0039 mole) was heated to 90° C. to 95° C. and stirred for 9 hours. Another lot of ethyl acrylate (3.0 mL) was added and stirred for 5 hours at 90° C. to 95° C. The reaction mixture was extracted with dichloromethane (15 mL & 10 mL) and combined the organic layer. Hexane was slowly added to the combined organic layer and stirred for 20 minutes at 25° C. to 30° C. The precipitated solid was filtered and dried to afford ethyl 3-{4-[(7-hydroxy-6-methyl-indan-4-yl)methyl]-3,5-dimethyl-1H-pyrazol-1-yl}propanoate as a white solid.

HPLC Purity: 95.08%

$^1$H-NMR (400 MHz, DMSO-$d_6$): δ 8.10 (1H, s), 6.39 (1H, s), 4.13-4.17 (2H, t), 3.99-4.05 (2H, q), 3.45 (2H, s), 2.70-2.80 (4H, m), 2.66-2.68 (2H, t), 2.14 (3H, s), 2.10 (3H, s), 1.95-2.02 (2H, m), 1.92 (3H, s), 1.11-1.15 (3H, t).

Mass: 357.30 ($M^+$+1)

Melting point: 147.09° C.

Example-40: Preparation of 3-(3,5-dimethyl-1H-pyrazol-1-yl)propanoic Acid

To a stirred solution of ethyl 3-(3,5-dimethyl-1H-pyrazol-1-yl)propanoate (4.0 g, 0.020 mole) in tetrahydrofuran (10 mL), aqueous sodium hydroxide solution [sodium hydroxide (1.63 g) in water (10 mL)] was added and stirred for 90 minutes at 25° C. to 30° C. The reaction mixture was acidified by dilute hydrochloric acid (30 mL) and distilled to obtain residue. Methanol (10 mL) was added to the residue and distilled to get crude solid. Dichloromethane (25 mL) and methanol (25 mL) were added to the obtained crude solid and stirred for 15 minutes at 25° C. to 30° C. The reaction mixture was filtered to remove sodium chloride and the filtrate was distilled to obtain crude solid. Hexane (25 mL) was added to the crude solid and stirred for 30 minutes. The separated solid was filtered, washed with hexane (25 mL) and dried to yield 3-(3,5-dimethyl-1H-pyrazol-1-yl) propanoic acid as a white solid.

Yield: 3.2 g (93.3%)

$^1$H-NMR (400 MHz, DMSO-$d_6$): δ 6.04 (1H, s), 4.21-4.24 (2H, t), 2.81-2.85 (2H, t), 2.29 (3H, s), 2.19 (3H, s).

Mass: 169.11 ($M^+$+1)

Melting point: 260.16° C.

Example-41: Preparation of 3-{4-[(7-hydroxy-6-methyl-indan-4-yl)methyl]-3,5-dimethyl-1H-pyrazol-1-yl}propanoic Acid To a stirred suspension of 5-methyl-indan-4-ol (1.5 g, 0.010 mole) and paraformaldehyde (303 mg, 0.010 mole) in acetic acid (15 mL), 3-(3,5-dimethyl-1H-pyrazol-1-yl)propanoic acid (1.7 g, 0.010 mole) and anhydrous tin(II) chloride (150 mg) were added and stirred for 20 hours at 75° C. to 80° C. After completion of reaction, water (100 mL) was added, filtered, and washed with water (2×20 mL). The filtered solid was purified in ethyl acetate to yield 3-{4-[(7-hydroxy-6-methyl-indan-4-yl)methyl]-3,5-dimethyl-1H-pyrazol-1-yl}propanoic acid as an off white solid.

HPLC Purity: 92.93%

¹H-NMR (400 MHz, DMSO-d₆): δ 12.31 (1H, bs), 8.11 (1H, s), 6.40 (1H, s), 4.07-4.11 (2H, t), 3.42 (2H, s), 2.67-2.76 (6H, m), 2.08 (3H, s), 2.02 (3H, s), 1.93-1.98 (2H, m), 1.90 (3H, s).
Mass: 329.28 (W+1)
Melting point: 207.06° C.

Example-42: Preparation of ethyl 3-{4-[(7-hydroxy-6-methyl-indan-4-yl)methyl]-3,5-dimethyl-1H-pyrazol-1-yl}propanoate To a stirred solution of methyl-indan-4-ol (5.0 g, 0.033 mole) in toluene (50 mL), paraformaldehyde (1.01 g, 0.033 mole), ethyl 3-(3,5-dimethyl-1H-pyrazol-1-yl)propanoate (6.62 g, 0.033 mole), and p-toluene sulfonic acid (5.8 g, 0.033 mole) were added. The mixture was heated to 110° C. to 112° C. and stirred for 12 hours at 110° C. to 112° C. The by-product water formed during reaction was removed with dean-stark apparatus while stirring. The reaction mixture was cooled to 25° C. to 30° C., hexane was added and stirred for 2 hours at 25° C. to 30° C. The precipitated solid was filtered, washed with hexane (2×15 mL) and suck dried to yield ethyl 3-{4-[(7-hydroxy-6-methyl-indan-4-yl)methyl]-3,5-dimethyl-1H-pyrazol-1-yl}propanoate as a white solid.
HPLC Purity: 2.5 g (94.81%)
¹H-NMR (400 MHz, DMSO-d₆): δ 8.11 (1H, s), 6.39 (1H, s), 4.09-4.12 (2H, t), 3.99-4.05 (2H, q), 3.43 (2H, s), 2.66-2.79 (6H, m), 2.09 (3H, s), 2.05 (3H, s), 1.93-1.98 (2H, m), 1.91 (3H, s), 1.11-1.15 (3H, t).
Mass: 357.11 (W+1)
Melting point: 158.09

Example-43: Preparation of ethyl 3-(3,5-dimethyl-1H-pyrazol-1-yl) propanoate

A stirred suspension of 3,5-dimethyl-1H-pyrazole (20.0 g, 0.2080 mole), potassium carbonate (57.51 g, 0.4161 mole), 18-crown-6 (11.0 g, 0.0416 mole) in ethyl acetate (200 mL) was heated to 55° C. to 60° C. and stirred for 1 hour at 55° C. to 60° C. Subsequently, ethyl-3-chloropropionate (36.8 mL, 0.2705 mole) was slowly added at 55° C. to 60° C., then heated to 74° C. to 79° C. and stirred for 12 hours. Another lot of ethyl-3-chloropropionate (2.83 mL) was added and stirred for 4 hours at 74° C. to 79° C. After completion of reaction, water (200 mL) was added and layers were separated. The aqueous layer was extracted with ethyl acetate (200 mL), the combined organic layer was washed with water (2×120 mL), and distilled to yield ethyl 3-(3,5-dimethyl-1H-pyrazol-1-yl)propanoate as liquid.
Yield: 40.0 g (98.0%)
HPLC Purity: 97.77%

Example-44: Preparation of 3-{4-[(7-hydroxy-6-methyl-indan-4-yl)methyl]-3,5-dimethyl-1H-pyrazol-1-yl}propanoic Acid A stirred suspension of ethyl 3-(3,5-dimethyl-1H-pyrazol-1-yl) propanoate (5.0 g, 0.025 mole), paraformaldehyde (0.687 g, 0.022 mole) in acetic acid (20 mL) was heated to 70° C. to 75° C. and stirred for 3 hours. Subsequently, anhydrous zinc chloride (500 mg) and a solution of 5-methyl-indan-4-ol (3.39 g, 0.022 mole) in acetic acid (5.0 mL) were added and stirred for 8 hours at 70° C. to 75° C. Aqueous hydrochloric acid (50 mL) was added to the reaction mixture and stirred for 4 hours at 70° C. to 75° C. The reaction mixture was cooled to 25° C. to 30° C., the precipitated solid was filtered, and washed with water (50 mL). The filtered solid was dissolved in N,N-dimethylformamide (25 mL) and slowly added water (75 mL) to the clear solution at 25° C. to 30° C. The precipitated solid was filtered and washed with water (50 mL). Isopropyl alcohol (45 mL) was added to the wet solid, heated to 75° C. to 80° C. and stirred for 1 hour. The mixture was cooled to 25° C. to 30° C. and precipitated solid was filtered. The filtered solid was washed with isopropyl alcohol (20 mL) and dried to yield 3-{4-[(7-hydroxy-6-methyl-indan-4-yl)methyl]-3,5-dimethyl-1H-pyrazol-1-yl}propanoic acid as a white solid.
Yield: 2.0 g Example-45: Preparation of Crystalline Form-$T_{15\text{-}1}$ To a suspension of 3-{4-[(7-hydroxy-6-methyl-indan-4-yl)methyl]-3,5-dimethyl-1H-pyrazol-1-yl}propanoic acid (15.0 g, 0.0456 mole) in water (150.0 mL), aqueous sodium hydroxide solution (3.65 g sodium hydroxide in 150 mL water) was slowly added at 25° C. to 30° C. and stirred for 10 minutes. Thereafter, the reaction mixture was cooled to 26° C. to 29° C. and slowly added aqueous hydrochloric acid solution (15 mL concentrated hydrochloric acid in 90 mL water) at 26° C. to 29° C. and stirred for 30 minutes. The precipitated solid was filtered, washed with water (2×30 mL) and suck dried. The filtered solid was suspended in water (300 mL), stirred for 1 hour at 25° C. to 30° C., filtered, and washed with water. The filtered solid was further suspended in ethyl acetate (150 mL), stirred for 15 minutes at 25° C. to 30° C., filtered, and washed with ethyl acetate (105 mL) to yield crystalline Form-$T_{15\text{-}1}$.
Yield: 6.5 g
HPLC Purity: 98.80%

Example-46: Preparation of Crystalline Form-$T_{15\text{-}2}$

To a suspension of 3-{4-[(7-hydroxy-6-methyl-indan-4-yl)methyl]-3,5-dimethyl-1H-pyrazol-1-yl}propanoic acid (15.0 g, 0.0456 mole) in water (150 mL), aqueous sodium hydroxide solution (5.48 g sodium hydroxide in 150 mL water) was added slowly at 25° C. to 30° C. and stirred for 10 minutes. Thereafter, the reaction mixture was cooled to 0° C. to 5° C. and aqueous hydrochloric acid solution (15 mL concentrated hydrochloric acid in 90 mL water) was slowly added at 0° C. to 5° C. and stirred for 5 minutes. The separated solid was filtered, washed with chilled water (2×30 mL), and dried in vacuum tray dryer for 8 hours at 25° C. to 30° C. to yield crystalline Form-$T_{15\text{-}2}$.
Yield: 13.0 g (86.7%)
HPLC Purity: 99.53%

Example-47: Preparation of Crystalline Form-$T_{15\text{-}3}$

To a suspension of ethyl 3-{4-[(7-hydroxy-6-methyl-indan-4-yl)methyl]-3,5-dimethyl-1H-pyrazol-1-yl}propanoate (72.0 g, 0.2020 mole) in tetrahydrofuran (360 mL), aqueous sodium hydroxide solution (16.16 g sodium hydroxide in 504 mL water) was added and stirred for 3 hours at 25° C. to 30° C. After completion of reaction, ethyl acetate was added, layers were separated, and the aqueous layer was acidified with aqueous hydrochloric acid solution (72 mL concentrated hydrochloric acid in 432 mL water). The separated solid was filtered and washed with water. The filtered solid was suspended in water (1440 mL), stirred for 1 hour, filtered, and washed with water and then with ethyl acetate. The filtered solid was further suspended in ethyl acetate (720 mL), stirred for 10 minutes, filtered, washed with ethyl acetate, and dried to yield crystal Form-$T_{15\text{-}3}$.
Yield: 56.0 g (84.4%)
HPLC Purity: 99.78%

Example-48: Preparation of Crystalline Form-T$_{15-4}$

To a suspension of 3-{4-[(7-hydroxy-6-methyl-indan-4-yl)methyl]-3,5-dimethyl-1H-pyrazol-1-yl}propanoic acid (5.0 g, 0.0152 mole) in water (50 mL), aqueous sodium hydroxide solution (1.83 g sodium hydroxide in 50 mL water) was added slowly and stirred for 10 minutes at 25° C. to 30° C. The reaction mixture was cooled to 0° C. to 5° C. and aqueous hydrochloric acid solution (5 mL concentrated hydrochloric acid in 30 mL water) was slowly added and stirred for 30 minutes. The separated solid was filtered, washed with water (2×30 mL), and air dried to yield crystalline Form-T$_{15-4}$.
Yield: 3.5 g (70.0%)
HPLC Purity: 99.03%

Example-49: Preparation of DMSO Solvate

A suspension of 3-{4-[(7-hydroxy-6-methyl-indan-4-yl)methyl]-3,5-dimethyl-1H-pyrazol-1-yl}propanoic acid (5.0 g) in dimethyl sulfoxide (DMSO) (12 mL) was stirred for 5 minutes at 22° C. to 25° C. to obtain clear solution. The mixture was stirred for 5 minutes, dimethyl sulfoxide (13 mL) was added and stirred for 2 hours at 25° C. to 30° C. The separated solid was filtered, washed with dimethyl sulfoxide (2×2.5 mL) and dried to yield DMSO solvate.
Yield: 4.08 g (66.0%)
HPLC Purity: 99.75%

Example-50: Preparation of Crystalline Form-T$_{15-3}$

DMSO solvate (3.1 g) was suspended in water (18 mL) and stirred for 3 hours at 25° C. to 30° C. The mixture was filtered, washed with water (45 mL), and dried to yield crystalline Form-T$_{15-3}$.
Yield: 1.5 g

Example-51: Preparation of Di-Sodium Salt of 3-{4-[(7-hydroxy-6-methyl-indan-4-yl)methyl]-3,5-dimethyl-1H-pyrazol-1-yl}propanoic Acid To a suspension of 3-{4-[(7-hydroxy-6-methyl-indan-4-yl)methyl]-3,5-dimethyl-1H-pyrazol-1-yl}propanoic acid (5.0 g, 0.0152 mole) in acetone (35 mL), aqueous sodium hydroxide solution (1.34 g sodium hydroxide in 10 mL water) was slowly added at 20° C. to 24° C. and then water (45 mL) was added and stirred for 30 minutes at 25° C. to 30° C. Subsequently, acetone (100 mL) was added and stirred for 1 hour. The separated solid was filtered, washed with acetone (25 mL), and dried to yield desired product.
Yield: 5.0 g (88.0%)
HPLC Purity: 99.33%

Example-52: Preparation of Crystalline Form-T$_{15-3}$

To a clear solution of 3-{4-[(7-hydroxy-6-methyl-indan-4-yl)methyl]-3,5-dimethyl-1H-pyrazol-1-yl}propanoic acid (1.0 g) in N,N-dimethylformamide, water (30 mL) was added at 25° C. to 30° C. The precipitated solid was filtered and suck dried to afford crystalline Form-T$_{15-3}$.
Yield: 0.9 g (90.0%)

Example-53: Preparation of Crystalline Form-T$_{15-3}$

Crystalline Form-T$_{15-2}$ (350.0 mg) was heated at 200° C. on hot plate and cooled to 25° C. to 30° C. to yield crystalline Form-T$_{15-3}$.

Example-54: Preparation of Crystalline Form-Tis-3

A suspension of crystalline Form-T$_{15-1}$ (2.0 g) in methanol (30 mL) was stirred at 62° C. to 65° C. for 2 hours and cooled to 25° C. to 30° C. The separated solid was filtered and dried to yield crystalline Form-T$_{15-3}$.
Yield: 1.38 g

Example-55: Preparation of Crystalline Form-T$_{15-1}$

A clear solution of 3-{4-[(7-hydroxy-6-methyl-indan-4-yl)methyl]-3,5-dimethyl-1H-pyrazol-1-yl}propanoic acid (2.0 g) in N,N-dimethylformamide (20.0 mL) was cooled to −20° C. to −25° C. and then chilled mixture of methanol (30 mL) and water (30 mL) was added at −20° C. to −25° C. The precipitated solid was filtered and suck dried to afford crystalline Form-T$_{15-1}$
Yield: 1.60 g

Example-56: Preparation of Ethyl 3-(3,5-dimethyl-1H-pyrazol-1-yl)propanoate

To a stirred suspension of 3,5-dimethyl-1H-pyrazole (400.0 g, 4.161 mole) and potassium carbonate (1150.1 g, 8.3220 mole) in acetonitrile (2 L), 18-crown-6 ether (40 g) was added and the mixture was heated to 72±5° C. Subsequently, ethyl-3-chloro propionate (738.8 g, 5.4092 mole) was added to the reaction mixture and stirred for 10 hours to 14 hours at 72±5° C. After completion of reaction, the reaction mixture was cooled to 30±5° C., water (4800 mL) was added and stirred for 20 minutes. The aqueous layer was separated and extracted aqueous layer with acetonitrile (800 mL). The combined organic layer was washed with 20% aqueous sodium chloride solution (2×2000 mL) and distilled off to yield ethyl 3-(3,5-dimethyl-1H-pyrazol-1-yl)propanoate.
Yield: 750.0 g (91.8%)
HPLC Purity: 99.18%

Example-57: Preparation of qethyl 3-{4-[(7-hydroxy-6-methyl-indan-4-yl)methyl]-3,5-dimethyl-1H-pyrazol-1-yl}propanoate To a clear solution of ethyl 3-(3,5-dimethyl-1H-pyrazol-1-yl)propanoate (30.0 g, 0.1529 mole) in acetic acid (120 mL), paraformaldehyde (4.13 g, 0.1376 mole) was added and stirred the reaction mixture at 82±3° C. for 2 hours. Subsequently, 5-methyl-indan-4-ol (18.12 g, 0.1223 mole) and concentrated sulphuric acid (1.5 g) in acetic acid (120 mL) were added at 82±3° C. and stirred the reaction mixture for 6 hours at 82±3° C. After completion of reaction, the mixture was cooled to 42±3° C. and water (480 mL) was added. The precipitated solid was filtered, washed with water and dried to obtain ethyl 3-{4-[(7-hydroxy-6-methyl-indan-4-yl)methyl]-3,5-dimethyl-1H-pyrazol-1-yl}propanoate as a white solid.
Yield: 35.1 g (80.7%)
HPLC Purity: 96.3%

Example-58: Preparation of Amorphous Form of 3-{4-[(7-hydroxy-6-methyl-indan-4-yl)methyl]-3,5-dimethyl-1H-pyrazol-1-yl}propanoic Acid To a clear solution of 3-{4-[(7-hydroxy-6-methyl-indan-4-yl)methyl]-3,5-dimethyl-1H-pyrazol-1-yl}propanoic acid (5.0 g) in methanol (250 mL), solution of povidone K-30 (5.0 g) in methanol (150 mL) was added at 28±3° C. to obtain mixture. The obtained mixture was spray dried to yield amorphous form of 3-{4-[(7-hydroxy-6-methyl-indan-4-yl)methyl]-3,5-dimethyl-1H-pyrazol-1-yl}propanoic acid.

Yield: 2.5 g

HPLC Purity: 98.48%

The invention claimed is:

1. A method for producing substituted pyrazole compound of Formula (I):

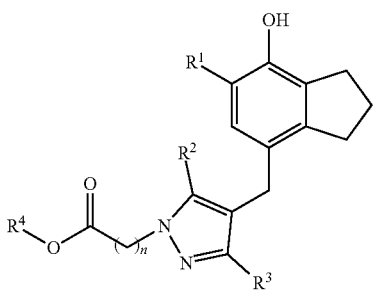

wherein:

$R^1$, $R^2$ and $R^3$ are each independently selected from H, $C_{1-6}$ alkyl, $C_{1-6}$ alkoxy, or halogen;

$R^4$ is selected from H, $C_{1-10}$ saturated or unsaturated alkyl, $C_{1-10}$ substituted or unsubstituted arylalkyl, $C_{3-10}$ cycloalkyl, aryl, heteroaryl, $C_{1-10}$ alkyl silyl, $C_{1-10}$ alkyl silyl ethers, substituted or unsubstituted haloalkyl, or $C_{1-20}$ alkyl tricyclic;

n is 1 to 5;

or its pharmaceutically acceptable salts, solvates, co-crystals, and hydrates thereof;

comprising condensing a compound of Formula (XIX),

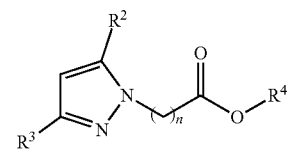

wherein $R^2$, $R^3$, $R^4$ and n are as defined above; with a compound of Formula (XX),

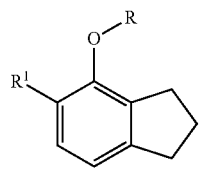

wherein R is H or $Pg^1$;

wherein $Pg^1$ is hydroxy protecting group, and $R^1$ is as defined above; in the presence of a condensing agent to obtain a compound of Formula (VIIIa),

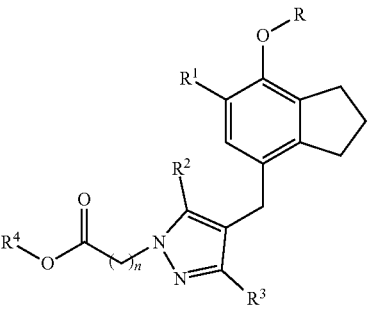

wherein R, $R^1$, $R^2$, $R^3$, $R^4$ and n are as defined above; and optionally deprotecting and/or hydrolysing the compound of Formula (VIIIa) to yield substituted pyrazole compound of Formula (I).

2. The method according to claim 1, wherein the substituents $R^2$, and $R^3$ are methyl; $R^4$ is H or $C_{1-6}$ alkyl; n is 2; and $Pg^1$ is methyl or benzyl.

3. The method according to claim 1, wherein the condensing agent is selected from the group comprising formaldehyde, paraformaldehyde, 1,3,5-trioxane, or mixtures thereof.

4. The method according to claim 1, wherein the condensation of a compound of Formula (XIX) with a compound of Formula (XX) is carried out optionally in the presence of acid catalyst selected from hydrochloric acid, sulphuric acid, p-toluenesulfonic acid, zinc chloride, or tin(II) chloride.

5. The method according to claim 1, wherein the condensation reaction is carried out in the presence of a solvent selected from acetic acid, N,N-dimethylformamide, N,N-dimethylacetamide, dimethyl sulphoxide, acetonitrile, N-methylpyrrolidone, cyclohexane, toluene, xylene or benzene.

6. The method according to claim 1, wherein the deprotection of a compound of Formula (VIIIa) is carried out in the presence of boron tribromide or palladium on carbon.

7. The method according to claim 1, wherein the hydrolysis of a compound of Formula (VIIIa) is carried out in the presence of a base selected from lithium hydroxide, sodium hydroxide, potassium hydroxide, magnesium hydroxide, sodium carbonate, potassium carbonate, cesium carbonate, magnesium carbonate, sodium bicarbonate, and potassium bicarbonate.

8. The method according to claim 1, wherein R is H.

* * * * *